United States Patent
Garfunkle et al.

(10) Patent No.: US 10,245,264 B2
(45) Date of Patent: Apr. 2, 2019

(54) SUBSTITUTED IMIDAZO[1,2-A]PYRAZINES AS SOLUBLE GUANYLATE CYCLASE ACTIVATORS

(71) Applicant: Merck Sharp & Dohme Corp., Rahway, NJ (US)

(72) Inventors: Joie Garfunkle, Metuchen, NJ (US); Olga Ornoski, Teaneck, NJ (US); Dann L. Parker, Jr., Cranford, NJ (US); Subharekha Raghavan, Bridgewater, NJ (US); Libo Xu, Bridgewater, NJ (US)

(73) Assignee: Merck Sharp & Dohme Corp., Rahway, NJ (US)

( * ) Notice: Subject to any disclaimer, the term of this patent is extended or adjusted under 35 U.S.C. 154(b) by 0 days.

(21) Appl. No.: 15/575,978

(22) PCT Filed: May 23, 2016

(86) PCT No.: PCT/US2016/033692
§ 371 (c)(1),
(2) Date: Nov. 21, 2017

(87) PCT Pub. No.: WO2016/191334
PCT Pub. Date: Dec. 1, 2016

(65) Prior Publication Data
US 2018/0147208 A1     May 31, 2018

Related U.S. Application Data

(60) Provisional application No. 62/166,949, filed on May 27, 2015.

(51) Int. Cl.
| | |
|---|---|
| A61K 31/4985 | (2006.01) |
| C07D 487/04 | (2006.01) |
| A61K 31/519 | (2006.01) |
| A61K 45/06 | (2006.01) |
| C07D 519/00 | (2006.01) |
| A61P 9/08 | (2006.01) |

(52) U.S. Cl.
CPC ............ *A61K 31/519* (2013.01); *A61K 45/06* (2013.01); *A61P 9/08* (2018.01); *C07D 519/00* (2013.01)

(58) Field of Classification Search
CPC ........................ A61K 31/4985; C07D 487/04
USPC .......................................... 514/249; 544/350
See application file for complete search history.

(56) References Cited

U.S. PATENT DOCUMENTS

| | | |
|---|---|---|
| 6,743,798 B1 | 6/2004 | Straub et al. |
| 7,173,037 B2 | 2/2007 | Alonso-Alija et al. |
| 8,420,656 B2 | 4/2013 | Follmann et al. |
| 8,455,638 B2 | 6/2013 | Bittner et al. |
| 8,507,512 B2 | 8/2013 | Kim et al. |
| 8,741,910 B2 | 6/2014 | Brockunier et al. |
| 8,859,569 B2 | 10/2014 | Follmann et al. |
| 8,895,583 B2 | 11/2014 | Tan et al. |
| 9,023,849 B2 | 5/2015 | Follmann et al. |
| 9,090,610 B2 | 7/2015 | Follmann et al. |
| 9,216,978 B2 | 12/2015 | Follmann et al. |
| 9,284,301 B2 | 3/2016 | Schmidt et al. |
| 9,365,574 B2 | 6/2016 | Raghavan et al. |
| 9,611,278 B2 | 4/2017 | Han et al. |
| 9,783,552 B2 | 10/2017 | Han et al. |
| 9,796,733 B2 * | 10/2017 | Campbell et al. ... C07D 519/00 |
| 9,822,130 B2 | 11/2017 | Berger et al. |
| 2011/0218202 A1 | 9/2011 | Brockunier et al. |
| 2013/0012511 A1 | 1/2013 | Schmidt et al. |

(Continued)

FOREIGN PATENT DOCUMENTS

WO     2016191335 A1     12/2016

OTHER PUBLICATIONS

Jordan, V. C. Nature Reviews: Drug Discovery, 2, 2003, 205.*
Hackam, et al. JAMA, 296(14), 2006, 1731-1732.*
Follmann, N. et al., The Chemistry and Biology of Soluble Guanylate Cyclase Stimulators and Activators, Angewandte Chemie—International Edition, 2013, pp. 9442-9462, vol. 52, Issue 36.
International Search Report and Written Opinion for PCT/US/2016/033693, dated Aug. 25, 2016, 12 pages.

(Continued)

*Primary Examiner* — Douglas M Willis
(74) *Attorney, Agent, or Firm* — Eric A. Meade; John C. Todaro

(57) ABSTRACT

A compound of Formula I or a pharmaceutically acceptable salt thereof, are capable of modulating the body's production of cyclic guanosine monophosphate ("cGMP") and are generally suitable for the therapy and prophylaxis of diseases which are associated with a disturbed cGMP balance. The invention furthermore relates to processes for preparing compounds of Formula I, or pharmaceutically acceptable salt thereofs, for their use in the therapy and prophylaxis of the abovementioned diseases and for preparing pharmaceuticals for this purpose, and to pharmaceutical compositions which comprise compounds of Formula I or pharmaceutically acceptable salts thereof.

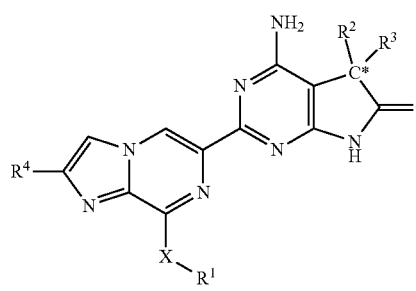

18 Claims, No Drawings

(56) References Cited

U.S. PATENT DOCUMENTS

| | | |
|---|---|---|
| 2013/0072492 A1 | 3/2013 | Raghavan et al. |
| 2014/0171434 A1 | 6/2014 | Follmann et al. |
| 2014/0228366 A1 | 8/2014 | Follmann et al. |
| 2014/0357637 A1 | 12/2014 | Follmann et al. |
| 2017/0032060 A1 | 2/2017 | Davidi et al. |
| 2017/0174693 A1 | 6/2017 | Berger et al. |

OTHER PUBLICATIONS

European Search Report for corresponding EP Application No. 168005775-1116—Oct. 4, 2018.

\* cited by examiner

SUBSTITUTED IMIDAZO[1,2-A]PYRAZINES AS SOLUBLE GUANYLATE CYCLASE ACTIVATORS

CROSS REFERENCE TO RELATED APPLICATIONS

This application is a U.S. National Phase application under 35 U.S.C. § 371 of PCT Application No. PCT/US2016/033692, filed May 23, 2016, which claims priority under 35 U.S.C. § 119(e) from U.S. Provisional Application No. 62/166,949, filed May 27, 2015.

BACKGROUND OF THE INVENTION

Cyclic GMP (cGMP) is an important intracellular messenger which triggers a multitude of different effects via the modulation of cGMP-dependent protein kinases, phosphodiesterases and ion channels. Examples are the relaxation of smooth muscles, the inhibition of thrombocyte activation and the inhibition of the proliferation of smooth-muscle cells and of leukocyte adhesion. cGMP is produced by particulate and soluble guanylate cyclases as a response to a number of extracellular and intracellular stimuli. In the case of the particulate guanylate cyclases, stimulation is essentially effected by peptidic messengers, such as the atrial natriuretic peptide or the cerebral natriuretic peptide. The soluble guanylate cyclases ("sGC"), which are cytosolic heterodimeric heme proteins, in contrast, are essentially regulated by a family of low-molecular-weight factors which are formed enzymatically. The most important stimulant is nitrogen monoxide ("NO") or a closely related species. The function of other factors such as carbon monoxide or the hydroxyl radical is still largely unclear. The binding of NO to the heme with formation of a penta-coordinate heme-nitrosyl complex is proposed as the mechanism of the activation by NO. The associated release of the histidine which is bound in the basal state to the iron converts the enzyme into the active confirmation.

Active soluble guanylate cyclases are each composed of an α and a β subunit. Several subunit subtypes have been described which differ from one another with respect to sequence, tissue-specific distribution and expression in different development stages. The subtypes $\alpha_1$ and $\beta_1$ are mainly expressed in brain and lung, while $\beta_2$ is found in particular in liver and kidney. The subtype $\alpha_2$ was shown to be present in human fetal brain. The subunits referred to as $\alpha_3$ and $\beta_3$ were isolated from human brain and are homologous to $\alpha_1$ and $\beta_1$. More recent works indicate an $\alpha_{2i}$ subunit which contains an insert in the catalytic domain. All subunits show great homologies in the region of the catalytic domain. The enzymes presumably contain one heme per heterodimer, which is bound via $\beta_1$-Cys-78 and/or $\beta_1$-His-105 and is part of the regulatory center.

Under pathologic conditions, the formation of guanylate-cyclase-activating factors can be reduced, or their degradation may be promoted owing to the increased occurrence of free radicals. The resulting reduced activation of the sGC leads, via a weakening of the respective cGMP-mediated cellular response, for example to an increase of the blood pressure, to platelet activation or to increased cell proliferation and cell adhesion. As a consequence, formation of endothelial dysfunction, atherosclerosis, hypertension, stable or unstable angina pectoris, thrombosis, myocardial infarction, strokes or erectile dysfunction results. Pharmacological stimulation of sGC offers a possibility to normalize cGMP production and therefore makes possible the treatment and/or prevention of such disorders.

For the pharmacological stimulation of the sGC, use has been made of compounds whose activity is based on an intermediate NO release, for example organic nitrates. The drawback of this treatment is the development of tolerance and a reduction of activity, and the higher dosage which is required because of this.

Various sGC stimulators which do not act via NO release were described by Vesely in a series of publications. However, the compounds, most of which are hormones, plant hormones, vitamins or natural compounds such as, for example, lizard poisons, predominantly only have weak effects on the cGMP formation in cell lysates. D. L. Vesely, Eur. J. Clin. Invest., vol. 15, 1985, p. 258; D. L. Vesely, Biochem. Biophys. Res. Comm., vol. 88, 1979, p. 1244. A stimulation of heme-free guanylate cyclase by protoporphyrin IX was demonstrated by Ignarro et al., Adv. Pharmacol., vol. 26, 1994, p. 35. Pettibone et al., Eur. J. Pharmacol., vol. 116, 1985 p. 307, described an antihypertensive action of diphenyliodonium hexafluorophosphate and attributed this to a stimulation of sGC. According to Yu et al., Brit. J. Pharmacol, vol. 114, 1995, p. 1587, isoliquiritigenin, which has a relaxing action on isolated rat aortas, also activates sGC. Ko et al., Blood vol. 84, 1994, p. 4226, Yu et al., Biochem. J. vol. 306, 1995, p. 787, and Wu et al., Brit. J. Pharmacol. vol. 116, 1995, p. 1973, demonstrated a sGC-stimulating activity of 1-benzyl-3-(5-hydroxymethyl-2-furyl)indazole and demonstrated an antiproliferative and thrombocyte-inhibiting action. Pyrazoles and fused pyrazoles which exhibit a sGC-stimulating activity are described in European Patent Application No. 908,456 and German Patent Application No. 19,744,027.

It has now been found that the compounds of the present invention effect a strong activation of soluble guanylate cyclase and are therefore suitable for the therapy and prophylaxis of disorders which are associated with a low cGMP level.

SUMMARY OF THE INVENTION

The present invention relates to compounds which activate soluble guanylate cyclase and are valuable pharmaceutically active compounds for the therapy and prophylaxis of diseases, for example for cardiovascular diseases such as hypertension, heart failure, pulmonary hypertension, angina pectoris, diabetes, cardiac insufficiency, thrombosis, chronic kidney disease, fibrosis or atherosclerosis. The compounds of Formula I

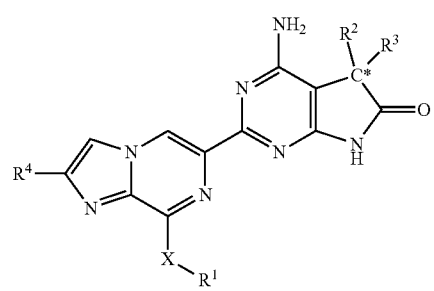

are capable of modulating the body's production of cyclic guanosine monophosphate ("cGMP") and may be suitable for the therapy and prophylaxis of diseases which are associated with a disturbed cGMP balance. The invention furthermore relates to processes for preparing compounds of Formula I, to the use of such compounds for the therapy and prophylaxis of the abovementioned diseases and for preparing pharmaceuticals for this purpose, and to pharmaceutical compositions which comprise compounds of Formula I.

DETAILED DESCRIPTION OF THE INVENTION

The present invention is directed to compounds having structural Formula I:

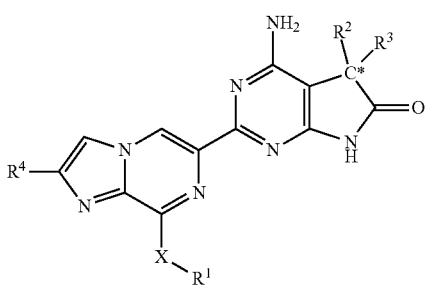

I or a pharmaceutically acceptable salt thereof wherein:
C* indicates a potential chiral carbon atom;
X is
 (1) O,
 (2) NH, or
 (3) S;
$R^1$ is
 (1) phenyl unsubstituted or substituted by 1 to 3 halo,
 (2) $(C_{1-6})$alkyl unsubstituted or substituted by $(C_{1-3})$alkyl,
 (3) halo$(C_{1-6})$alkyl,
 (4) $(C_{3-7})$cycloalkyl unsubstituted or substituted by 1 to 2 halo,
 (5) 5- or 6-membered heteroaryl containing 1, 2, or 3 heteroatoms independently selected from N, O and S, wherein the heteroaryl is unsubstituted or substituted by 1 to 2 halo, $(C_{1-3})$alkyl, or halo$(C_{1-3})$alkyl,
 (6) —$(C_{1-3})$alkyl-$(C_{3-7})$cycloalkyl is unsubstituted or substituted by 1 to 2 $(C_{1-3})$alkyl, or halo groups,
 (7) —$(C_{1-3})$alkyl-phenyl, wherein phenyl is unsubstituted or substituted by one to three halo, or
 (8) —$(C_{1-3})$alkyl-heterocyclyl containing 1 or 2 heteroatoms independently selected from N and O, wherein the heterocyclyl is a 4-7 membered ring;
$R^2$ is
 (1) $(C_{1-3})$alkyl, or
 (2) $(C_{3-7})$cycloalkyl;
$R^3$ is
 (1) phenyl unsubstituted or substituted by 1 to 2 halo,
 (2) five- or six-membered heteroaryl containing 1, 2, or 3 heteroatoms independently selected from N, O and S heteroatoms, wherein heteroaryl is unsubstituted or substituted by 1 to 2 halo, or
 (3) $(C_{1-6})$alkyl; and
$R^4$ is
 (1) hydrogen,
 (2) $(C_{1-3})$alkyl,
 (3) halo$(C_{1-3})$alkyl, or
 (4) $(C_{3-6})$cycloalkyl.
In one embodiment, $R^1$ is $(C_{1-6})$alkyl; halo$(C_{1-6})$alkyl; $(C_{3-7})$cycloalkyl unsubstituted or substituted by 1 to 2 halo; —$(C_{1-3})$alkyl-$(C_{3-7})$cycloalkyl, wherein the cycloalkyl is unsubstituted or substituted by 1 to 2 $(C_{1-3})$alkyl, or halo; or —$(C_{1-3})$alkyl-heterocyclyl containing 1 to 2 heteroatoms independently selected from N and O, wherein the heterocyclyl is a 4-7 membered ring.

In one class of this embodiment, $R^3$ is phenyl unsubstituted or substituted by one to two halo.

In one subclass of this class, X is O. In a sub-subclass of this class, $R^4$ is hydrogen.

In one subclass of this class, X is S. In a sub-subclass of this class, $R^4$ is hydrogen.

In one subclass of this class, X is NH. In a sub-subclass of this class, $R^4$ is hydrogen.

In one class of this embodiment, $R^3$ is six-membered heteroaryl containing 1 or 2 N heteroatoms, wherein heteroaryl is unsubstituted or substituted by 1 to 2 halo.

In one subclass of this class, X is O. In a sub-subclass of this class, $R^4$ is hydrogen.

In one subclass of this class, X is S. In a sub-subclass of this class, $R^4$ is hydrogen.

In one subclass of this class, X is NH. In a sub-subclass of this class, $R^4$ is hydrogen.

In one class of this embodiment, $R^3$ is $(C_{1-6})$alkyl.

In one subclass of this class, X is O. In a sub-subclass of this class, $R^4$ is hydrogen.

In one subclass of this class, X is S. In a sub-subclass of this class, $R^4$ is hydrogen.

In one subclass of this class, X is NH. In a sub-subclass of this class, $R^4$ is hydrogen.

In one embodiment, $R^1$ is phenyl unsubstituted or substituted by 1 to 3 halo; 6-membered heteroaryl containing 1 or 2 N heteroatoms, wherein the heteroaryl is unsubstituted or substituted by 1 to 2 halo, $(C_{1-3})$alkyl, or halo$(C_{1-3})$alkyl; or —$(C_{1-3})$alkyl-phenyl, wherein phenyl is unsubstituted or substituted by one to three halo.

In one class of this embodiment, $R^3$ is phenyl unsubstituted or substituted by 1 to 2 halo.

In one subclass of this class, X is O. In a sub-subclass of this class, $R^4$ is hydrogen.

In one subclass of this class, X is S. In a sub-subclass of this class, $R^4$ is hydrogen.

In one subclass of this class, X is NH. In a sub-subclass of this class, $R^4$ is hydrogen.

In one class of this embodiment, $R^3$ is six-membered heteroaryl containing 1 or 2 N heteroatoms, wherein heteroaryl is unsubstituted or substituted by one to two halo.

In one subclass of this class, X is O. In a sub-subclass of this class, $R^4$ is hydrogen.

In one subclass of this class, X is S. In a sub-subclass of this class, $R^4$ is hydrogen.

In one subclass of this class, X is NH. In a sub-subclass of this class, $R^4$ is hydrogen.

In one class of this embodiment, $R^3$ is $(C_{1-6})$alkyl.

In one subclass of this class, X is O. In a sub-subclass of this class, $R^4$ is hydrogen.

In one subclass of this class, X is S. In a sub-subclass of this class, $R^4$ is hydrogen.

In one subclass of this class, X is NH. In a sub-subclass of this class, $R^4$ is hydrogen.

In one embodiment, $R^1$ is phenyl unsubstituted or substituted by 1 to 3 halo.

In one class of this embodiment, $R^3$ is phenyl unsubstituted or substituted by one to two halo.

In one subclass of this class, X is O. In a sub-subclass of this class, $R^4$ is hydrogen.

In one subclass of this class, X is S. In a sub-subclass of this class, $R^4$ is hydrogen.

In one subclass of this class, X is NH. In a sub-subclass of this class, $R^4$ is hydrogen.

In one class of this embodiment, $R^3$ is six-membered heteroaryl containing 1 or 2 N heteroatoms, wherein heteroaryl is unsubstituted or substituted by 1 to 2 halo.

In one subclass of this class, X is O. In a sub-subclass of this class, $R^4$ is hydrogen.

In one subclass of this class, X is S. In a sub-subclass of this class, $R^4$ is hydrogen.

In one subclass of this class, X is NH. In a sub-subclass of this class, $R^4$ is hydrogen.

In one class of this embodiment, $R^3$ is $(C_{1-6})$alkyl.

In one subclass of this class, X is O. In a sub-subclass of this class, $R^4$ is hydrogen.

In one subclass of this class, X is S. In a sub-subclass of this class, $R^4$ is hydrogen.

In one subclass of this class, X is NH. In a sub-subclass of this class, $R^4$ is hydrogen.

In one embodiment, $R^1$ is $(C_{1-6})$alkyl.

In one class of this embodiment, $R^3$ is phenyl unsubstituted or substituted by 1 to 2 halo.

In one subclass of this class, X is O. In a sub-subclass of this class, $R^4$ is hydrogen.

In one subclass of this class, X is S. In a sub-subclass of this class, $R^4$ is hydrogen.

In one subclass of this class, X is NH. In a sub-subclass of this class, $R^4$ is hydrogen.

In one class of this embodiment, $R^3$ is six-membered heteroaryl containing 1 or 2 N heteroatoms, wherein heteroaryl is unsubstituted or substituted by 1 to 2 halo.

In one subclass of this class, X is O. In a sub-subclass of this class, $R^4$ is hydrogen.

In one subclass of this class, X is S. In a sub-subclass of this class, $R^4$ is hydrogen.

In one subclass of this class, X is NH. In a sub-subclass of this class, $R^4$ is hydrogen.

In one class of this embodiment, $R^3$ is $(C_{1-6})$alkyl.

In one subclass of this class, X is O. In a sub-subclass of this class, $R^4$ is hydrogen.

In one subclass of this class, X is S. In a sub-subclass of this class, $R^4$ is hydrogen.

In one subclass of this class, X is NH. In a sub-subclass of this class, $R^4$ is hydrogen.

In one embodiment, $R^1$ is halo$(C_{1-6})$alkyl.

In one class of this embodiment, $R^3$ is phenyl unsubstituted or substituted by 1 to 2 halo.

In one subclass of this class, X is O. In a sub-subclass of this class, $R^4$ is hydrogen.

In one subclass of this class, X is S. In a sub-subclass of this class, $R^4$ is hydrogen.

In one subclass of this class, X is NH. In a sub-subclass of this class, $R^4$ is hydrogen.

In one class of this embodiment, $R^3$ is six-membered heteroaryl containing 1 or 2 N heteroatoms, wherein heteroaryl is unsubstituted or substituted by 1 to 2 halo.

In one subclass of this class, X is O. In a sub-subclass of this class, $R^4$ is hydrogen.

In one subclass of this class, X is S. In a sub-subclass of this class, $R^4$ is hydrogen.

In one subclass of this class, X is NH. In a sub-subclass of this class, $R^4$ is hydrogen.

In one class of this embodiment, $R^3$ is $(C_{1-6})$alkyl.

In one subclass of this class, X is O. In a sub-subclass of this class, $R^4$ is hydrogen.

In one subclass of this class, X is S. In a sub-subclass of this class, $R^4$ is hydrogen.

In one subclass of this class, X is NH. In a sub-subclass of this class, $R^4$ is hydrogen.

In one embodiment, $R^1$ is $(C_{3-7})$cycloalkyl unsubstituted or substituted by 1 to 2 halo.

In one class of this embodiment, $R^3$ is phenyl unsubstituted or substituted by 1 to 2 halo.

In one subclass of this class, X is O. In a sub-subclass of this class, $R^4$ is hydrogen.

In one subclass of this class, X is S. In a sub-subclass of this class, $R^4$ is hydrogen.

In one subclass of this class, X is NH. In a sub-subclass of this class, $R^4$ is hydrogen.

In one class of this embodiment, $R^3$ is six-membered heteroaryl containing 1 or 2 N heteroatoms, wherein heteroaryl is unsubstituted or substituted by 1 to 2 halo.

In one subclass of this class, X is O. In a sub-subclass of this class, $R^4$ is hydrogen.

In one subclass of this class, X is S. In a sub-subclass of this class, $R^4$ is hydrogen.

In one subclass of this class, X is NH. In a sub-subclass of this class, $R^4$ is hydrogen.

In one class of this embodiment, $R^3$ is $(C_{1-6})$alkyl.

In one subclass of this class, X is O. In a sub-subclass of this class, $R^4$ is hydrogen.

In one subclass of this class, X is S. In a sub-subclass of this class, $R^4$ is hydrogen.

In one subclass of this class, X is NH. In a sub-subclass of this class, $R^4$ is hydrogen.

In one embodiment, $R^1$ is 5- or 6-membered heteroaryl containing 1, 2, or 3 heteroatoms independently selected from N, O and S, wherein the heteroaryl is unsubstituted or substituted by 1 to 2 halo, $(C_{1-3})$alkyl, or halo$(C_{1-3})$alkyl.

In one class of this embodiment, $R^3$ is phenyl unsubstituted or substituted by 1 to 2 halo.

In one subclass of this class, X is O. In a sub-subclass of this class, $R^4$ is hydrogen.

In one subclass of this class, X is S. In a sub-subclass of this class, $R^4$ is hydrogen.

In one subclass of this class, X is NH. In a sub-subclass of this class, $R^4$ is hydrogen.

In one class of this embodiment, $R^3$ is six-membered heteroaryl containing 1 or 2 N heteroatoms, wherein heteroaryl is unsubstituted or substituted by 1 to 2 halo.

In one subclass of this class, X is O. In a sub-subclass of this class, $R^4$ is hydrogen.

In one subclass of this class, X is S. In a sub-subclass of this class, $R^4$ is hydrogen.

In one subclass of this class, X is NH. In a sub-subclass of this class, $R^4$ is hydrogen.

In one class of this embodiment, $R^3$ is $(C_{1-6})$alkyl.

In one subclass of this class, X is O. In a sub-subclass of this class, $R^4$ is hydrogen.

In one subclass of this class, X is S. In a sub-subclass of this class, $R^4$ is hydrogen.

In one subclass of this class, X is NH. In a sub-subclass of this class, $R^4$ is hydrogen.

In one embodiment, $R^1$ is —$(C_{1-3})$alkyl-$(C_{3-7})$cycloalkyl, wherein the cycloalkyl is unsubstituted or substituted by 1 to 2 $(C_{1-3})$alkyl, or halo.

In one class of this embodiment, $R^3$ is phenyl unsubstituted or substituted by 1 to 2 halo.

In one subclass of this class, X is O. In a sub-subclass of this class, $R^4$ is hydrogen.

In one subclass of this class, X is S. In a sub-subclass of this class, $R^4$ is hydrogen.

In one subclass of this class, X is NH. In a sub-subclass of this class, $R^4$ is hydrogen.

In one class of this embodiment, R³ is six-membered heteroaryl containing 1 or 2 N heteroatoms, wherein heteroaryl is unsubstituted or substituted by 1 to 2 halo.

In one subclass of this class, X is O. In a sub-subclass of this class, R⁴ is hydrogen.

In one subclass of this class, X is S. In a sub-subclass of this class, R⁴ is hydrogen.

In one subclass of this class, X is NH. In a sub-subclass of this class, R⁴ is hydrogen.

In one class of this embodiment, R³ is ($C_{1-6}$)alkyl.

In one subclass of this class, X is O. In a sub-subclass of this class, R⁴ is hydrogen.

In one subclass of this class, X is S. In a sub-subclass of this class, R⁴ is hydrogen.

In one subclass of this class, X is NH. In a sub-subclass of this class, R⁴ is hydrogen.

In one embodiment, R¹ is —($C_{1-3}$)alkyl-phenyl, wherein phenyl is unsubstituted or substituted by 1 to 3 halo.

In one class of this embodiment, R³ is phenyl unsubstituted or substituted by 1 to 2 halo.

In one subclass of this class, X is O. In a sub-subclass of this class, R⁴ is hydrogen.

In one subclass of this class, X is S. In a sub-subclass of this class, R⁴ is hydrogen.

In one subclass of this class, X is NH. In a sub-subclass of this class, R⁴ is hydrogen.

In one class of this embodiment, R³ is six-membered heteroaryl containing 1 or 2 N heteroatoms, wherein heteroaryl is unsubstituted or substituted by 1 to 2 halo.

In one subclass of this class, X is O. In a sub-subclass of this class, R⁴ is hydrogen.

In one subclass of this class, X is S. In a sub-subclass of this class, R⁴ is hydrogen.

In one subclass of this class, X is NH. In a sub-subclass of this class, R⁴ is hydrogen.

In one class of this embodiment, R³ is ($C_{1-6}$)alkyl.

In one subclass of this class, X is O. In a sub-subclass of this class, R⁴ is hydrogen.

In one subclass of this class, X is S. In a sub-subclass of this class, R⁴ is hydrogen.

In one subclass of this class, X is NH. In a sub-subclass of this class, R⁴ is hydrogen.

In one embodiment, R¹ is —($C_{1-3}$)alkyl-heterocyclyl containing 1 or 2 heteroatoms independently selected from the group consisting of N and O, wherein the heterocyclyl is a 4-7 membered ring.

In one class of this embodiment, R³ is phenyl unsubstituted or substituted by 1 to 2 halo.

In one subclass of this class, X is O. In a sub-subclass of this class, R⁴ is hydrogen.

In one subclass of this class, X is S. In a sub-subclass of this class, R⁴ is hydrogen.

In one subclass of this class, X is NH. In a sub-subclass of this class, R⁴ is hydrogen.

In one class of this embodiment, R³ is six-membered heteroaryl containing 1 or 2 N heteroatoms, wherein heteroaryl is unsubstituted or substituted by 1 to 2 halo.

In one subclass of this class, X is O. In a sub-subclass of this class, R⁴ is hydrogen.

In one subclass of this class, X is S. In a sub-subclass of this class, R⁴ is hydrogen.

In one subclass of this class, X is NH. In a sub-subclass of this class, R⁴ is hydrogen.

In one class of this embodiment, R³ is ($C_{1-6}$)alkyl.

In one subclass of this class, X is O. In a sub-subclass of this class, R⁴ is hydrogen.

In one subclass of this class, X is S. In a sub-subclass of this class, R⁴ is hydrogen.

In one subclass of this class, X is NH. In a sub-subclass of this class, R⁴ is hydrogen.

In one embodiment, R³ is phenyl unsubstituted or substituted by 1 to 2 halo.

In one class of this embodiment, R² is a ($C_{1-3}$)alkyl.

In one subclass of this class, X is O. In one sub-subclass of this subclass, R⁴ is hydrogen.

In one subclass of this class, X is S. In one sub-subclass of this subclass, R⁴ is hydrogen.

In one subclass of this class, X is NH. In one sub-subclass of this subclass, R⁴ is hydrogen.

In one class of this embodiment, R² is a ($C_{3-7}$)cycloalkyl.

In one subclass of this class, X is O. In one sub-subclass of this subclass, R⁴ is hydrogen.

In one subclass of this class, X is S. In one sub-subclass of this subclass, R⁴ is hydrogen.

In one subclass of this class, X is NH. In one sub-subclass of this subclass, R⁴ is hydrogen.

In one embodiment, R³ is a five- or six-membered heteroaryl containing 1, 2, or 3 heteroatoms independently selected from N, O and S heteroatoms, wherein heteroaryl is unsubstituted or substituted by 1 to 2 halo.

In one class of this embodiment, R² is a ($C_{1-3}$)alkyl.

In one subclass of this class, X is O. In one sub-subclass of this subclass, R⁴ is hydrogen.

In one subclass of this class, X is S. In one sub-subclass of this subclass, R⁴ is hydrogen.

In one subclass of this class, X is NH. In one sub-subclass of this subclass, R⁴ is hydrogen.

In one class of this embodiment, R² is a ($C_{3-7}$)cycloalkyl.

In one subclass of this class, X is O. In one sub-subclass of this subclass, R⁴ is hydrogen.

In one subclass of this class, X is S. In one sub-subclass of this subclass, R⁴ is hydrogen.

In one subclass of this class, X is NH. In one sub-subclass of this subclass, R⁴ is hydrogen.

In one embodiment, R³ is a six-membered heteroaryl containing 1 or 2 N heteroatoms, wherein the heteroaryl is unsubstituted or substituted by 1 to 2 halo.

In one class of this embodiment, R² is a ($C_{1-3}$)alkyl.

In one subclass of this class, X is O. In one sub-subclass of this subclass, R⁴ is hydrogen.

In one subclass of this class, X is S. In one sub-subclass of this subclass, R⁴ is hydrogen.

In one subclass of this class, X is NH. In one sub-subclass of this subclass, R⁴ is hydrogen.

In one class of this embodiment, R² is a ($C_{3-7}$)cycloalkyl.

In one subclass of this class, X is O. In one sub-subclass of this subclass, R⁴ is hydrogen.

In one subclass of this class, X is S. In one sub-subclass of this subclass, R⁴ is hydrogen.

In one subclass of this class, X is NH. In one sub-subclass of this subclass, R⁴ is hydrogen.

In one embodiment, R³ is ($C_{1-6}$)alkyl.

In one class of this embodiment, R² is a ($C_{1-3}$)alkyl.

In one subclass of this class, X is O. In one sub-subclass of this subclass, R⁴ is hydrogen.

In one subclass of this class, X is S. In one sub-subclass of this subclass, R⁴ is hydrogen.

In one subclass of this class, X is NH. In one sub-subclass of this subclass, R⁴ is hydrogen.

In one class of this embodiment, R² is a ($C_{3-7}$)cycloalkyl.

In one subclass of this class, X is O. In one sub-subclass of this subclass, R⁴ is hydrogen.

In one subclass of this class, X is S. In one sub-subclass of this subclass, R⁴ is hydrogen.

In one subclass of this class, X is NH. In one sub-subclass of this subclass, R⁴ is hydrogen.

In one embodiment, R¹ is

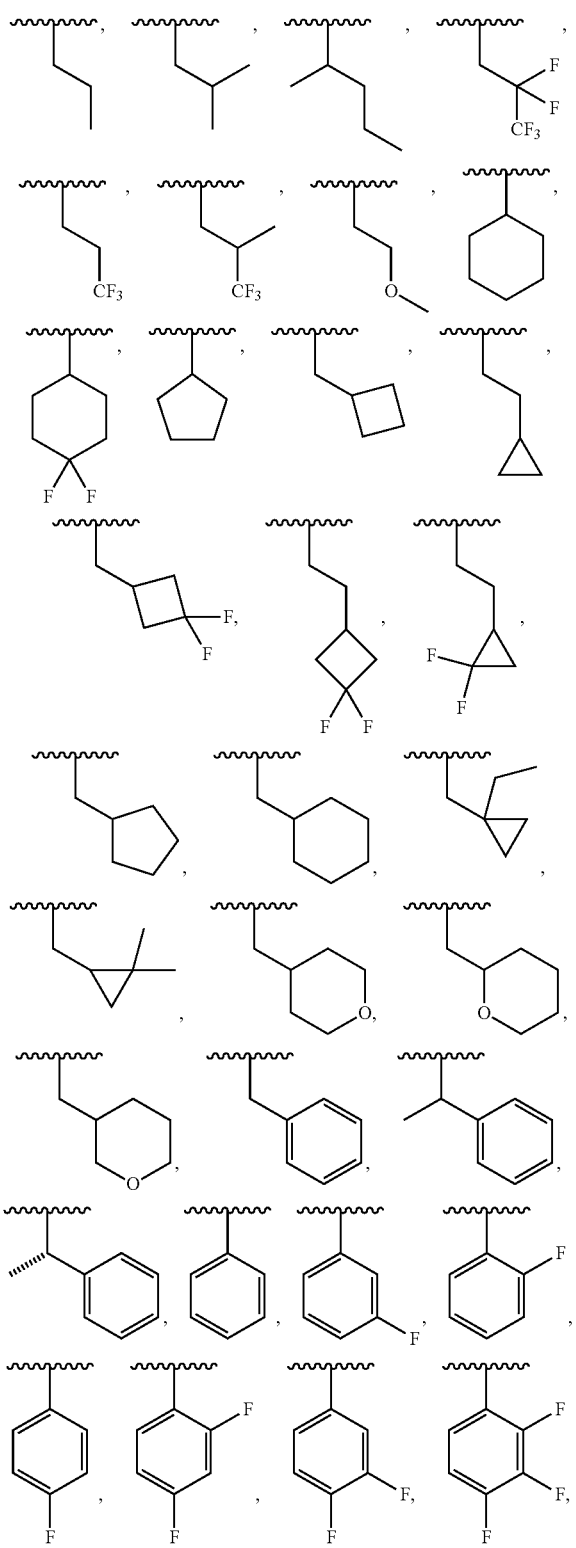

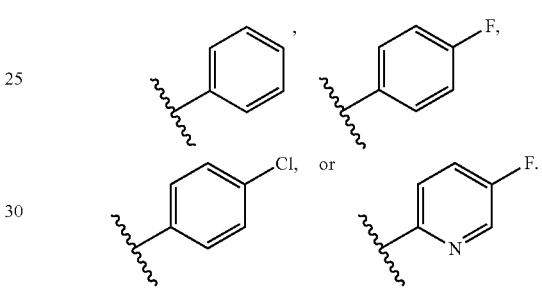

In one class of this embodiment, R³ is methyl,

In one subclass of this class, R² is methyl or cyclopropyl. In one sub-subclass of this subclass, X is O, NH, or S.

In one sub-sub-subclass of this sub-subclass, R⁴ is hydrogen, trifluoromethyl, or cyclopropyl.

In one embodiment, R³ is methyl,

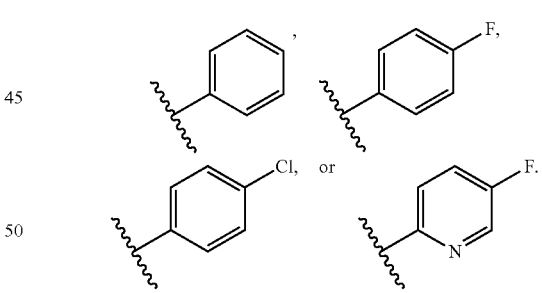

In one class of this embodiment, R² is methyl.

In one subclass of this class, X is O. In one sub-subclass of this subclass, R⁴ is hydrogen. In one sub-subclass of this subclass, R⁴ is trifluoromethyl. In one sub-subclass of this subclass, R⁴ is cyclopropyl.

In one subclass of this class, X is NH. In one sub-subclass of this subclass, R⁴ is hydrogen. In one sub-subclass of this subclass, R⁴ is trifluoromethyl. In one sub-subclass of this subclass, R⁴ is cyclopropyl.

In one subclass of this class, X is S. In one sub-subclass of this subclass, R⁴ is hydrogen. In one sub-subclass of this subclass, R⁴ is trifluoromethyl. In one sub-subclass of this subclass, R⁴ is cyclopropyl.

In one class of this embodiment, $R^2$ is cyclopropyl.

In one subclass of this class, X is O. In one sub-subclass of this subclass, $R^4$ is hydrogen. In one sub-subclass of this subclass, $R^4$ is trifluoromethyl. In one sub-subclass of this subclass, $R^4$ is cyclopropyl.

In one subclass of this class, X is NH. In one sub-subclass of this subclass, $R^4$ is hydrogen. In one sub-subclass of this subclass, $R^4$ is trifluoromethyl. In one sub-subclass of this subclass, $R^4$ is cyclopropyl.

In one subclass of this class, X is S. In one sub-subclass of this subclass, $R^4$ is hydrogen. In one sub-subclass of this subclass, $R^4$ is trifluoromethyl. In one sub-subclass of this subclass, $R^4$ is cyclopropyl.

In one embodiment, $R^3$ is methyl.

In one class of this embodiment, $R^2$ is methyl.

In one subclass of this class, X is O. In one sub-subclass of this subclass, $R^4$ is hydrogen. In one sub-subclass of this subclass, $R^4$ is trifluoromethyl. In one sub-subclass of this subclass, $R^4$ is cyclopropyl.

In one subclass of this class, X is NH. In one sub-subclass of this subclass, $R^4$ is hydrogen. In one sub-subclass of this subclass, $R^4$ is trifluoromethyl. In one sub-subclass of this subclass, $R^4$ is cyclopropyl.

In one subclass of this class, X is S. In one sub-subclass of this subclass, $R^4$ is hydrogen. In one sub-subclass of this subclass, $R^4$ is trifluoromethyl. In one sub-subclass of this subclass, $R^4$ is cyclopropyl.

In one class of this embodiment, $R^2$ is cyclopropyl.

In one subclass of this class, X is O. In one sub-subclass of this subclass, $R^4$ is hydrogen. In one sub-subclass of this subclass, $R^4$ is trifluoromethyl. In one sub-subclass of this subclass, $R^4$ is cyclopropyl.

In one subclass of this class, X is NH. In one sub-subclass of this subclass, $R^4$ is hydrogen. In one sub-subclass of this subclass, $R^4$ is trifluoromethyl. In one sub-subclass of this subclass, $R^4$ is cyclopropyl.

In one subclass of this class, X is S. In one sub-subclass of this subclass, $R^4$ is hydrogen. In one sub-subclass of this subclass, $R^4$ is trifluoromethyl. In one sub-subclass of this subclass, $R^4$ is cyclopropyl.

In one embodiment, $R^3$ is

[structure: phenyl group with wavy bond]

In one class of this embodiment, $R^2$ is methyl.

In one subclass of this class, X is O. In one sub-subclass of this subclass, $R^4$ is hydrogen. In one sub-subclass of this subclass, $R^4$ is trifluoromethyl. In one sub-subclass of this subclass, $R^4$ is cyclopropyl.

In one subclass of this class, X is NH. In one sub-subclass of this subclass, $R^4$ is hydrogen. In one sub-subclass of this subclass, $R^4$ is trifluoromethyl. In one sub-subclass of this subclass, $R^4$ is cyclopropyl.

In one subclass of this class, X is S. In one sub-subclass of this subclass, $R^4$ is hydrogen. In one sub-subclass of this subclass, $R^4$ is trifluoromethyl. In one sub-subclass of this subclass, $R^4$ is cyclopropyl.

In one class of this embodiment, $R^2$ is cyclopropyl.

In one subclass of this class, X is O. In one sub-subclass of this subclass, $R^4$ is hydrogen. In one sub-subclass of this subclass, $R^4$ is trifluoromethyl. In one sub-subclass of this subclass, $R^4$ is cyclopropyl.

In one subclass of this class, X is NH. In one sub-subclass of this subclass, $R^4$ is hydrogen. In one sub-subclass of this subclass, $R^4$ is trifluoromethyl. In one sub-subclass of this subclass, $R^4$ is cyclopropyl.

In one subclass of this class, X is S. In one sub-subclass of this subclass, $R^4$ is hydrogen. In one sub-subclass of this subclass, $R^4$ is trifluoromethyl. In one sub-subclass of this subclass, $R^4$ is cyclopropyl.

In one embodiment, $R^3$ is

[structure: 4-fluorophenyl group with wavy bond]

In one class of this embodiment, $R^2$ is methyl.

In one subclass of this class, X is O. In one sub-subclass of this subclass, $R^4$ is hydrogen. In one sub-subclass of this subclass, $R^4$ is trifluoromethyl. In one sub-subclass of this subclass, $R^4$ is cyclopropyl.

In one subclass of this class, X is NH. In one sub-subclass of this subclass, $R^4$ is hydrogen. In one sub-subclass of this subclass, $R^4$ is trifluoromethyl. In one sub-subclass of this subclass, $R^4$ is cyclopropyl.

In one subclass of this class, X is S. In one sub-subclass of this subclass, $R^4$ is hydrogen. In one sub-subclass of this subclass, $R^4$ is trifluoromethyl. In one sub-subclass of this subclass, $R^4$ is cyclopropyl.

In one class of this embodiment, $R^2$ is cyclopropyl.

In one subclass of this class, X is O. In one sub-subclass of this subclass, $R^4$ is hydrogen. In one sub-subclass of this subclass, $R^4$ is trifluoromethyl. In one sub-subclass of this subclass, $R^4$ is cyclopropyl.

In one subclass of this class, X is NH. In one sub-subclass of this subclass, $R^4$ is hydrogen. In one sub-subclass of this subclass, $R^4$ is trifluoromethyl. In one sub-subclass of this subclass, $R^4$ is cyclopropyl.

In one subclass of this class, X is S. In one sub-subclass of this subclass, $R^4$ is hydrogen. In one sub-subclass of this subclass, $R^4$ is trifluoromethyl. In one sub-subclass of this subclass, $R^4$ is cyclopropyl.

In one embodiment, $R^3$ is

[structure: 4-chlorophenyl group with wavy bond]

In one class of this embodiment, $R^2$ is methyl.

In one subclass of this class, X is O. In one sub-subclass of this subclass, $R^4$ is hydrogen. In one sub-subclass of this subclass, $R^4$ is trifluoromethyl. In one sub-subclass of this subclass, $R^4$ is cyclopropyl.

In one subclass of this class, X is NH. In one sub-subclass of this subclass, $R^4$ is hydrogen. In one sub-subclass of this subclass, $R^4$ is trifluoromethyl. In one sub-subclass of this subclass, $R^4$ is cyclopropyl.

In one subclass of this class, X is S. In one sub-subclass of this subclass, $R^4$ is hydrogen. In one sub-subclass of this subclass, $R^4$ is trifluoromethyl. In one sub-subclass of this subclass, $R^4$ is cyclopropyl.

In one class of this embodiment, R² is cyclopropyl.

In one subclass of this class, X is O. In one sub-subclass of this subclass, R⁴ is hydrogen. In one sub-subclass of this subclass, R⁴ is trifluoromethyl. In one sub-subclass of this subclass, R⁴ is cyclopropyl.

In one subclass of this class, X is NH. In one sub-subclass of this subclass, R⁴ is hydrogen. In one sub-subclass of this subclass, R⁴ is trifluoromethyl. In one sub-subclass of this subclass, R⁴ is cyclopropyl.

In one subclass of this class, X is S. In one sub-subclass of this subclass, R⁴ is hydrogen. In one sub-subclass of this subclass, R⁴ is trifluoromethyl. In one sub-subclass of this subclass, R⁴ is cyclopropyl.

In one embodiment, R³ is

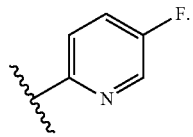 [SMILES: *c1ccc(F)cn1]

In one class of this embodiment, R² is methyl.

In one subclass of this class, X is O. In one sub-subclass of this subclass, R⁴ is hydrogen.

In one subclass of this class, X is NH. In one sub-subclass of this subclass, R⁴ is hydrogen. In one sub-subclass of this subclass, R⁴ is trifluoromethyl. In one sub-subclass of this subclass, R⁴ is cyclopropyl.

In one subclass of this class, X is S. In one sub-subclass of this subclass, R⁴ is hydrogen. In one sub-subclass of this subclass, R⁴ is trifluoromethyl. In one sub-subclass of this subclass, R⁴ is cyclopropyl.

In one class of this embodiment, R² is cyclopropyl.

In one subclass of this class, X is O. In one sub-subclass of this subclass, R⁴ is hydrogen. In one sub-subclass of this subclass, R⁴ is trifluoromethyl. In one sub-subclass of this subclass, R⁴ is cyclopropyl.

In one subclass of this class, X is NH. In one sub-subclass of this subclass, R⁴ is hydrogen. In one sub-subclass of this subclass, R⁴ is trifluoromethyl. In one sub-subclass of this subclass, R⁴ is cyclopropyl.

In one subclass of this class, X is S. In one sub-subclass of this subclass, R⁴ is hydrogen. In one sub-subclass of this subclass, R⁴ is trifluoromethyl. In one sub-subclass of this subclass, R⁴ is cyclopropyl.

In one embodiment, R² is methyl or cyclopropyl.

In one subclass of this class, X is O. In one sub-subclass of this subclass, R⁴ is hydrogen. In one sub-subclass of this subclass, R⁴ is trifluoromethyl. In one sub-subclass of this subclass, R⁴ is cyclopropyl.

In one subclass of this class, X is NH. In one sub-subclass of this subclass, R⁴ is hydrogen. In one sub-subclass of this subclass, R⁴ is trifluoromethyl. In one sub-subclass of this subclass, R⁴ is cyclopropyl.

In one subclass of this class, X is S. In one sub-subclass of this subclass, R⁴ is hydrogen. In one sub-subclass of this subclass, R⁴ is trifluoromethyl. In one sub-subclass of this subclass, R⁴ is cyclopropyl.

In one embodiment of this invention are compounds of Formula I, wherein the compounds exist as S and R enantiomers with respect to C*. In one class of this embodiment, the compounds of Formula I exist as an S enantiomer with respect to C*. In one class of this embodiment, the compounds of Formula I exist as an R enantiomer with respect to C*.

All structural Formulas, embodiments and classes thereof described herein include the pharmaceutically acceptable salts of the compounds defined therein. Reference to the compounds of structural Formula I includes the compounds of other generic structural Formulas and embodiments that fall within the scope of Formula I, including but not limited to Formula Ia to I-d.

"Alkyl", as well as other groups having the prefix "alk", such as alkoxy, and the like, means carbon chains which may be linear or branched, or combinations thereof, containing the indicated number of carbon atoms. If no number is specified, 1-6 carbon atoms are intended for linear and 3-7 carbon atoms for branched alkyl groups. Examples of alkyl groups include methyl, ethyl, propyl, isopropyl, butyl, sec- and tert-butyl, pentyl, hexyl, heptyl, octyl, nonyl and the like.

"Alkoxy" and "alkyl-O—" are used interchangeably and refer to an alkyl group linked to oxygen.

"Aryl" means phenyl or naphthyl.

"Haloalkyl" include mono-substituted as well as multiple halo substituted alkyl groups, up to perhalo substituted alkyl. For example, halomethyl, 1,1-difluoroethyl, trifluoromethyl or 1,1,1,2,2-pentafluorobutyl are included.

"Cycloalkyl" means a saturated cyclic hydrocarbon radical having the number of carbon atoms designated if no number of atoms is specified, 3-7 carbon atoms are intended, forming 1-3 carbocyclic rings that are fused. "Cycloalkyl" also includes monocyclic rings fused to an aryl group in which the point of attachment is on the nonaromatic portion. Examples of cycloalkyl include cyclopropyl, cyclobutyl, cyclopentyl, cyclohexyl, cycloheptyl, tetrahydronaphthyl, decahydronaphthyl, indanyl and the like.

"Heterocyclyl" "heterocycle" or "heterocyclic" refers to nonaromatic cyclic ring structures in which one or more atoms in the ring, the heteroatom(s), is an element other than carbon. Heterocyclyl groups can have one or more unsaturated bonds. Heteroatoms are typically O, S or N atoms. Examples of heterocyclyl groups include: piperidine, piperazinyl, morpholinyl, pyrrolidinyl, tetrahydrofuranyl, azetidinyl, oxiranyl, or aziridinyl, and the like.

"Heteroaryl" refers to aromatic cyclic ring structures in which one or more atoms in the ring, the heteroatoms(s), is an element other than carbon. Heteroatoms are typically O, S, or N atoms. Examples of heteroaromatic groups include: pyridinyl, pyrimidinyl, pyrrolyl, pyridazinyl, isoxazolyl, indolyl, or imidazolyl.

"Halogen" (or "halo") unless otherwise indicated, includes fluorine (fluoro), chlorine (chloro), bromine (bromo) and iodine (iodo). In one embodiment, halo is fluoro (—F) or chloro (—Cl).

When any variable (e.g., R¹, R², etc.) occurs more than one time in any constituent or in Formula I or other generic Formulae herein, its definition on each occurrence is independent of its definition at every other occurrence. Combinations of substituents and/or variables are permissible only if such combinations result in stable compounds. In choosing compounds of the present invention, one of ordinary skill in the art will recognize that the various substituents, i.e., R¹, R², etc., are to be chosen in conformity with well-known principles of chemical structure connectivity and stability. Unless expressly stated to the contrary, substitution by a named substituent is permitted on any atom in a ring (e.g., aryl, a heteroaryl ring, or a saturated heterocyclic ring) provided such ring substitution is chemically allowed and results in a stable compound. A "stable" compound is a compound which can be prepared and isolated and whose structure and properties remain or can be caused to remain essentially unchanged for a period of time sufficient to allow use of the compound for the purposes described herein (e.g., therapeutic or prophylactic administration to a subject).

The term "substituted" shall be deemed to include multiple degrees of substitution by a named substituent. Where multiple substituent moieties are disclosed or claimed, the substituted compound can be independently substituted by one or more of the disclosed or claimed substituent moieties, singly or plurally. By independently substituted, it is meant that the (two or more) substituents can be the same or different.

Unless expressly depicted or described otherwise, variables depicted in a structural formula with a "floating" bond are permitted on any available carbon atom in the ring to which the variable is attached. When a moiety is noted as being "optionally substituted" in Formula I or any embodiment thereof, it means that Formula I or the embodiment thereof encompasses compounds that contain the noted substituent (or substituents) on the moiety and also compounds that do not contain the noted substituent (or substituents) on the moiety.

Compounds of structural Formulas I may contain one or more asymmetric centers and can thus occur as racemates and racemic mixtures, single enantiomers, diastereoisomeric mixtures and individual diastereoisomers. Centers of asymmetry that are present in the compounds of Formula I can all independently of one another have S configuration or R configuration. The compounds of this invention include all possible enantiomers and diastereomers and mixtures of two or more stereoisomers, for example mixtures of enantiomers and/or diastereomers, in all ratios. Thus, enantiomers are a subject of the invention in enantiomerically pure form, both as levorotatory and as dextrorotatory antipodes, in the form of racemates and in the form of mixtures of the two enantiomers in all ratios. In the case of a cis/trans isomerism the invention includes both the cis form and the trans form as well as mixtures of these forms in all ratios. The present invention is meant to comprehend all such stereo-isomeric forms of the compounds of structural Formula I.

Compounds of structural Formula I may be separated into their individual diastereoisomers by, for example, fractional crystallization from a suitable solvent, for example methanol or ethyl acetate or a mixture thereof, or via chiral chromatography using an optically active stationary phase. Absolute stereochemistry may be determined by X-ray crystallography of crystalline products or crystalline intermediates which are derivatized, if necessary, with a reagent containing an asymmetric center of known absolute configuration. Alternatively, any stereoisomer or isomers of a compound of Formula I may be obtained by stereospecific synthesis using optically pure starting materials or reagents of known absolute configuration.

If desired, racemic mixtures of the compounds may be separated so that the individual enantiomers are isolated. The separation can be carried out by methods well known in the art, such as the coupling of a racemic mixture of compounds to an enantiomerically pure compound to form a diastereoisomeric mixture, followed by separation of the individual diastereoisomers by standard methods, such as fractional crystallization or chromatography. The coupling reaction is often the formation of salts using an enantiomerically pure acid or base. The diasteromeric derivatives may then be converted to the pure enantiomers by cleavage of the added chiral residue. The racemic mixture of the compounds can also be separated directly by chromatographic methods utilizing chiral stationary phases, which methods are well known in the art.

For compounds of Formula I described herein which contain olefinic double bonds, unless specified otherwise, they are meant to include both E and Z geometric isomers.

Some of the compounds described herein may exist as tautomers which have different points of attachment of hydrogen accompanied by one or more double bond shifts. For example, a ketone and its enol form are keto-enol tautomers. The individual tautomers as well as mixtures thereof are encompassed with compounds of Formula I of the present invention.

In the compounds of structural Formula I, the atoms may exhibit their natural isotopic abundances, or one or more of the atoms may be artificially enriched in a particular isotope having the same atomic number, but an atomic mass or mass number different from the atomic mass or mass number predominantly found in nature. The present invention as described and claimed herein is meant to include all suitable isotopic variations of the compounds of structural Formula I and embodiments thereof. For example, different isotopic forms of hydrogen (H) include protium ($^1$H) and deuterium ($^2$H, also denoted herein as D). Protium is the predominant hydrogen isotope found in nature. Enriching for deuterium may afford certain therapeutic advantages, such as increasing in vivo half-life or reducing dosage requirements, or may provide a compound useful as a standard for characterization of biological samples. Isotopically-enriched compounds within structural Formula I, can be prepared without undue experimentation by conventional techniques well known to those skilled in the art or by processes analogous to those described in the Schemes and Examples herein using appropriate isotopically-enriched reagents and/or intermediates.

The term "pharmaceutically acceptable salts" refers to salts prepared from pharmaceutically acceptable non-toxic bases or acids. When the compound of the present invention is acidic, its corresponding salt can be conveniently prepared from pharmaceutically acceptable non-toxic bases, including inorganic bases and organic bases. Salts derived from such inorganic bases include aluminum, ammonium, calcium, copper (ic and ous), ferric, ferrous, lithium, magnesium, manganese (ic and ous), potassium, sodium, zinc and the like salts. Preferred are the ammonium, calcium, magnesium, potassium and sodium salts. Salts prepared from pharmaceutically acceptable organic non-toxic bases include salts of primary, secondary, and tertiary amines derived from both naturally occurring and synthetic sources. Pharmaceutically acceptable organic non-toxic bases from which salts can be formed include, for example, arginine, betaine, caffeine, choline, N,N'-dibenzylethylenediamine, diethylamine, 2-diethylaminoethanol, 2-dimethylaminoethanol, ethanolamine, ethylenediamine, N-ethylmorpholine, N-ethylpiperidine, glucamine, glucosamine, histidine, hydrabamine, isopropylamine, dicyclohexylamine, lysine, methylglucamine, morpholine, piperazine, piperidine, polyamine resins, procaine, purines, theobromine, triethylamine, trimethylamine, tripropylamine, tromethamine and the like.

When the compound of the present invention is basic, its corresponding salt can be conveniently prepared from pharmaceutically acceptable non-toxic inorganic and organic acids. Such acids include, for example, acetic, benzenesulfonic, benzoic, camphorsulfonic, citric, ethanesulfonic, fumaric, gluconic, glutamic, hydrobromic, hydrochloric, isethionic, lactic, maleic, malic, mandelic, methanesulfonic, mucic, nitric, pamoic, pantothenic, phosphoric, succinic, sulfuric, tartaric, p-toluenesulfonic acid and the like. Preferred are citric, hydrobromic, hydrochloric, maleic, phosphoric, sulfuric, and tartaric acids. If the compounds of Formula I simultaneously contain acidic and basic groups in the molecule the invention also includes, in addition to the salt forms mentioned, inner salts or betaines (zwitterions). Salts can be obtained from the compounds of Formula I by customary methods which are known to the person skilled in the art, for example by combination with an organic or inorganic acid or base in a solvent or dispersant, or by anion exchange or cation exchange from other salts. The present invention also includes all salts of the compounds of Formula I which, owing to low physiological compatibility, are not directly suitable for use in pharmaceuticals but which can be used, for example, as intermediates for chemical reactions or for the preparation of pharmaceutically acceptable salts.

Furthermore, compounds of the present invention may exist in amorphous form and/or one or more crystalline forms, and as such all amorphous and crystalline forms and mixtures thereof of the compounds of Formula I, including the Examples, are intended to be included within the scope of the present invention. In addition, some of the compounds of the instant invention may form solvates with water (i.e., a hydrate) or common organic solvents such as but not limited to ethyl acetate. Such solvates and hydrates, particularly the pharmaceutically acceptable solvates and hydrates, of the instant compounds are likewise encompassed within the scope of this invention, along with un-solvated and anhydrous forms.

Any pharmaceutically acceptable pro-drug modification of a compound of this invention which results in conversion in vivo to a compound within the scope of this invention is also within the scope of this invention. For example, esters can optionally be made by esterification of an available carboxylic acid (—COOH) group or by formation of an ester on an available hydroxy group in a compound. Similarly, labile amides can be made. Pharmaceutically acceptable esters or amides of the compounds of this invention may be prepared to act as pro-drugs which can be hydrolyzed back to an acid (or —COO— depending on the pH of the fluid or tissue where conversion takes place) or hydroxy form particularly in vivo and as such are encompassed within the scope of this invention. Included are those esters and acyl groups known in the art for modifying the solubility or hydrolysis characteristics for use as sustained-release or prodrug formulations. Also, in the case of a carboxylic acid (—COOH) or alcohol group being present in the compounds of the present invention, pharmaceutically acceptable esters of carboxylic acid derivatives, such as methyl, ethyl, or pivaloyloxymethyl, or acyl derivatives of alcohols, such as O-acetyl, O-pivaloyl, O-benzoyl, and O-aminoacyl, can be employed.

The present invention also relates to processes for the preparation of the compounds of Formula I which are described in the following and by which the compounds of the invention are obtainable.

The compounds of Formula I according to the invention effect an increase of cGMP concentration via the activation of the soluble guanylate cyclase (sGC), and they are therefore useful agents for the therapy and prophylaxis of disorders which are associated with a low or decreased cGMP level or which are caused thereby, or for whose therapy or prophylaxis an increase of the present cGMP level is desired. The activation of the sGC by the compounds of Formula I can be examined, for example, in the activity assay described below.

The terms "therapeutically effective (or efficacious) amount" and similar descriptions such as "an amount efficacious for treatment" are intended to mean that amount of a pharmaceutical drug that will elicit the biological or medical response of a tissue, a system, animal or human that is being sought by a researcher, veterinarian, medical doctor or other clinician. The terms "prophylactically effective (or efficacious) amount" and similar descriptions such as "an amount efficacious for prevention" are intended to mean that amount of a pharmaceutical drug that will prevent or reduce the risk of occurrence of the biological or medical event that is sought to be prevented in a tissue, a system, animal or human by a researcher, veterinarian, medical doctor or other clinician. As an example, the dosage a patient receives can be selected so as to achieve the desired reduction in blood pressure; the dosage a patient receives may also be titrated over time in order to reach a target blood pressure. The dosage regimen utilizing a compound of the instant invention is selected in accordance with a variety of factors including type, species, age, weight, sex and medical condition of the patient; the severity of the condition to be treated; the potency of the compound chosen to be administered; the route of administration; and the renal and hepatic function of the patient. A consideration of these factors is well within the purview of the ordinarily skilled clinician for the purpose of determining the therapeutically effective or prophylactically effective dosage amount needed to prevent, counter, or arrest the progress of the condition. It is understood that a specific daily dosage amount can simultaneously be both a therapeutically effective amount, e.g., for treatment of hypertension, and a prophylactically effective amount, e.g., for prevention of myocardial infarction.

Disorders and pathological conditions which are associated with a low cGMP level or in which an increase of the cGMP level is desired and for whose therapy and prophylaxis it is possible to use compounds of Formula I are, for example, cardiovascular diseases, such as endothelial dysfunction, diastolic dysfunction, atherosclerosis, hypertension, heart failure, pulmonary hypertension, which includes pulmonary arterial hypertension (PAH), stable and unstable angina pectoris, thromboses, restenoses, myocardial infarction, strokes, cardiac insufficiency, fibrosis or pulmonary hypertonia, or, for example, erectile dysfunction, asthma bronchiale, chronic kidney insufficiency and diabetes. Compounds of Formula I can additionally be used in the therapy of cirrhosis of the liver and also for improving a restricted memory performance or ability to learn.

The compounds of Formula I and their pharmaceutically acceptable salts can be administered to animals, preferably to mammals, and in particular to humans, as pharmaceuticals by themselves, in mixtures with one another or in the form of pharmaceutical compositions. The term "patient" includes animals, preferably mammals and especially humans, who use the instant active agents for the prevention or treatment of a medical condition. Administering of the drug to the patient includes both self-administration and administration to the patient by another person. The patient may be in need of, or desire, treatment for an existing disease or medical condition, or may be in need of or desire prophylactic treatment to prevent or reduce the risk of occurrence of said disease or medical condition. As used herein, a patient "in need" of treatment of an existing condition or of prophylactic treatment encompasses both a determination of need by a medical professional as well as the desire of a patient for such treatment.

A subject of the present invention therefore also are the compounds of Formula I and their pharmaceutically acceptable salts for use as pharmaceuticals, their use for activating soluble guanylate cyclase, for normalizing a disturbed cGMP balance and in particular their use in the therapy and prophylaxis of the abovementioned syndromes as well as their use for preparing medicaments for these purposes.

Furthermore, a subject of the present invention are pharmaceutical compositions which comprise as active component an effective dose of at least one compound of Formula I and/or a pharmaceutically acceptable salt thereof and a customary pharmaceutically acceptable carrier, i.e., one or more pharmaceutically acceptable carrier substances and/or additives.

Thus, a subject of the invention are, for example, said compound and its pharmaceutically acceptable salts for use as a pharmaceutical, pharmaceutical compositions which comprise as active component an effective dose of said compound and/or a pharmaceutically acceptable salt thereof and a customary pharmaceutically acceptable carrier, and the uses of said compound and/or a pharmaceutically acceptable salt thereof in the therapy or prophylaxis of the abovementioned syndromes as well as their use for preparing medicaments for these purposes.

The pharmaceutical compositions according to the invention can be administered orally, for example in the form of pills, tablets, lacquered tablets, sugar-coated tablets, granules, hard and soft gelatin capsules, aqueous, alcoholic or oily solutions, syrups, emulsions or suspensions, or rectally, for example in the form of suppositories. Administration can also be carried out parenterally, for example subcutaneously, intramuscularly or intravenously in the form of solutions for injection or infusion. Other suitable administration forms are, for example, percutaneous or topical administration, for example in the form of ointments, tinctures, sprays or transdermal therapeutic systems, or the inhalative administration in the form of nasal sprays or aerosol mixtures, or, for example, microcapsules, implants or rods. The preferred administration form depends, for example, on the disease to be treated and on its severity.

The amount of active compound of Formula I and/or its pharmaceutically acceptable salts in the pharmaceutical composition normally is from 0.1 to 200 mg, preferably from 1 to 200 mg, per dose, but depending on the type of the pharmaceutical composition it can also be higher. The pharmaceutical compositions usually comprise 0.5 to 90 percent by weight of the compounds of Formula I and/or their pharmaceutically acceptable salts. The preparation of the pharmaceutical compositions can be carried out in a manner known per se. For this purpose, one or more compounds of Formula I and/or their pharmaceutically acceptable salts, together with one or more solid or liquid pharmaceutical carrier substances and/or additives (or auxiliary substances) and, if desired, in combination with other pharmaceutically active compounds having therapeutic or prophylactic action, are brought into a suitable administration form or dosage form which can then be used as a pharmaceutical in human or veterinary medicine.

For the production of pills, tablets, sugar-coated tablets and hard gelatin capsules, it is possible to use, for example, lactose, starch, for example maize starch, or starch derivatives, talc, stearic acid or its salts, etc. Carriers for soft gelatin capsules and suppositories are, for example, fats, waxes, semisolid and liquid polyols, natural or hardened oils, etc. Suitable carriers for the preparation of solutions, for example of solutions for injection, or of emulsions or syrups are, for example, water, physiologically sodium chloride solution, alcohols such as ethanol, glycerol, polyols, sucrose, invert sugar, glucose, mannitol, vegetable oils, etc.

It is also possible to lyophilize the compounds of Formulas I and their pharmaceutically acceptable salts and to use the resulting lyophilisates, for example, for preparing preparations for injection or infusion. Suitable carriers for microcapsules, implants or rods are, for example, copolymers of glycolic acid and lactic acid.

Besides the active compounds and carriers, the pharmaceutical compositions can also contain customary additives, for example fillers, disintegrants, binders, lubricants, wetting agents, stabilizers, emulsifiers, dispersants, preservatives, sweeteners, colorants, flavorings, aromatizers, thickeners, diluents, buffer substances, solvents, solubilizers, agents for achieving a depot effect, salts for altering the osmotic pressure, coating agents or antioxidants.

The dosage of the active compound of Formula I and/or of a pharmaceutically acceptable salt thereof to be administered depends on the individual case and is, as is customary, to be adapted to the individual circumstances to achieve an optimum effect. Thus, it depends on the nature and the severity of the disorder to be treated, and also on the sex, age, weight and individual responsiveness of the human or animal to be treated, on the efficacy and duration of action of the compounds used, on whether the therapy is acute or chronic or prophylactic, or on whether other active compounds are administered in addition to compounds of Formula I. In general, a daily dose of approximately 0.01 to 100 mg/kg, preferably 0.01 to 10 mg/kg, in particular 0.3 to 5 mg/kg (in each case mg per kg of body weight) is appropriate for administration to an adult weighing approximately 75 kg in order to obtain the desired results. The daily dose can be administered in a single dose or, in particular when larger amounts are administered, be divided into several, for example two, three or four individual doses. In some cases, depending on the individual response, it may be necessary to deviate upwards or downwards from the given daily dose. A single daily dose is preferred.

The compounds of Formula I activate soluble guanylate cyclase. On account of this property, apart from use as pharmaceutically active compounds in human medicine and veterinary medicine, they can also be employed as a scientific tool or as an aid for biochemical investigations in which such an effect on soluble guanylate cyclase is intended, and also for diagnostic purposes, for example in the in vitro diagnosis of cell samples or tissue samples. The compounds of Formula I and salts thereof can furthermore be employed, as already mentioned above, as intermediates for the preparation of other pharmaceutically active compounds.

One or more additional pharmacologically active agents may be administered in combination with a compound of Formula I. An additional active agent (or agents) is intended to mean a pharmaceutically active agent (or agents) that is active in the body, including pro-drugs that convert to pharmaceutically active form after administration, which are different from the compound of Formula I, and also includes free-acid, free-base and pharmaceutically acceptable salts of said additional active agents. Generally, any suitable additional active agent or agents, including but not limited to antihypertensive agents, anti-atherosclerotic agents such as a lipid modifying compound, anti-diabetic agents and/or anti-obesity agents may be used in any combination with the compound of Formula I in a single dosage formulation (a fixed dose drug combination), or may be administered to the patient in one or more separate dosage formulations which allows for concurrent or sequential administration of the active agents (co-administration of the separate active agents). Examples of additional active agents which may be employed include but are not limited to angiotensin converting enzyme inhibitors (e.g. alacepril, benazepril, captopril, ceronapril, cilazapril, delapril, enalapril, enalaprilat, fosinopril, imidapril, lisinopril, moveltipril, perindopril, quinapril, ramipril, spirapril, temocapril, or trandolapril), angiotensin II receptor antagonists (e.g., losartan i.e., COZAAR®, valsartan, candesartan, olmesartan, telmesartan and any of these drugs used in combination with hydrochlorothiazide such as HYZAAR®); neutral endopeptidase inhibitors (e.g., thiorphan and phosphoramidon), aldosterone antagonists, aldosterone synthase inhibitors, renin inhibitors (e.g. urea derivatives of di- and tri-peptides (See U.S. Pat. No. 5,116,835), amino acids and derivatives (U.S. Pat. Nos. 5,095,119 and 5,104,869), amino acid chains linked by non-peptidic bonds (U.S. Pat. No. 5,114,937), di- and tri-peptide derivatives (U.S. Pat. No. 5,106,835), peptidyl amino diols (U.S. Pat. Nos. 5,063,208 and 4,845,079) and peptidyl beta-aminoacyl aminodiol carbamates (U.S. Pat. No. 5,089,471); also, a variety of other peptide analogs as disclosed in the following U.S. Pat. Nos. 5,071,837; 5,064,965; 5,063,207; 5,036,054; 5,036,053; 5,034,512 and 4,894,437, and small molecule renin inhibitors (including diol sulfonamides and sulfinyls (U.S. Pat. No. 5,098,924), N-morpholino derivatives (U.S. Pat. No. 5,055,466), N-heterocyclic alcohols (U.S. Pat. No. 4,885,292) and pyrolimidazolones (U.S. Pat. No. 5,075,451); also, pepstatin derivatives (U.S. Pat. No. 4,980,283) and fluoro- and chloro-derivatives of statone-containing peptides (U.S. Pat. No. 5,066,643), enalkrein, RO 42-5892, A 65317, CP 80794, ES 1005, ES 8891, SQ 34017, aliskiren (2(S),4(S),5(S),7(S)—N-(2-carbamoyl-2-methylpropyl)-5-amino-4-hydroxy-2,7-diisopropyl-8-[4-methoxy-3-(3-methoxypropoxy)-phenyl]-octanamid hemifumarate) SPP600, SPP630 and SPP635), endothelin receptor antagonists, phosphodiesterase-5 inhibitors (e.g. sildenafil, tadalfil and vardenafil), vasodilators, calcium channel blockers (e.g., amlodipine, nifedipine, veraparmil, diltiazem, gallopamil, niludipine, nimodipins, nicardipine), potassium channel activators (e.g., nicorandil, pinacidil, cromakalim, minoxidil, aprilkalim, loprazolam), diuretics (e.g., hydrochlorothiazide), sympatholitics, beta-adrenergic blocking drugs (e.g., propranolol, atenolol, bisoprolol, carvedilol, metoprolol, or metoprolol tartate), alpha adrenergic blocking drugs (e.g., doxazocin, prazocin or alpha methyldopa) central alpha adrenergic agonists, peripheral vasodilators (e.g. hydralazine); lipid lowering agents e.g., HMG-CoA reductase inhibitors such as simvastatin and lovastatin which are marketed as ZOCOR® and MEVACOR® in lactone pro-drug form and function as inhibitors after administration, and pharmaceutically acceptable salts of dihydroxy open ring acid HMG-CoA reductase inhibitors such as atorvastatin (particularly the calcium salt sold in LIPITOR®), rosuvastatin (particularly the calcium salt sold in CRESTOR®), pravastatin (particularly the sodium salt sold in PRAVACHOL®), and fluvastatin (particularly the sodium salt sold in LESCOL®); a cholesterol absorption inhibitor such as ezetimibe (ZETIA®) and ezetimibe in combination with any other lipid lowering agents such as the HMG-CoA reductase inhibitors noted above and particularly with simvastatin (VYTORIN®) or with atorvastatin calcium; niacin in immediate-release or controlled release forms, and/or with an HMG-CoA reductase inhibitor; niacin receptor agonists such as acipimox and acifran, as well as niacin receptor partial agonists; metabolic altering agents including insulin and insulin mimetics (e.g., insulin degludec, insulin glargine, insulin lispro), dipeptidyl peptidase-IV (DPP-4) inhibitors (e.g., sitagliptin, alogliptin, omarigliptin, linagliptin, vildagliptin); insulin sensitizers, including (i) PPARγ agonists, such as the glitazones (e.g. pioglitazone, AMG 131, MBX2044, mitoglitazone, lobeglitazone, IDR-105, rosiglitazone, and balaglitazone), and other PPAR ligands, including (1) PPARα/γ dual agonists (e.g., ZYH2, ZYH1, GFT505, chiglitazar, muraglitazar, aleglitazar, sodelglitazar, and naveglitazar); (2) PPARα agonists such as fenofibric acid derivatives (e.g., gemfibrozil, clofibrate, ciprofibrate, fenofibrate, bezafibrate), (3) selective PPARγ modulators (SPPARγM's), (e.g., such as those disclosed in WO 02/060388, WO 02/08188, WO 2004/019869, WO 2004/020409, WO 2004/020408, and WO 2004/066963); and (4) PPARγ partial agonists; (ii) biguanides, such as metformin and its pharmaceutically acceptable salts, in particular, metformin hydrochloride, and extended-release formulations thereof, such as Glumetza™, Fortamet™, and GlucophageXR™; and (iii) protein tyrosine phosphatase-1B (PTP-1B) inhibitors (e.g., ISIS-113715 and TTP814); insulin or insulin analogs (e.g., insulin detemir, insulin glulisine, insulin degludec, insulin glargine, insulin lispro and inhalable formulations of each); leptin and leptin derivatives and agonists; amylin and amylin analogs (e.g., pramlintide); sulfonylurea and non-sulfonylurea insulin secretagogues (e.g., tolbutamide, glyburide, glipizide, glimepiride, mitiglinide, meglitinides, nateglinide and repaglinide); α-glucosidase inhibitors (e.g., acarbose, voglibose and miglitol); glucagon receptor antagonists (e.g., MK-3577, MK-0893, LY-2409021 and KT6-971); incretin mimetics, such as GLP-1, GLP-1 analogs, derivatives, and mimetics; and GLP-1 receptor agonists (e.g., dulaglutide, semaglutide, albiglutide, exenatide, liraglutide, lixisenatide, taspoglutide, CJC-1131, and BIM-51077, including intranasal, transdermal, and once-weekly formulations thereof); LDL cholesterol lowering agents such as (i) HMG-CoA reductase inhibitors (e.g., simvastatin, lovastatin, pravastatin, cerivastatin, fluvastatin, atorvastatin, and rosuvastatin), (ii) bile acid sequestering agents (e.g., colestilan, colestimide, colesevalam hydrochloride, colestipol, cholestyramine, and dialkylaminoalkyl derivatives of a cross-linked dextran), (iii) inhibitors of cholesterol absorption, (e.g., ezetimibe), and (iv) acyl CoA:cholesterol acyltransferase inhibitors, (e.g., avasimibe); HDL-raising drugs, (e.g., niacin and nicotinic acid receptor agonists, and extended-release versions thereof; antiobesity compounds; agents intended for use in inflammatory conditions, such as aspirin, non-steroidal anti-inflammatory drugs or NSAIDs, glucocorticoids, and selective cyclooxygenase-2 or COX-2 inhibitors; glucokinase activators (GKAs) (e.g., AZD6370); inhibitors of 11β-hydroxysteroid dehydrogenase type 1, (e.g., such as those disclosed in U.S. Pat. No. 6,730,690, and LY-2523199); CETP inhibitors (e.g., anacetrapib, and torcetrapib); inhibitors of fructose 1,6-bisphosphatase, (e.g., such as those disclosed in U.S. Pat. Nos. 6,054,587; 6,110,903; 6,284,748; 6,399,782; and 6,489,476); inhibitors of acetyl CoA carboxylase-1 or 2 (ACC1 or ACC2); AMP-activated Protein Kinase (AMPK) activators; other agonists of the G-protein-coupled receptors: (i) GPR-109, (ii) GPR-119 (e.g., MBX2982 and PSN821), and (iii) GPR-40; SSTR3 antagonists (e.g., such as those disclosed in WO 2009/001836); neuromedin U receptor agonists (e.g., such as those disclosed in WO 2009/042053, including, but not limited to, neuromedin S (NMS)); SCD modulators; GPR-105 antagonists (e.g., such as those disclosed in WO 2009/000087); SGLT inhibitors (e.g., ASP1941, SGLT-3, empagliflozin, dapagliflozin, canagliflozin, BI-10773, ertugliflozin, remogloflozin, TS-071, tofogliflozin, ipragliflozin, and LX-4211); inhibitors of acyl coenzyme A:diacylglycerol acyltransferase 1 and 2 (DGAT-1 and DGAT-2); inhibitors of fatty acid synthase; inhibitors of acyl coenzyme A:monoacylglycerol acyltransferase 1 and 2 (MGAT-1 and MGAT-2); agonists of the TGR5 receptor (also known as GPBAR1, BG37, GPCR19, GPR131, and M-BAR); ileal bile acid transporter inhibitors; PACAP, PACAP mimetics, and PACAP receptor 3 agonists; PPAR agonists; protein tyrosine phosphatase-1B (PTP-1B) inhibitors; IL-1b antibodies, (e.g., XOMA052 and canakinumab); and bromocriptine mesylate and rapid-release formulations thereof; or with other drugs beneficial for the prevention or the treatment of the above-mentioned diseases including nitroprusside and diazoxide the free-acid, free-base, and pharmaceutically acceptable salt forms of the above active agents where chemically possible.

The following examples are provided so that the invention might be more fully understood. Unless otherwise indicated, the starting materials are commercially available. They should not be construed as limiting the invention in any way.

Several methods for preparing the compounds of this invention are described in the following Schemes and Examples. Starting materials and intermediates are purchased, made from known procedures, or as otherwise illustrated. Some frequently applied routes to the compounds of Formula I are also described by the Schemes as follows. In some cases the order of carrying out the steps of reaction schemes may be varied to facilitate the reaction or to avoid unwanted reaction products. The "R" and "X" groups in the Schemes correspond to the variables defined in Formula I at the same positions on the structures.

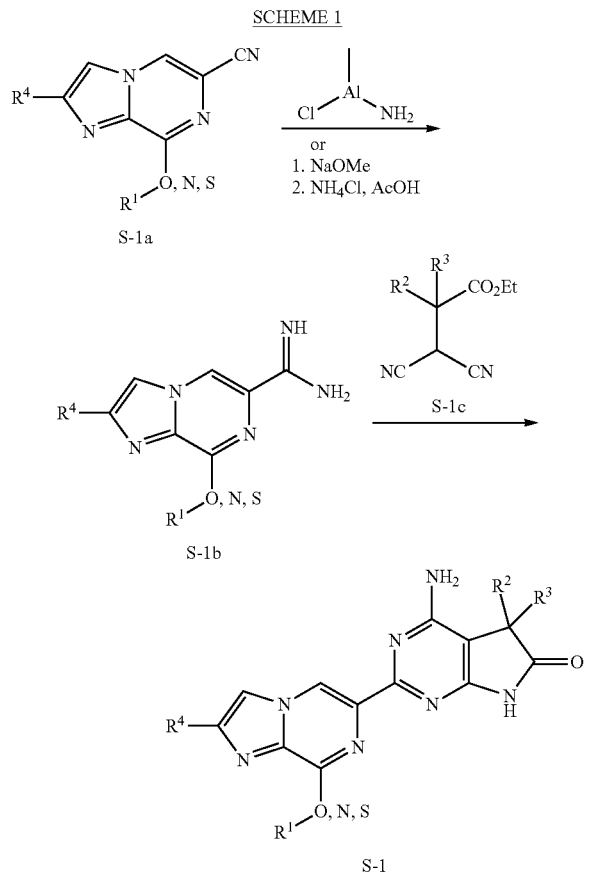

SCHEME 1

Compounds of Formula S-I can be prepared from the nitrile precursor (S-1a) as outlined in Scheme 1. Conversion of the imidazo[1,2-a]pyrazine nitrile S-1a to the amidine intermediate S-1b can be accomplished with a reagent such as amino(chloro)methylaluminum, prepared from trimethylaluminum and $NH_4Cl$, in a non-polar solvent such as toluene at elevated temperature as described by Garigipati, R. S. et al *Tetrahedron Letters* 1990, 31(14), 1969. The nitrile S-1a can also be converted to the amidine S-1b by using sodium methoxide in methanol to form the imidate which can then be transformed to the amidine S-1b using $NH_4Cl$ and AcOH as described by Pinner, A. et al, *Ber. Dtsch. Chem. Ges.* 1877, 10, 1889. Treatment of the amidine S-1b with a suitable malononitrile intermediate S-1c in an alcoholic solvent such as t-BuOH, EtOH, or MeOH, in the presence of a suitable base such as $NaHCO_3$, $KHCO_3$, or $Na_2CO_3$ at elevated temperature provides compounds with Formula S-I. The reactions in Scheme 1 may also be carried out on the corresponding ester of compound S-1a, and corresponding methyl, ethyl, or propyl esters of compound S-1c.

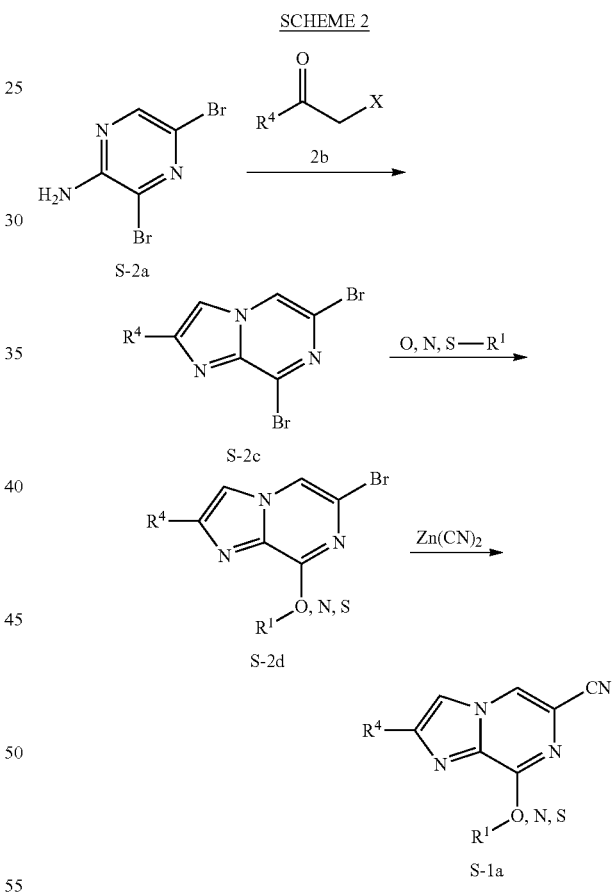

SCHEME 2

The nitrile intermediate S-1a can be prepared from commercially available 3,5-dibromopyrazin-2-amine (S-2a) as depicted in Scheme 2. 3,5-Dibromopyrazin-2-amine (2a) can be treated with a suitable alpha-haloketone reagent (S-2b) to afford the dibromo intermediate S-2c. The dibromo intermediate S-2c can be selectively displaced with an alcohol, amine, or sulfide in the presence of a base such as $Na_2CO_3$, $Cs_2CO_3$, NaH, or DIEA to give compound S-2d, which can be transformed into the nitrile intermediate S-1a using $Zn(CN)_2$ and a palladium catalyst such as $Pd(dppf)Cl_2$ at an elevated temperature.

SCHEME 3

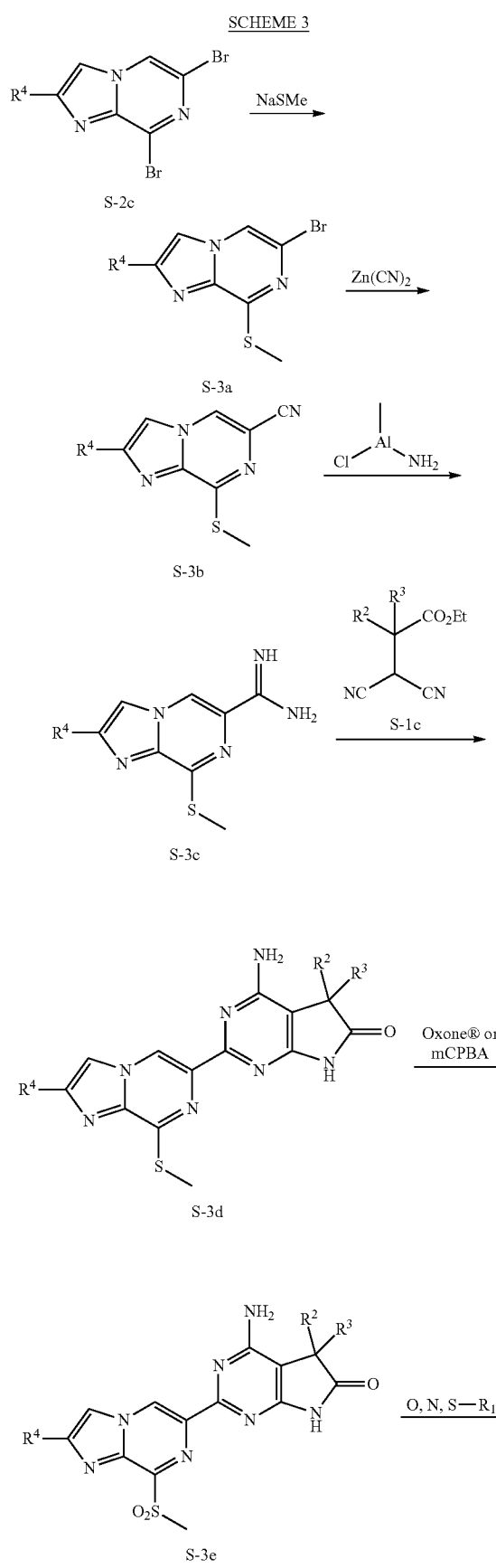

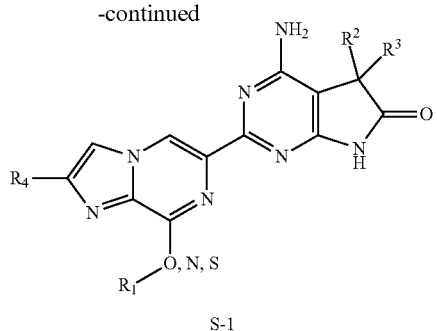

Alternatively, compounds of Formula I can be prepared as depicted in Scheme 3. The dibromo intermediate (S-2c) from Scheme 2 can be converted to the thiomethyl intermediate (S-3a) by nucleophilic displacement using sodium thiomethoxide as described by Belanger, D. B. et al *Bioorg. Med. Chem. Lett.* 2010, 20, 5170. Compound S-3b can be obtained by treatment of the intermediate 3a with a reagent such as $Zn(CN)_2$ in the presence of a suitable palladium catalyst such as $Pd(dppf)Cl_2$. The nitrile intermediate (S-3b) can be transformed to the amidine intermediate (S-3c) and subsequently cyclized with a suitable malononitrile reagent (S-1c) to afford the thiomethyl intermediate (S-3d) as similarly described in Scheme 1. Treatment of intermediate S-3d with an oxidant, such as Oxone® or m-CPBA in the presence of an acid such as sulfuric acid, can generate intermediate S-3e. Intermediate S-3e can be displaced with a suitable alcohol, amine, or thiol using a base such as $Na_2CO_3$, $Cs_2CO_3$, NaH, or Hunig's base. This transformation can also occur under neutral conditions upon microwave irradiation or thermal heating to afford compounds of Formula S-I.

SCHEME 4

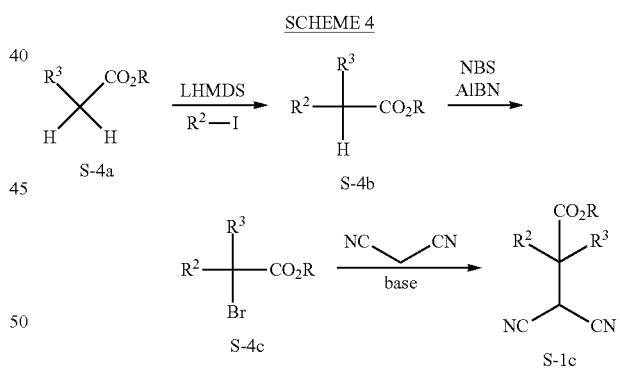

The preparation of compound 1c is outlined in Scheme 4. Deprotonation of ester S-4a using a suitable base such as LiHMDS, NaHMDS, NaH or LDA in a solvent such as THF or DMF followed by treatment with an alkyl iodide affords the intermediate S-4b. Treatment of intermediate S-4b with a suitable brominating reagent such as NBS and AIBN in a solvent such as carbon tetrachloride at refluxing temperatures affords intermediate S-4c. Intermediate S-4c can be transformed to compound S-1c by reaction with malononitrile in the presence of a suitable base such as NaH, t-BuOK, $K_2CO_3$ or DBU in a solvent such as THF or DMF at RT or at elevated temperature. The synthetic sequence depicted in Scheme 4 can also be similarly used to prepare the corresponding ethyl or propyl esters of compound S-1c.

SCHEME 5

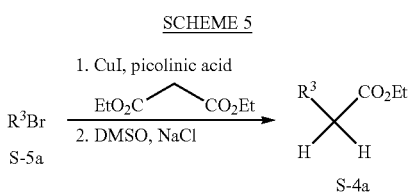

The ester (S-4a) can be prepared from the corresponding carboxylic acid by one skilled in the art. The ester (S-4a) may also be prepared by the α-arylation/heteroarylation of esters as described by Buchwald, S. L. et al *Organic Letters* 2009, 11(8), 1773; or by Shen, H. C. et al *Organic Letters* 2006, 8(7), 1447. Commercially available aryl bromides can be converted to compound S-4a (depicted as the ethyl ester) by the reaction with diethyl malonate in the presence of a suitable catalyst system such as CuI and picolinic acid, followed by decarboxylation at elevated temperature according to Scheme 5.

SCHEME 6

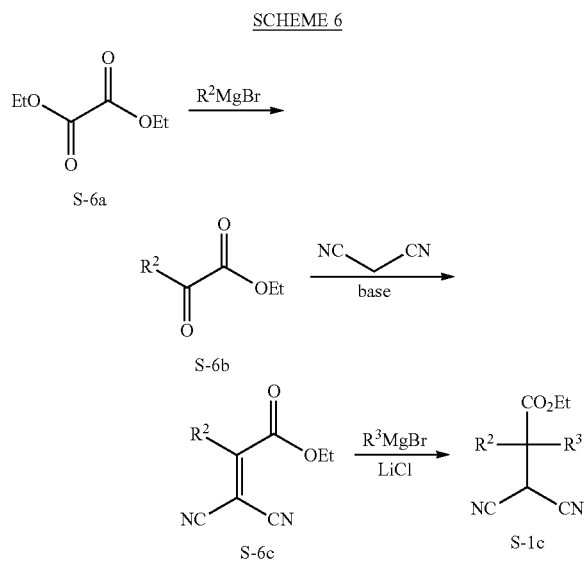

In addition to the method described in Scheme 4, intermediates S-1c, depicted as the ethyl ester, may also be prepared as shown in Scheme 6. Thus, treatment of diethyl oxalate with a suitable aryl magnesium bromide (with or without lithium chloride additive) or the lithiate of heteroaryl reagents derived via metal-halogen exchange in a suitable solvent such as THF affords compound S-6b. Treatment of compound S-6b with malononitrile and a suitable base such as piperidine in a solvent such as EtOH at elevated temperature affords compound S-6c. Compound S-6c, upon treatment with a suitable alkyl magnesium bromide (with or without lithium chloride additive) in a solvent such as THF affords compound S-1c.

Compounds of the present invention possess an asymmetric center at the carbon bearing the $R^2/R^3$ substituent which can be either R or S configuration. These enantiomeric mixtures may be separated or resolved to single enantiomers using methods familiar to those skilled in the art. For example, compounds of the present invention may be resolved to the pure isomers by using chiral SFC chromatography. Racemic material can be resolved to enantiomerically pure compounds whenever possible and at any step in the route. Characterization data may be of the chiral or racemic material.

The independent synthesis of diastereomers and enantiomers or their chromatographic separations may be achieved as known in the art by appropriate modification of the methodology disclosed herein. Their absolute stereochemistry may be determined by X-ray crystallography of crystalline products or crystalline intermediates which are derivatized, if necessary, with a reagent containing an asymmetric center of known absolute stereochemistry, or by vibrational circular dichroism (VCD) spectroscopy.

Throughout the synthetic schemes and examples, abbreviations and acronyms may be used with the following meanings unless otherwise indicated: aq, aq.=aqueous; Ac=acetate; ACN=acetonitrile; AIBN=azobisisobutyronitrile; anhyd.=anhydrous; Ar=aryl; br s=broad singlet; Bu=butyl, t-Bu=tert-butyl; Bn=benzyl; t-BuONO=tert-butyl nitrite; t-BuOH=tert butanol; t-BuOK=potassium tert-butoxide; ° C.=degree; CELITE=diatomaceous earth; Celsius; $CD_3CN$=deuterated acetonitrile; $CD_3OD$=deuterated methanol; cPr, cyPr=cyclopropyl; conc, conc.=concentrated; DBU=1,8-diazobicyclo[5.4.0]undec-7-ene; dppf=1,1'-Bis(diphenylphosphino)ferrocene; DCM=dichloromethane; DCE=1,2-dichloroethane; DME=1,2-dimethoxyethane; DIEA=N,N-diisopropylethylamine; DMF=N,N-dimethylformamide; DMA, DMAC=dimethylacetamide; DMSO=dimethylsulfoxide; Et=ethyl; eq.=equivalent(s); EtOAc=ethyl acetate; EtOH=ethanol; h, hr=hour; HPLC=High pressure liquid chromatography; iPr=isopropyl; iPA, IPA, i-PrOH=isopropyl alcohol; LDA=lithium diisopropylamide; LiHMDS=lithium bis(trimethylsilyl)amide; Me=methyl; MeOH=methanol; mg=milligram; min, min.=minute; mL=milliliter; Mp=melting point; mCPBA=3-chloroperoxybenzoic acid; min.=minute; mmol is millimoles; NaHMDS=sodium bis(trimethylsilyl)amide; NBS=N-bromosuccinimide; NMP=N-methylpyrrolidone; PE=petroleum ether; PDA=photodiode array; NMR=nuclear magnetic resonance; Oxone®=potassium peroxymonosulfate; Pr=propyl; Ph=phenyl; rt=retention time; psig=pounds per square inch gauge; RT=room temperature; sat., satd=saturated; SFC=supercritical fluid chromatography; TEA=triethylamine; TFA=trifluoroacetic acid; THF=tetrahydrofuran; TLC=thin layer chromatography; prep TLC=preparative thin layer chromatography; LCMS, LC/MS=liquid chromatography-mass spectrometry The following examples are provided to more fully illustrate the present invention, and shall not be construed as limiting the scope in any manner. Unless stated otherwise, the following conditions were employed. All operations were carried out at room or ambient temperature (RT), that is, at a temperature in the range 18-25° C. Reactions are generally done using commercially available anhydrous solvents under an inert atmosphere, either nitrogen or argon. Microwave reactions were done using a BIOTAGE Initiator™ or CEM Explorer® system. Evaporation of solvent was carried out using a rotary evaporator under reduced pressure (4.5-30 mmHg) with a bath temperature of up to 50° C. The course of reactions was followed by thin layer chromatography (TLC) and/or tandem high performance liquid chromatography (HPLC) followed by electron spray mass spectroscopy (MS), herein termed LCMS, and any reaction times are given for illustration only. The structure of all final compounds was assured by at least one of the following techniques: MS or proton nuclear magnetic resonance (1H NMR) spectrometry, and the purity was assured by at least one of the following techniques: TLC or HPLC. ¹H NMR spectra were recorded on either a Varian Unity or a Varian Inova instrument at 400, 500 or 600 MHz using the indicated solvent; when line-listed, NMR data is in the form of delta values for major diagnostic protons, given in parts per million (ppm) relative to residual solvent peaks (multiplicity and number of hydrogens); conventional abbreviations used for signal shape are: s. singlet; d. doublet (apparent); t. triplet (apparent); m. multiplet; br. broad; etc. MS data were recorded on a Waters Micromass unit, interfaced with a Hewlett-Packard (Agilent 1100) HPLC instrument, and operating on MassLynx/OpenLynx software; electrospray ionization was used with positive (ES+) or negative ion (ES−) detection; and diode array detection. Purification of compounds by preparative reverse phase HPLC was performed on a Gilson system using a YMC-Pack Pro C18 column (150×20 mm i.d.) eluting at 20 mL/min with a water/acetonitrile (0.1% TFA) gradient (typically 5% acetonitrile to 95% acetonitrile) using a Sunfire Prep C18 OBD 5 μM column (100×30 mm i.d.) eluting at 50 mL/min with a water/acetonitrile (0.1% TFA) gradient. Purification of compounds by preparative thin layer chromatography (PTLC) was conducted on 20×20 cm glass plates coated with silica gel, commercially available from Analtech; or E. Merck. Flash column chromatography was carried out on a glass silica gel column using Kieselgel 60, 0.063-0.200 mm (SiO₂), or on a Biotage SiO₂ cartridge system using the Biotage Horizon and Biotage SP-1 systems; or a Teledyne Isco SiO₂ cartridge using the CombiFlashRf system. Chemical symbols have their usual meanings, and the following abbreviations have also been used: h (hours), min (minutes), v (volume), w (weight), b.p. (boiling point), m.p. (melting point), L (liter(s)), mL (milliliters), g (gram(s)), mg (milligrams(s)), mol (moles), mmol (millimoles), eq or equiv (equivalent(s)), uM (micromolar), nM (nanomolar), ca (circa/about).

The following are representative procedures for the preparation of intermediates used to prepare the final products described in the Examples that follow thereafter. These examples are provided for the purpose of further illustration only and are not intended to be limitations on the disclosed invention.

It is understood that a chiral center in a compound may exist in the "S" or "R" stereo-configurations, or as a mixture of both. In some of the examples for intermediate compounds and final compounds, such compounds having a racemic chiral center were separated into individual stereoisomers, for example, referred to as isomer A (or enantiomer A or the like), which refers to the observed faster eluting isomer, and isomer B (or enantiomer B or the like), which refers to the observed slower eluting isomer, and each such isomer may be noted in the example as either the fast or slow eluting isomer. When a single "A" or "B" isomer intermediate is used to prepare a downstream compound, the downstream compound may take the "A" or "B" designation that corresponds to the previously used intermediate.

Any Intermediates described below may be referred to herein by their number preceded by "I-." For illustration, in the example titled "Intermediate 2," the racemic parent title compound would be referred to as Intermediate 2 (or I-2), and the separated stereoisomers are noted as Intermediates 2A and 2B (or I-2A and I-2B). In some examples, compounds having a chiral center were derived synthetically from a single isomer intermediate; e.g., Example 1 was made using stereoisomer I-1A.

Absolute stereochemistry of separate stereoisomers in the Examples and Intermediates was not determined unless stated otherwise in an Example or Intermediate synthesis Intermediate 1, 1A and 1B Ethyl 3,3-dicyano-2-(4-fluorophenyl)-2-methylpropanoate and the S and R Isomers Thereof

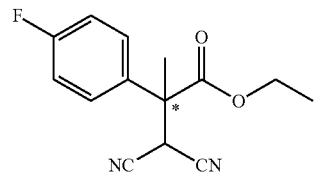 [SMILES: CCOC(=O)C(C)(c1ccc(F)cc1)C(C#N)C#N]

Step A—Ethyl 2-(4-fluorophenyl)-2-oxoacetate

Into a flask was placed a solution of diethyl oxalate (28.5 g, 195 mmol) in THF (300 mL) which was cooled at −78° C. 4-Fluorophenylmagnesium bromide (150 mL, 1.0 M in THF) was added dropwise, and the resulting solution was stirred for 1.5 h with warming to RT. The reaction was quenched by the addition of saturated aqueous NH₄Cl. The resulting solution was extracted with EtOAc (3×) and the organic layers were combined, dried over anhyd. Na₂SO₄, and filtered. The filtrate was concentrated in vacuo to dryness. The residue was purified by silica gel chromatography with EtOAc: PE (1%) to afford the title compound.

Step B—Ethyl 3,3-dicyano-2-(4-fluorophenyl)acrylate

Into a flask was placed the intermediate from Step A (28.0 g, 143 mmol), malononitrile (37.7 g, 571 mmol), piperidine (2.5 mL), and EtOH (125 mL). The resulting solution was stirred 16 h at reflux. Upon completion, the resulting mixture was concentrated in vacuo. The residue was purified by silica gel chromatography with EtOAc:PE (10%) to afford the title compound.

Step C—Ethyl 3,3-dicyano-2-(4-fluorophenyl)-2-methylpropanoate

Into a flask was placed the intermediate from Step B (3.0 g, 12 mmol), THF (50 mL), and lithium chloride (1.0 g, 23.6 mmol) which was cooled at 0° C. Subsequently, MeMgBr (7 mL) was added dropwise, and the resulting solution was stirred for 1 h at 0° C. The reaction was then quenched by the addition of water. The resulting solution was extracted with EtOAc (2×). The organic layers were combined, dried over anhyd. Na₂SO₄, and filtered. The filtrate was concentrated in vacuo to dryness. The residue was purified by silica gel chromatography with EtOAc: PE (25%) to afford the title compound. The racemic material was resolved using chiral SFC (OJ column) to afford isomers I-1A (faster eluting) and I-1B (slower eluting) of the title compound. ¹H NMR (300 MHz, CDCl₃): δ 7.40-7.33 (2H, m), 7.17-7.09 (2H, m), 4.45 (1H, s), 4.30 (2H, q, J=7.2 Hz), 1.99 (3H, s), 1.26 (3H, t, J=7.2 Hz).

Intermediate 2, 2A and 2B

Ethyl 2-(4-chlorophenyl)-3,3-dicyano-2-methylpropanoate and the R and S Isomers Thereof

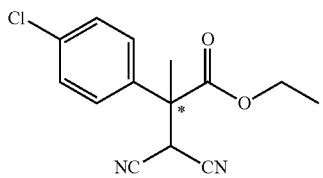 [SMILES: CCOC(=O)C(C)(c1ccc(Cl)cc1)C(C#N)C#N]

The title compound was prepared using essentially the same procedure as described in Intermediate 1 with either commercial starting reagents or those known in the literature. The racemic material was resolved using a chiral SFC (OJ column) to afford isomer I-2A (faster eluting) and isomer I-2B (slower eluting) of the title compound. m/z=275 (M-1).

Intermediate 3, 3A and 3B

Ethyl 3,3-dicyano-2-(5-fluoropyridin-2-yl)-2-methylpropanoate and the R and S Isomers Thereof

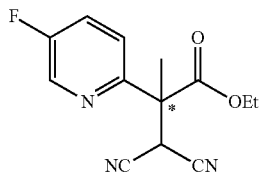 [SMILES: CCOC(=O)C(C)(c1ccc(F)cn1)C(C#N)C#N]

Step A—Diethyl 2-(5-fluoropyridin-2-yl)malonate

Into a flask, was placed 2-bromo-5-fluoropyridine (20.0 g, 114 mmol), 1,3-diethyl propanedioate (54.5 g, 340 mmol), picolinic acid (5.6 g, 45 mmol), $Cs_2CO_3$ (143 g, 438 mmol), CuI (4.3 g, 23 mmol), and dioxane (500 mL). The resulting solution was stirred for 12 h at 100° C. The resulting solution was quenched by the addition of water (300 mL). The resulting solution was extracted with EtOAc (2×), the organic layers combined and dried over anhyd. $Na_2SO_4$, and concentrated in vacuo to dryness. The residue was purified by silica chromatography using EtOAc: PE (0-20%) to afford the title compound.

Step B—Ethyl 2-(5-fluoropyridin-2-yl)acetate

Into a 3-necked round-bottom flask, was placed the intermediate from Step A (46 g, crude), NaCl (20 g, 342 mmol), water (6 mL), and DMSO (90 mL). The resulting solution was stirred for 3 h at 180° C. Upon completion, the resulting solution was diluted with EtOAc, washed with water (5×) and the organic layer was dried over anhyd. $Na_2SO_4$ and concentrated in vacuo to dryness. The residue was purified by silica chromatography using EtOAc:PE (0-20%) to afford the title compound.

Step C—Ethyl 2-(5-fluoropyridin-2-yl)propanoate

Into a flask was placed THF (200 mL) and LiHMDS (45 mL, 1.0 M). This was followed by dropwise addition of the intermediate from Step B (7.5 g, 41 mmol) with stirring at 0° C. After stirring the resulting solution for 1 h, a solution of iodomethane (5.8 g, 41 mmol) in THF (10 mL) was added dropwise. The resulting solution was stirred for 3 h at 0° C. The reaction was then quenched by the addition of water. The resulting mixture was extracted with EtOAc (3×), the organic layers combined and dried over anhyd. $Na_2SO_4$, and concentrated in vacuo to dryness. The residue was purified by silica chromatography using EtOAc:PE (0-20%) to afford the title compound.

Step D—Ethyl 2-bromo-2-(5-fluoropyridin-2-yl)propanoate

Into a flask was added the intermediate from Step C (1 g, 5 mmol) and THF (50 mL). This was followed by the addition of LiHMDS (5 mL, 1.0 M) dropwise with stirring at -78° C. The resulting solution was stirred for 30 min at -78° C. before NBS (1.2 g, 7.1 mmol) in THF (10 mL) was added, and the solution was warmed to RT and stirred for 1 h. The reaction was then quenched by the addition of water. The resulting solution was extracted with EtOAc (3×) and the organic layers combined and dried over anhyd. $Na_2SO_4$. The solid was filtered and the eluent was concentrated in vacuo to dryness. The residue was purified by silica chromatography using EtOAc: PE (0-10%) to afford the title compound.

Step E—Ethyl 3,3-dicyano-2-(5-fluoropyridin-2-yl)-2-methylpropanoate

Into a flask was placed DMF (20 mL) and NaH (260 mg, 6.50 mmol, 60%). This was followed by the addition of malononitrile (460 mg, 6.96 mmol) with stirring at 0° C. The resulting solution was stirred for 30 min at 0° C. To this was added the intermediate from Step D (950 mg, 3.44 mmol) in DMF dropwise with stirring at 0° C. The resulting solution was stirred for 1 h at RT. Upon completion, the resulting solution was quenched with water, and extracted with EtOAc. The organic layer was dried over anhyd. $Na_2SO_4$ and concentrated in vacuo to dryness. The residue was purified by silica chromatography using EtOAc:PE (0-20%). The racemic material was resolved using a chiral SFC (IA column) to afford isomers I-3A (faster eluting) and I-3B (slower eluting) of the title compound. $^1$H NMR: (300 MHz, $CDCl_3$): δ 8.44-8.45 (1H, dd, J=0.9, 2.4 Hz), 7.47-7.57 (2H, m), 5.17 (1H, s), 4.19-4.29 (2H, m), 2.00 (3H, s), 1.22-1.27 (3H, t, J=6.9 Hz).

Intermediate 4, 4A and 4B

Methyl 3,3-dicyano-2-methyl-2-phenylpropanoate and the R and S Isomers Thereof

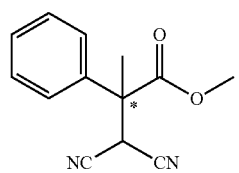 [SMILES: COC(=O)C(C)(c1ccccc1)C(C#N)C#N]

The title compound was prepared using essentially the same procedure as described in Intermediate 3 with either commercial starting reagents or those known in the literature. The racemic material was resolved using a chiral SFC (AD column) to afford isomer I-4A (faster eluting) and isomer I-4B (slower eluting) of the title compound. $^1$H NMR (500 MHz, CDCl$_3$): δ 7.44-7.42 (3H, m), 7.38-7.36 (2H, m), 4.50 (1H, s), 3.80 (3H, s), 2.00 (3H, s).

Intermediate 5, 5A and 5B

Ethyl 3,3-dicyano-2-cyclopropyl-2-(4-fluorophenyl)propanoate and the R and S Isomers Thereof

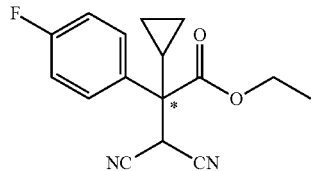 [SMILES: CCOC(=O)C(c1ccc(F)cc1)(C(C#N)C#N)C1CC1]

Step A—Ethyl 2-cyclopropyl-2-oxoacetate

Into a flask was placed a solution of diethyl oxalate (28.5 g, 195 mmol) in THF (200 mL) which was cooled at −78° C. Cyclopropylmagnesium bromide (150 mL, 150 mmol, THF) was added dropwise, and the resulting solution was stirred for 2 h with warming to RT. The reaction was quenched by the addition of saturated aqueous NH$_4$Cl. The resulting solution was extracted with EtOAc (3×) and the organic layers were combined, washed with brine, dried over anhyd. Na$_2$SO$_4$, and filtered. The filtrate was concentrated in vacuo to dryness. The residue was purified by silica gel chromatography with DCM: PE (40-60%) to afford the title compound.

Step B—Ethyl 3,3-dicyano-2-cyclopropylacrylate

Into a flask were placed the intermediate from Step A (5.6 g, 39 mmol), malononitrile (2.6 g, 39 mmol), EtOH (5 mL) and a solution of 3-aminopropanoic acid (175 mg) in water (5 mL). The resulting solution was stirred 16 h at RT. The reaction was quenched by the addition of water. The resulting solution was extracted with EtOAc (2×) and the organic layers were combined, washed with brine (2×), dried over anhyd. Na$_2$SO$_4$, and filtered. The filtrate was concentrated in vacuo to dryness. The residue was purified by silica gel chromatography with EtOAc: PE (5-15%) to afford the title compound.

Step C—Ethyl 3,3-dicyano-2-cyclopropyl-2-(4-fluorophenyl)propanoate

Into a flask was placed a solution of the intermediate from Step B (1.0 g, 5.7 mmol) in THF (30 mL) which was cooled at −50° C. (4-Fluorophenyl)magnesium bromide (0.43 N in THF, 20 mL, 8.53 mmol) was added dropwise and the resulting solution was stirred for 1 h with warming to RT. The reaction was quenched by the addition of saturated NH$_4$Cl. The resulting solution was extracted with EtOAc (3×) and the organic layers were combined, dried over anhyd. Na$_2$SO$_4$, and filtered. The filtrate was concentrated in vacuo to dryness. The residue was purified by silica gel chromatography with EtOAc:PE (10%) to afford the racemic title compound. The racemic material was resolved using a chiral SFC (AS column) to afford isomer I-5A (faster eluting) and isomer I-5B (slower eluting) of the title compound. m/z=285.0 (M-1).

Intermediate 6

Methyl 3,3-dicyano-2,2-dimethylpropanoate

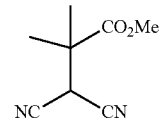

A 3 neck round bottom flask equipped with a mechanical stirrer, thermometer, condenser and nitrogen bubbler, was charged with malononitrile (251 g, 3.80 moles) and THF (2 liters). t-BuOK (1M THF, 3.80 L, 3.80 moles) was then added. The mixture was stirred at 50° C. for 0.5 h. Methyl 2-bromoisobutyrate (688 g, 3.80 moles) was added and the reaction mixture was stirred overnight at 50° C. The reaction was partitioned between aqueous 1 N HCl and EtOAc. The organic phase was washed with brine, dried over anhyd. magnesium sulfate, filtered, and concentrated to afford the title compound. $^1$H NMR (400 MHz, CD$_3$CN): δ 4.35 (1H, s) 3.73 (3H, s), 1.43 (6H, s).

Example 1A

4-Amino-2-[8-(3-fluorophenoxy)imidazo[1,2-a]pyrazin-6-yl]-5-(4-fluorophenyl)-5-methyl-5,7-dihydro-6H-pyrrolo[2,3-d]pyrimidin-6-one

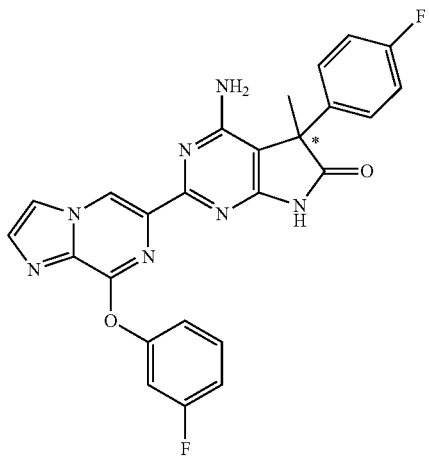 [SMILES: CC1(c2ccc(F)cc2)C(=O)Nc2nc(-c3cn4ccnc4c(Oc4cccc(F)c4)n3)nc(N)c21]

Step A—6-Bromo-8-(3-fluorophenoxy)imidazo[1,2-a]pyrazine

In a vial was placed 6,8-dibromoimidazo[1,2-a]pyrazine (205 mg, 0.740 mmol), Cs$_2$CO$_3$ (482 mg, 1.481 mmol), 3-fluorophenol (73.7 µl, 0.814 mmol), and DMF (3.7 mL). After 20 min, the reaction mixture was diluted with EtOAc (50 mL), and the solid precipitate was filtered. The remaining eluent was concentrated in vacuo to dryness. The residue was dissolved in EtOAc, washed with water and brine. The organic layer was dried over anhyd.

Na$_2$SO$_4$ and filtered. The filtrate was concentrated in vacuo to dryness. The residue was purified by silica gel chromatography with EtOAc:hexanes (10-80%) to afford the title compound. m/z=309.8 (M+H).

Step B—8-(3-Fluorophenoxy)imidazo[1,2-a]pyrazine-6-carbonitrile

Into a vial was placed the intermediate from Step A (120 mg, 0.389 mmol), zinc cyanide (45.7 mg, 0.389 mmol), and Pd(dppf)Cl$_2$ (28.5 mg, 0.039 mmol), which was secured with a pierce-able cap. The sealed vial was evacuated and refilled with N$_2$ (3×). DMA (1.56 mL) was added and the reaction was warmed at 120° C. After 18 h, the reaction was diluted with EtOAc and quenched with satd. aq. NaHCO$_3$, and the resulting mixture was filtered through a plug of CELITE. The solution was extracted with EtOAc (2×) and the organic layers were combined, dried over anhyd. Na$_2$SO$_4$, filtered, and the filtrate was concentrated in vacuo to dryness. The residue was purified by silica gel chromatography with EtOAc:hexanes (0-100%) to afford the title compound. m/z=254.9 (M+H).

Step C—8-(3-Fluorophenoxy)imidazo[1,2-a]pyrazine-6-carboximidamide

Into a vial, purged with an inert atmosphere of nitrogen, was placed the intermediate from Step B (145 mg, 0.57 mmol). To this was added amino(methyl)aluminum chloride (5.0 mL, 5.0 mmol, 1.0 M in toluene), and the resulting mixture was warmed at 110° C. After 2 h, the reaction mixture was cooled to 0° C. The reaction was then quenched by the addition of MeOH:DCM (1:4, 400 mL). After vigorous stirring, the solid was filtered through a pad of CELITE. The resulting eluent was concentrated in vacuo to dryness. This afforded the HCl salt of 8-(3-fluorophenoxy)imidazo[1,2-a]pyrazine-6-carboximidamide, which was used without purification. m/z=272.1 (M+H).

Step D—4-Amino-2-[8-(3-fluorophenoxy)imidazo[1,2-a]pyrazin-6-yl]-5-(4-fluorophenyl)-5-methyl-5,7-dihydro-6H-pyrrolo[2,3-d]pyrimidin-6-one Into a vial, purged with an inert atmosphere of nitrogen, was placed t-BuOH (1.29 mL), the intermediate from Step C (70 mg, 0.26 mmol), I-1A (81 mg, 0.31 mmol) and KHCO$_3$ (78 mg, 0.77 mmol). The heterogeneous mixture was stirred at 80° C. for 16 h. The reaction mixture was cooled to RT and diluted with MeOH. The resulting precipitate was filtered and the filtrate was concentrated in vacuo to dryness. The residue was purified by silica gel chromatography with EtOAc:hexanes (10-100%) to afford the title compound. $^1$H NMR (500 MHz, CD$_3$OD): δ 9.20 (1H, s), 8.13 (1H, d, J=1.3 Hz), 7.78 (1H, d, J=1.3 Hz), 7.42 (1H, q, J=7.6 Hz), 7.31-7.25 (4H, m), 7.06-6.95 (3H, m), 1.81 (3H, s); m/z=486.0 (M+H).

TABLE 1

Examples 2A-34A

Using essentially the same procedures described in Example 1A, the following compounds in Table 1 were prepared.

| Ex No. | Structure | IUPAC Name | Chiral starting material | [M + H]$^+$ |
|---|---|---|---|---|
| 2A | 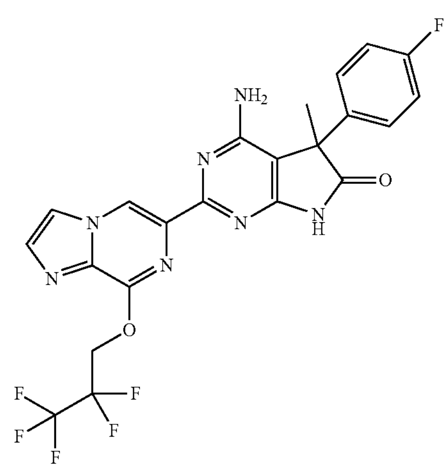 [SMILES: CC1(c2ccc(F)cc2)C(=O)Nc2nc(-c3cn4ccnc4c(OCC(F)(F)C(F)(F)F)n3)nc(N)c21] | 4-amino-5-(4-fluorophenyl)-5-methyl-2-[8-(2,2,3,3,3-pentafluoropropoxy)imidazo[1,2-a]pyrazin-6-yl]-5,7-dihydro-6H-pyrrolo[2,3-d]pyrimidin-6-one | I-1A | 524.0 |

TABLE 1-continued

Examples 2A-34A
Using essentially the same procedures described in Example 1A, the following
compounds in Table 1 were prepared.

| Ex No. | Structure | IUPAC Name | Chiral starting material | [M + H]+ |
|---|---|---|---|---|
| 3B | 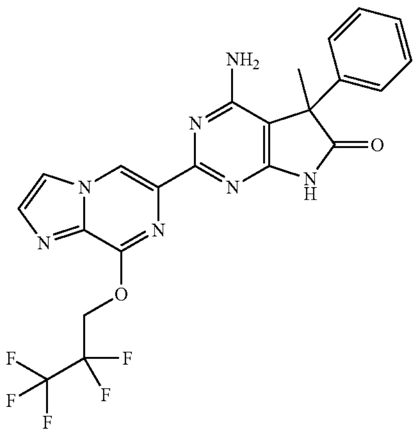 [SMILES: CC1(c2ccccc2)C(=O)Nc2nc(-c3cn4ccnc4c(OCC(F)(F)C(F)(F)F)n3)nc(N)c21] | 4-amino-5-methyl-2-[8-(2,2,3,3,3-pentafluoropropoxy)imidazo[1,2-a]pyrazin-6-yl]-5-phenyl-5,7-dihydro-6H-pyrrolo[2,3-d]pyrimidin-6-one | I-4B | 506.0 |
| 4A | 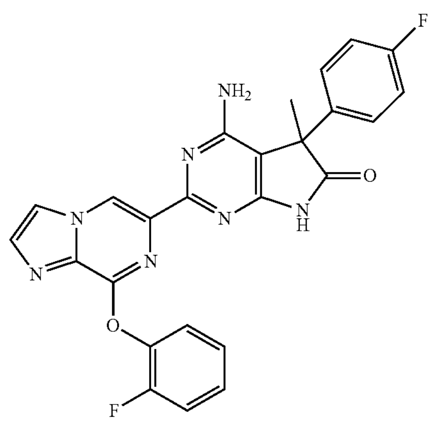 [SMILES: CC1(c2ccc(F)cc2)C(=O)Nc2nc(-c3cn4ccnc4c(Oc4ccccc4F)n3)nc(N)c21] | 4-amino-2-[8-(2-fluorophenoxy)imidazo[1,2-a]pyrazin-6-yl]-5-(4-fluorophenyl)-5-methyl-5,7-dihydro-6H-pyrrolo[2,3-d]pyrimidin-6-one | I-1A | 486.0 |
| 5B | 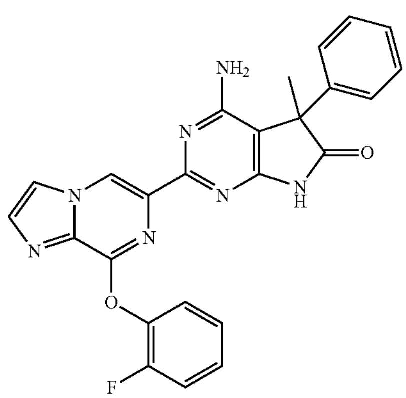 [SMILES: CC1(c2ccccc2)C(=O)Nc2nc(-c3cn4ccnc4c(Oc4ccccc4F)n3)nc(N)c21] | 4-amino-2-[8-(2-fluorophenoxy)imidazo[1,2-a]pyrazin-6-yl]-5-methyl-5-phenyl-5,7-dihydro-6H-pyrrolo[2,3-d]pyrimidin-6-one | I-4B | 468.0 |

TABLE 1-continued

Examples 2A-34A

Using essentially the same procedures described in Example 1A, the following compounds in Table 1 were prepared.

| Ex No. | Structure | IUPAC Name | Chiral starting material | [M + H]+ |
| --- | --- | --- | --- | --- |
| 6A | 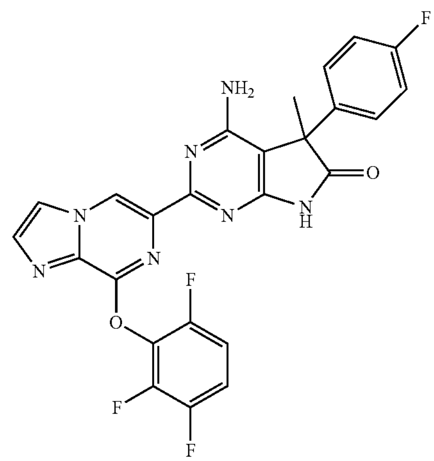 [SMILES: CC1(c2ccc(F)cc2)C(=O)Nc2nc(-c3cn4ccnc4c(Oc4c(F)ccc(F)c4F)n3)nc(N)c21] | 4-amino-5-(4-fluorophenyl)-5-methyl-2-[8-(2,3,6-trifluorophenoxy)imidazo[1,2-a]pyrazin-6-yl]-5,7-dihydro-6H-pyrrolo[2,3-d]pyrimidin-6-one | I-1A | 522.0 |
| 7B | 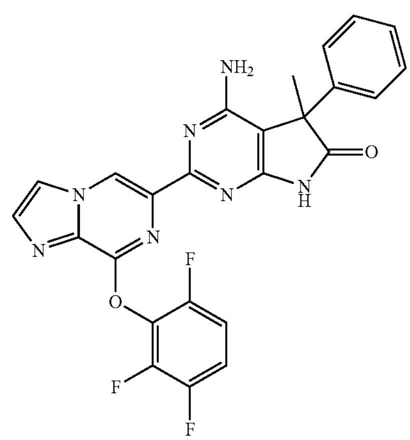 [SMILES: CC1(c2ccccc2)C(=O)Nc2nc(-c3cn4ccnc4c(Oc4c(F)ccc(F)c4F)n3)nc(N)c21] | 4-amino-5-methyl-5-phenyl-2-[8-(2,3,6-trifluorophenoxy)imidazo[1,2-a]pyrazin-6-yl]-5,7-dihydro-6H-pyrrolo[2,3-d]pyrimidin-6-one | I-4B | 504.0 |
| 8B | 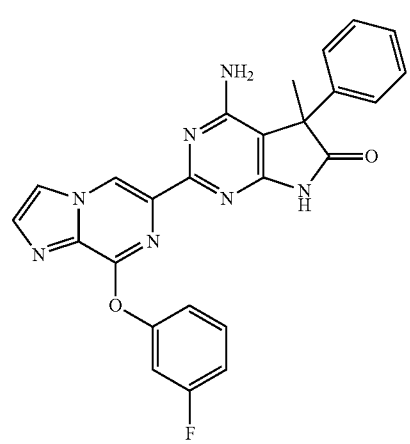 [SMILES: CC1(c2ccccc2)C(=O)Nc2nc(-c3cn4ccnc4c(Oc4cccc(F)c4)n3)nc(N)c21] | 4-amino-2-[8-(3-fluorophenoxy)imidazo[1,2-a]pyrazin-6-yl]-5-methyl-5-phenyl-5,7-dihydro-6H-pyrrolo[2,3-d]pyrimidin-6-one | I-4B | 468.0 |

TABLE 1-continued

Examples 2A-34A
Using essentially the same procedures described in Example 1A, the following
compounds in Table 1 were prepared.

| Ex No. | Structure | IUPAC Name | Chiral starting material | [M + H]+ |
|---|---|---|---|---|
| 9A | 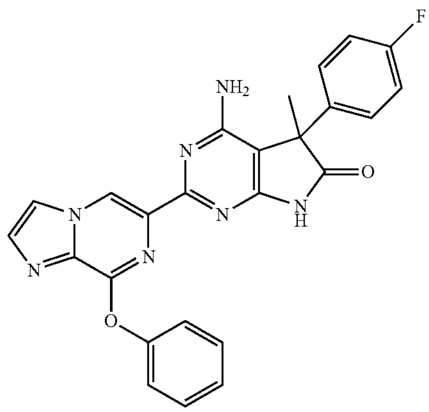 [SMILES: CC1(c2ccc(F)cc2)C(=O)Nc2nc(-c3cn4ccnc4c(Oc4ccccc4)n3)nc(N)c21] | 4-amino-5-(4-fluorophenyl)-5-methyl-2-(8-phenoxyimidazo[1,2-a]pyrazin-6-yl)-5,7-dihydro-6H-pyrrolo[2,3-d]pyrimidin-6-one | I-1A | 468.0 |
| 10B | 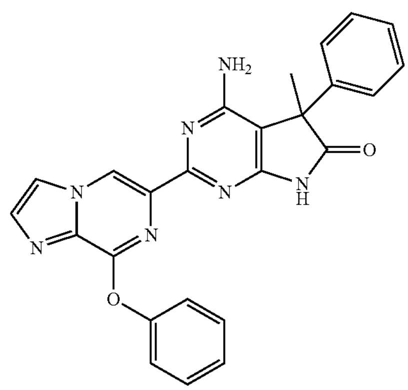 [SMILES: CC1(c2ccccc2)C(=O)Nc2nc(-c3cn4ccnc4c(Oc4ccccc4)n3)nc(N)c21] | 4-amino-5-methyl-2-(8-phenoxy-imidazo[1,2-a]pyrazin-6-yl)-5-phenyl-5,7-dihydro-6H-pyrrolo[2,3-d]pyrimidin-6-one | I-4B | 450.0 |
| 11B | 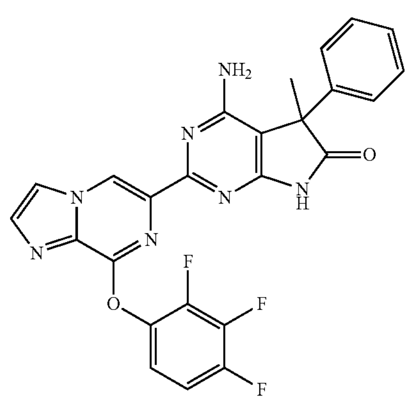 [SMILES: CC1(c2ccccc2)C(=O)Nc2nc(-c3cn4ccnc4c(Oc4ccc(F)c(F)c4F)n3)nc(N)c21] | 4-amino-5-methyl-5-phenyl-2-[8-(2,3,4-trifluoro-phenoxy)imidazo[1,2-a]pyrazin-6-yl]-5,7-dihydro-6H-pyrrolo[2,3-d]pyrimidin-6-one | I-4B | 504.1 |

TABLE 1-continued

Examples 2A-34A

Using essentially the same procedures described in Example 1A, the following compounds in Table 1 were prepared.

| Ex No. | Structure | IUPAC Name | Chiral starting material | [M + H]+ |
|---|---|---|---|---|
| 12B | 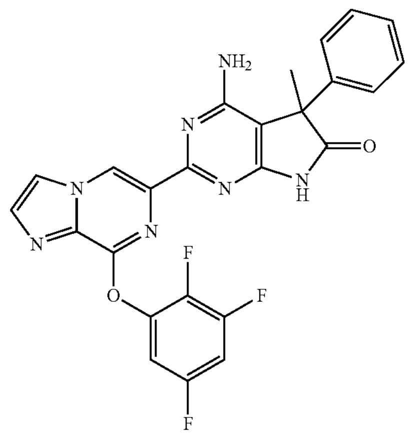 [SMILES: CC1(c2ccccc2)C(=O)Nc2nc(-c3cn4ccnc4c(Oc4cc(F)cc(F)c4F)n3)nc(N)c21] | 4-amino-5-methyl-5-phenyl-2-[8-(2,3,5-trifluoro-phenoxy)imidazo[1,2-a]pyrazin-6-yl]-5,7-dihydro-6H-pyrrolo[2,3-d]pyrimidin-6-one | I-4B | 504.1 |
| 13B | 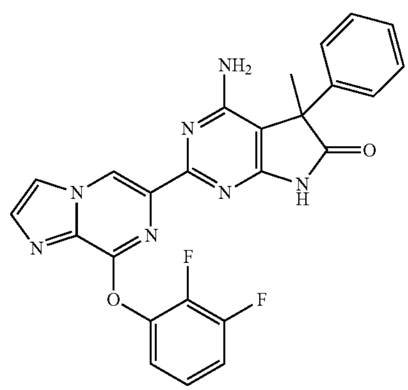 [SMILES: CC1(c2ccccc2)C(=O)Nc2nc(-c3cn4ccnc4c(Oc4cccc(F)c4F)n3)nc(N)c21] | 4-amino-2-[8-(2,3-difluoro-phenoxy)imidazo[1,2-a]pyrazin-6-yl]-5-methyl-5-phenyl-5,7-dihydro-6H-pyrrolo[2,3-d]pyrimidin-6-one | I-4B | 485.9 |
| 14B | 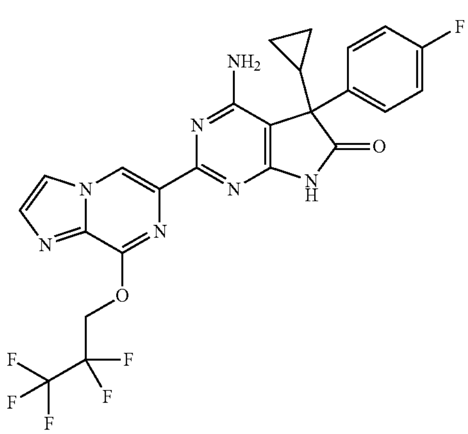 [SMILES: Nc1nc(-c2cn3ccnc3c(OCC(F)(F)C(F)(F)F)n2)nc2c1C(c1ccc(F)cc1)(C1CC1)C(=O)N2] | 4-amino-5-cyclopropyl-5-(4-fluorophenyl)-2-[8-(2,2,3,3,3-pentafluoropropoxy)imidazo[1,2-a]pyrazin-6-yl]-5,7-dihydro-6H-pyrrolo[2,3-d]pyrimidin-6-one | I-5B | 549.9 |

TABLE 1-continued

Examples 2A-34A
Using essentially the same procedures described in Example 1A, the following compounds in Table 1 were prepared.

| Ex No. | Structure | IUPAC Name | Chiral starting material | [M + H]+ |
|---|---|---|---|---|
| 15A | 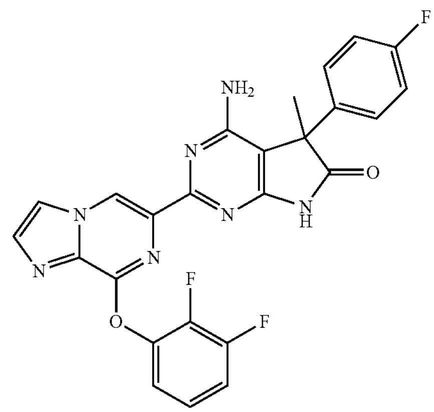 [SMILES: CC1(c2ccc(F)cc2)C(=O)Nc2nc(-c3cn4ccnc4c(Oc4cccc(F)c4F)n3)nc(N)c21] | 4-amino-2-[8-(2,3-difluorophenoxy)imidazo[1,2-a]pyrazin-6-yl]-5-(4-fluorophenyl)-5-methyl-5,7-dihydro-6H-pyrrolo[2,3-d]pyrimidin-6-one | I-1A | 503.9 |
| 16A | 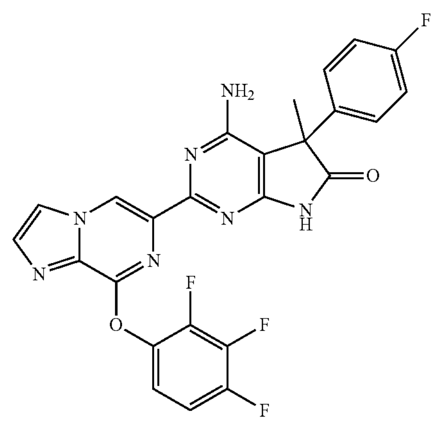 [SMILES: CC1(c2ccc(F)cc2)C(=O)Nc2nc(-c3cn4ccnc4c(Oc4ccc(F)c(F)c4F)n3)nc(N)c21] | 4-amino-5-(4-fluorophenyl)-5-methyl-2-[8-(2,3,4-trifluorophenoxy)imidazo[1,2-a]pyrazin-6-yl]-5,7-dihydro-6H-pyrrolo[2,3-d]pyrimidin-6-one | I-1A | 521.9 |
| 17A | 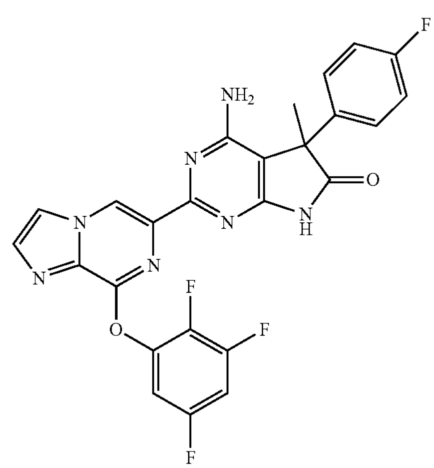 [SMILES: CC1(c2ccc(F)cc2)C(=O)Nc2nc(-c3cn4ccnc4c(Oc4cc(F)cc(F)c4F)n3)nc(N)c21] | 4-amino-5-(4-fluorophenyl)-5-methyl-2-[8-(2,3,5-trifluorophenoxy)imidazo[1,2-a]pyrazin-6-yl]-5,7-dihydro-6H-pyrrolo[2,3-d]pyrimidin-6-one | I-1A | 521.9 |

TABLE 1-continued

Examples 2A-34A

Using essentially the same procedures described in Example 1A, the following compounds in Table 1 were prepared.

| Ex No. | Structure | IUPAC Name | Chiral starting material | [M + H]+ |
|---|---|---|---|---|
| 18A | 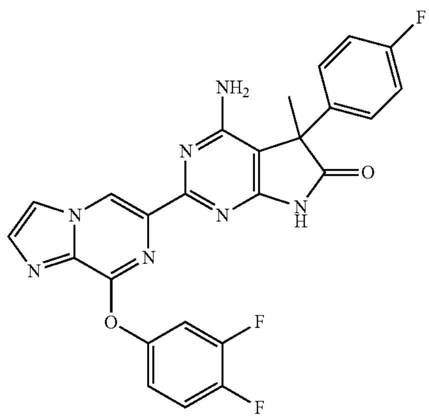 [SMILES: CC1(c2ccc(F)cc2)C(=O)Nc2nc(-c3cn4ccnc4c(Oc4ccc(F)c(F)c4)n3)nc(N)c21] | 4-amino-2-[8-(3,4-difluorophenoxy)imidazo[1,2-a]pyrazin-6-yl]-5-(4-fluorophenyl)-5-methyl-5,7-dihydro-6H-pyrrolo[2,3-d]pyrimidin-6-one | I-1A | 503.9 |
| 19A | 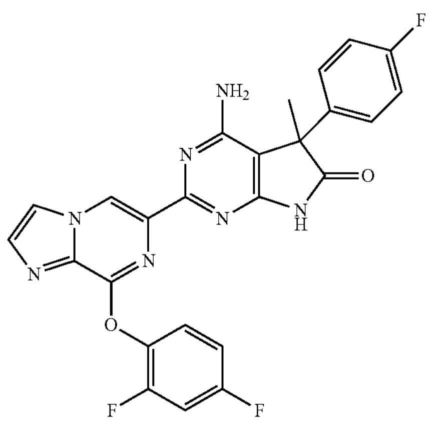 [SMILES: CC1(c2ccc(F)cc2)C(=O)Nc2nc(-c3cn4ccnc4c(Oc4ccc(F)cc4F)n3)nc(N)c21] | 4-amino-2-[8-(2,4-difluorophenoxy)imidazo[1,2-a]pyrazin-6-yl]-5-(4-fluorophenyl)-5-methyl-5,7-dihydro-6H-pyrrolo[2,3-d]pyrimidin-6-one | I-1A | 504.1 |
| 20A | 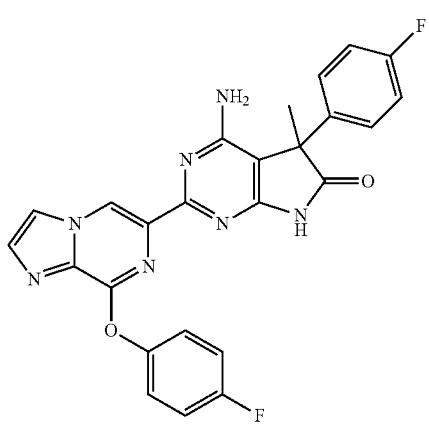 [SMILES: CC1(c2ccc(F)cc2)C(=O)Nc2nc(-c3cn4ccnc4c(Oc4ccc(F)cc4)n3)nc(N)c21] | 4-amino-2-[8-(4-fluorophenoxy)imidazo[1,2-a]pyrazin-6-yl]-5-(4-fluorophenyl)-5-methyl-5,7-dihydro-6H-pyrrolo[2,3-d]pyrimidin-6-one | I-1A | 486.1 |

TABLE 1-continued

Examples 2A-34A
Using essentially the same procedures described in Example 1A, the following compounds in Table 1 were prepared.

| Ex No. | Structure | IUPAC Name | Chiral starting material | [M + H]+ |
|---|---|---|---|---|
| 21A | 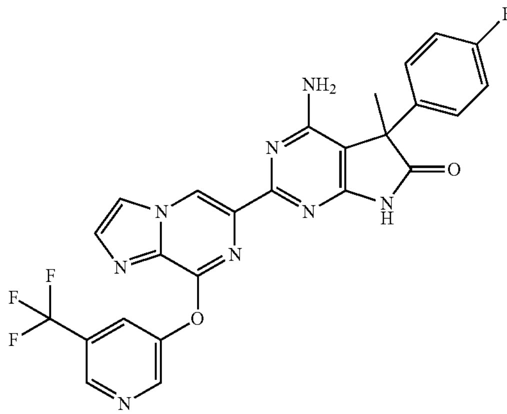 [SMILES: CC1(c2ccc(F)cc2)C(=O)Nc2nc(-c3cn4ccnc4c(Oc4cncc(C(F)(F)F)c4)n3)nc(N)c21] | 4-amino-5-(4-fluorophenyl)-5-methyl-2-(8-{[5-(trifluoromethyl)pyridin-3-yl]oxy}imidazo[1,2-a]pyrazin-6-yl)-5,7-dihydro-6H-pyrrolo[2,3-d]pyrimidin-6-one | I-1A | 537.1 |
| 22A | 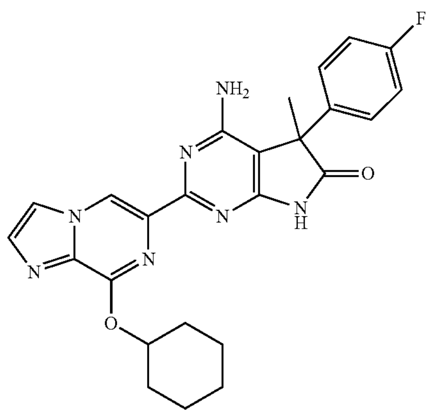 [SMILES: CC1(c2ccc(F)cc2)C(=O)Nc2nc(-c3cn4ccnc4c(OC4CCCCC4)n3)nc(N)c21] | 4-amino-2-[8-(cyclohexyloxy)imidazo[1,2-a]pyrazin-6-yl]-5-(4-fluorophenyl)-5-methyl-5,7-dihydro-6H-pyrrolo[2,3-d]pyrimidin-6-one | I-1A | 474.1 |
| 23A | 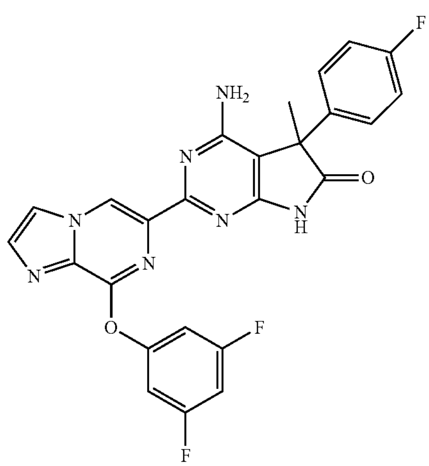 [SMILES: CC1(c2ccc(F)cc2)C(=O)Nc2nc(-c3cn4ccnc4c(Oc4cc(F)cc(F)c4)n3)nc(N)c21] | 4-amino-2-[8-(3,5-difluorophenoxy)imidazo[1,2-a]pyrazin-6-yl]-5-(4-fluorophenyl)-5-methyl-5,7-dihydro-6H-pyrrolo[2,3-d]pyrimidin-6-one | I-1A | 504.0 |

TABLE 1-continued

Examples 2A-34A
Using essentially the same procedures described in Example 1A, the following compounds in Table 1 were prepared.

| Ex No. | Structure | IUPAC Name | Chiral starting material | [M + H]+ |
|---|---|---|---|---|
| 24 | 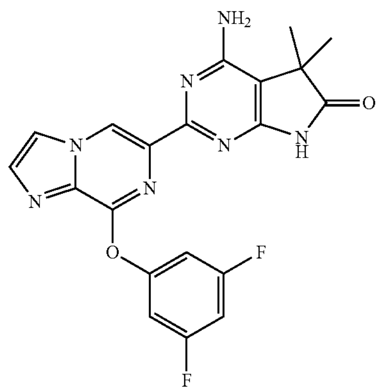 [SMILES: CC1(C)C(=O)Nc2nc(-c3cn4ccnc4c(Oc4cc(F)cc(F)c4)n3)nc(N)c21] | 4-amino-2-[8-(3,5-difluorophenoxy)imidazo[1,2-a]pyrazin-6-yl]-5,5-dimethyl-5,7-dihydro-6H-pyrrolo[2,3-d]pyrimidin-6-one | I-6 | 424.0 |
| 25A | 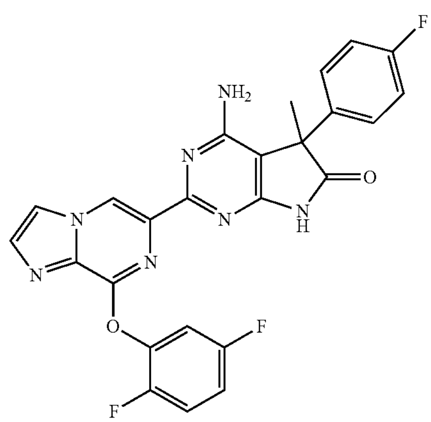 [SMILES: CC1(c2ccc(F)cc2)C(=O)Nc2nc(-c3cn4ccnc4c(Oc4cc(F)ccc4F)n3)nc(N)c21] | 4-amino-2-[8-(2,5-difluorophenoxy)imidazo[1,2-a]pyrazin-6-yl]-5-(4-fluorophenyl)-5-methyl-5,7-dihydro-6H-pyrrolo[2,3-d]pyrimidin-6-one | I-1A | 504.0 |
| 26 | 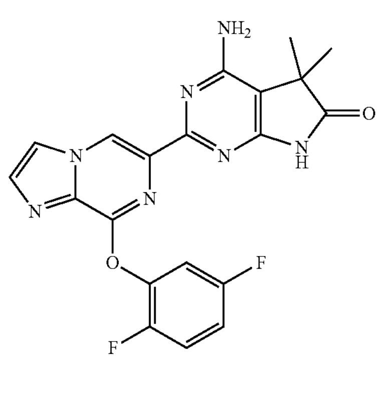 [SMILES: CC1(C)C(=O)Nc2nc(-c3cn4ccnc4c(Oc4cc(F)ccc4F)n3)nc(N)c21] | 4-amino-2-[8-(2,5-difluorophenoxy)imidazo[1,2-a]pyrazin-6-yl]-5,5-dimethyl-5,7-dihydro-6H-pyrrolo[2,3-d]pyrimidin-6-one | I-6 | 424.0 |

TABLE 1-continued

Examples 2A-34A

Using essentially the same procedures described in Example 1A, the following compounds in Table 1 were prepared.

| Ex No. | Structure | IUPAC Name | Chiral starting material | [M + H]+ |
|---|---|---|---|---|
| 27A | 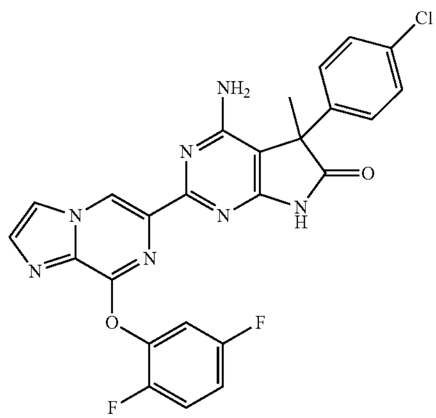 [SMILES: CC1(c2ccc(Cl)cc2)C(=O)Nc2nc(-c3cn4ccnc4c(Oc4cc(F)ccc4F)n3)nc(N)c21] | 4-amino-5-(4-chlorophenyl)-2-[8-(2,5-difluoro-phenoxy)imidazo[1,2-a]pyrazin-6-yl]-5-methyl-5,7-dihydro-6H-pyrrolo[2,3-d]pyrimidin-6-one | I-2A | 520.0 |
| 28A | 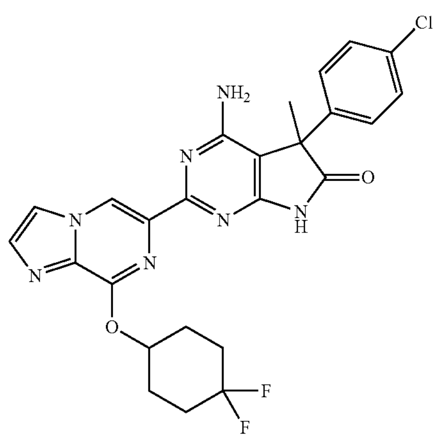 [SMILES: CC1(c2ccc(Cl)cc2)C(=O)Nc2nc(-c3cn4ccnc4c(OC4CCC(F)(F)CC4)n3)nc(N)c21] | 4-amino-5-(4-chlorophenyl)-2-{8-[(4,4-difluorocyclohexyl)oxy]imidazo[1,2-a]pyrazin-6-yl}-5-methyl-5,7-dihydro-6H-pyrrolo[2,3-d]pyrimidin-6-one | I-2A | 526.2 |
| 29A | 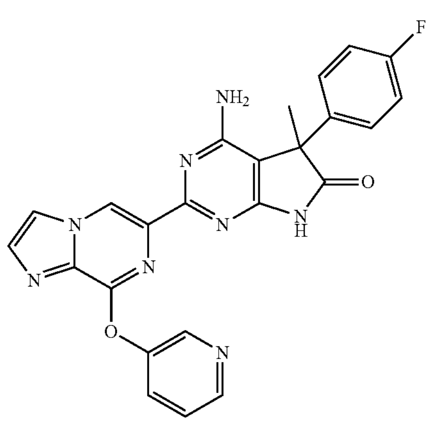 [SMILES: CC1(c2ccc(F)cc2)C(=O)Nc2nc(-c3cn4ccnc4c(Oc4cccnc4)n3)nc(N)c21] | 4-amino-5-(4-fluorophenyl)-5-methyl-2-[8-(pyridin-3-yloxy)imidazo[1,2-a]pyrazin-6-yl]-5,7-dihydro-6H-pyrrolo[2,3-d]pyrimidin-6-one | I-1A | 469.2 |

TABLE 1-continued

Examples 2A-34A
Using essentially the same procedures described in Example 1A, the following
compounds in Table 1 were prepared.

| Ex No. | Structure | IUPAC Name | Chiral starting material | [M + H]+ |
|---|---|---|---|---|
| 30A | 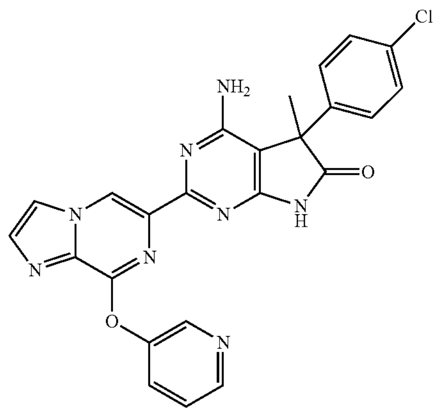 [SMILES: CC1(c2ccc(Cl)cc2)C(=O)Nc2nc(-c3cn4ccnc4c(Oc4cccnc4)n3)nc(N)c21] | 4-amino-5-(4-chlorophenyl)-5-methyl-2-[8-(pyridin-3-yloxy)imidazo[1,2-a]pyrazin-6-yl]-5,7-dihydro-6H-pyrrolo[2,3-d]pyrimidin-6-one | I-2A | 485.1 |
| 31A | 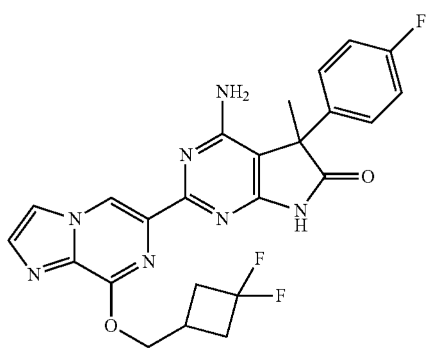 [SMILES: CC1(c2ccc(F)cc2)C(=O)Nc2nc(-c3cn4ccnc4c(OCC4CC(F)(F)C4)n3)nc(N)c21] | 4-amino-2-{8-[(3,3-difluorocyclobutyl)methoxy]imidazo[1,2-a]pyrazin-6-yl}-5-(4-fluorophenyl)-5-methyl-5,7-dihydro-6H-pyrrolo[2,3-d]pyrimidin-6-one | I-1A | 496.1 |
| 32A | 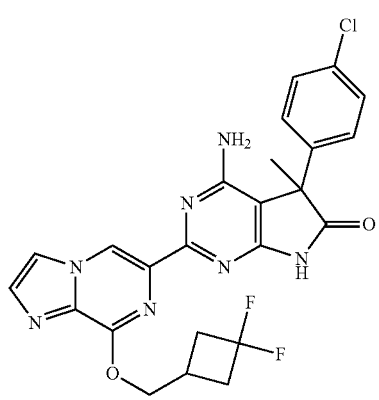 [SMILES: CC1(c2ccc(Cl)cc2)C(=O)Nc2nc(-c3cn4ccnc4c(OCC4CC(F)(F)C4)n3)nc(N)c21] | 4-amino-5-(4-chlorophenyl)-2-{8-[(3,3-difluorocyclobutyl)methoxy]imidazo[1,2-a]pyrazin-6-yl}-5-methyl-5,7-dihydro-6H-pyrrolo[2,3-d]pyrimidin-6-one | I-2A | 512.2 |

TABLE 1-continued

Examples 2A-34A

Using essentially the same procedures described in Example 1A, the following compounds in Table 1 were prepared.

| Ex No. | Structure | IUPAC Name | Chiral starting material | [M + H]+ |
|---|---|---|---|---|
| 33B | 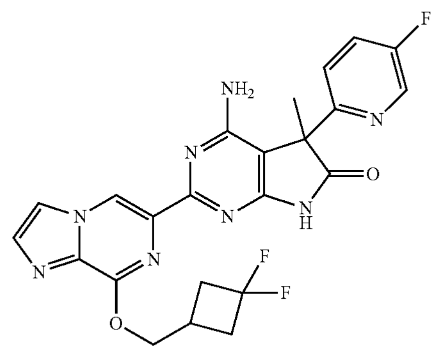 [SMILES: CC1(c2ccc(F)cn2)C(=O)Nc2nc(-c3cn4ccnc4c(OCC4CC(F)(F)C4)n3)nc(N)c21] | 4-amino-2-{8-[(3,3-difluoro-cyclobutyl)methoxy]imidazo[1,2-a]pyrazin-6-yl}-5-(5-fluoro-pyridin-2-yl)-5-methyl-5,7-dihydro-6H-pyrrolo[2,3-d]pyrimidin-6-one | I-3B | 497.2 |
| 34A | 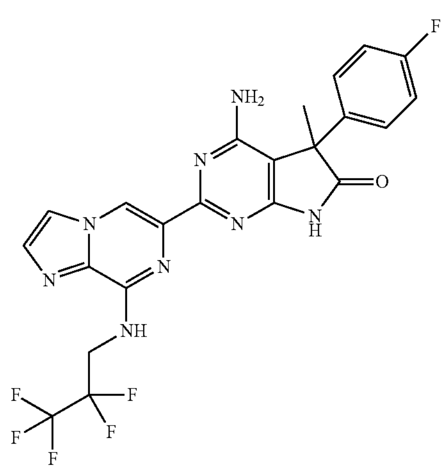 [SMILES: CC1(c2ccc(F)cc2)C(=O)Nc2nc(-c3cn4ccnc4c(NCC(F)(F)C(F)(F)F)n3)nc(N)c21] | 4-amino-5-(4-fluorophenyl)-5-methyl-2-{8-[(2,2,3,3,3-pentafluoropropyl)amino]imidazo[1,2-a]pyrazin-6-yl}-5,7-dihydro-6H-pyrrolo[2,3-d]pyrimidin-6-one | I-1A | 523.2 |

Example 35A

4-Amino-2-(8-(3-fluorophenoxy)-2-(trifluoromethyl)imidazo[1,2-a]pyrazin-6-yl)-5-(4-fluorophenyl)-5-methyl-5H-pyrrolo[2,3-d]pyrimidin-6(7H)-one

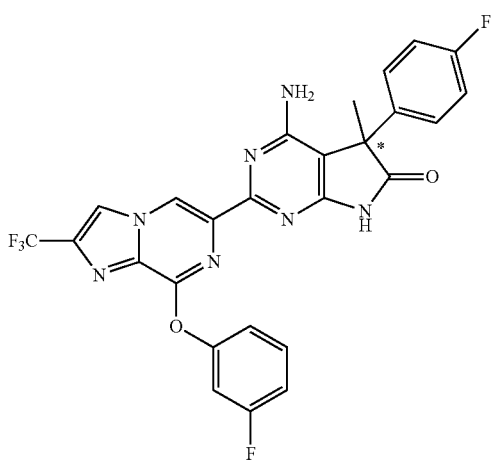 [SMILES: CC1(c2ccc(F)cc2)C(=O)Nc2nc(-c3cn4cc(C(F)(F)F)nc4c(Oc4cccc(F)c4)n3)nc(N)c21]

Step A—6,8-dibromo-2-(trifluoromethyl)imidazo[1,2-a]pyrazine

Into a flask, was placed 3,5-dibromopyrazin-2-amine (20.0 g, 79.1 mmol), DMA (100 mL), and 3-bromo-1,1,1-trifluoropropan-2-one (37.7 g, 197 mmol). The resulting solution was stirred 16 h at 90° C. The reaction was quenched by the addition of saturated sodium bicarbonate, and the resulting solution was extracted with EtOAc (3×). The combined organic layers were washed with brine (2×), dried over anhyd. $Na_2SO_4$, filtered, and concentrated in vacuo to dryness. The residue was purified by silica chromatography using EtOAc:PE (20%) to afford the title compound.

Steps B-E—4-Amino-2-(8-(3-fluorophenoxy)-2-(trifluoromethyl)imidazo[1,2-a]pyrazin-6-yl)-5-(4-fluorophenyl)-5-methyl-5H-pyrrolo[2,3-d]pyrimidin-6(7H)-one The title compound was prepared utilizing the intermediate from Step A according to the procedure described in Steps A-E of Example 1A. $^1$H NMR (300 MHz, $CDCl_3$): δ 9.06 (1H, s), 8.64 (1H, brs), 8.13 (1H, s), 7.41-7.25 (4H, m), 7.09-7.03 (2H, m), 6.97-6.92 (2H, m), 4.90 (2H, brs), 1.81 (3H, s); m/z=554 (M+H).

TABLE 2

Examples 36A-38A
Using essentially the same procedures described in example 35A, the following compounds in Table 2 were prepared.

| Ex. No. | Structure | IUPAC Name | Chiral starting material | [M + H]⁺ |
|---|---|---|---|---|
| 36A | 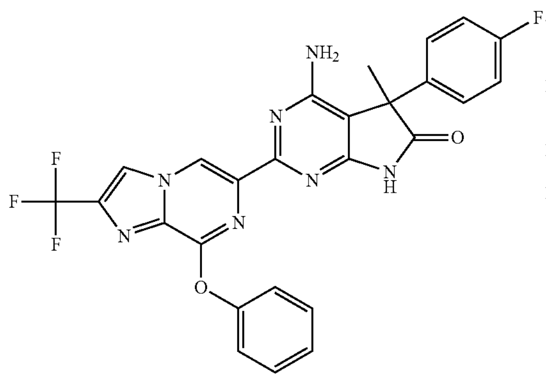 [SMILES: CC1(c2ccc(F)cc2)C(=O)Nc2nc(-c3cn4cc(C(F)(F)F)nc4c(Oc4ccccc4)n3)nc(N)c21] | 4-amino-5-(4-fluorophenyl)-5-methyl-2-(8-phenoxy-2-(trifluoromethyl)imidazo[1,2-a]pyrazin-6-yl)-5H-pyrrolo[2,3-d]pyrimidin-6(7H)-one | I-1A | 536.1 |
| 37A | 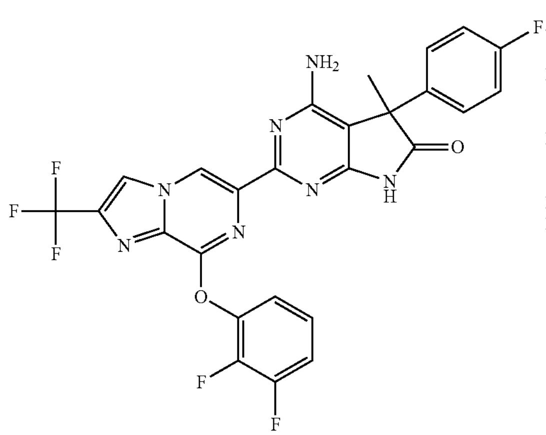 [SMILES: CC1(c2ccc(F)cc2)C(=O)Nc2nc(-c3cn4cc(C(F)(F)F)nc4c(Oc4cccc(F)c4F)n3)nc(N)c21] | 4-amino-2-(8-(2,3-difluorophenoxy)-2-(trifluoromethyl)imidazo[1,2-a]pyrazin-6-yl)-5-(4-fluorophenyl)-5-methyl-5H-pyrrolo[2,3-d]pyrimidin-6(7H)-one | I-1A | 572.0 |

TABLE 2-continued

Examples 36A-38A
Using essentially the same procedures described in example 35A, the following compounds in Table 2 were prepared.

| Ex. No. | Structure | IUPAC Name | Chiral starting material | [M + H]+ |
|---|---|---|---|---|
| 38A | 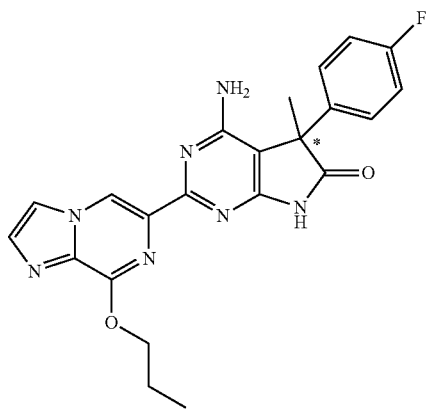 [SMILES: CCCOc1nc(-c2nc(N)c3c(n2)NC(=O)C3(C)c2ccc(F)cc2)cn2ccnc12] | 4-amino-2-[2-cyclopropyl-8-(3-fluorophenoxy)imidazo[1,2-a]pyrazin-6-yl]-5-(4-fluorophenyl)-5-methyl-5,7-dihydro-6H-pyrrolo[2,3-d]pyrimidin-6-one | I-1A | 526.1 |

Example 39A

4-Amino-5-(4-fluorophenyl)-5-methyl-2-(8-propoxyimidazo[1,2-a]pyrazin-6-yl)-5,7-dihydro-6H-pyrrolo[2,3-d]pyrimidin-6-one

Step A—8-(Methylthio)imidazo[1,2-a]pyrazine-6-carboximidamide

Into a flask, purged with an inert atmosphere of nitrogen, was placed 8-(methylthio)imidazo[1,2-a]pyrazine-6-carbonitrile (3.5 g, 18 mmol) and toluene (50 mL). To this was added amino(methyl)aluminum chloride (196 mL, 58.9 mmol, 0.3 M in toluene) and the resulting mixture was warmed at 80° C. After 16 h, the reaction mixture was cooled to 0° C. The reaction was quenched by the addition of MeOH:DCM (1:4, 200 mL). The solid was filtered through a pad of celite, and the resulting eluent was concentrated in vacuo to dryness to afford the title compound as the HCl salt.

Step B—4-Amino-5-(4-fluorophenyl)-5-methyl-2-(8-(methylthio)imidazo[1,2-a]pyrazin-6-yl)-5H-pyrrolo[2,3-d]pyrimidin-6(7H)-one Into a vial, purged with an inert atmosphere of nitrogen, was placed t-BuOH (8.8 mL), the intermediate from Step A (425 mg, 2.05 mmol), I-1A (656 mg, 2.67 mmol) and KHCO$_3$ (616 mg, 6.15 mmol). The heterogeneous mixture was stirred at 70° C. for 16 h. The reaction mixture was cooled to RT and quenched with H$_2$O (25 mL). The resulting solution was extracted with EtOAc (3×) and the organic layers were combined, and dried over anhyd. Na$_2$SO$_4$. The solid was filtered and the filtrate was concentrated in vacuo to dryness. The residue was purified by silica gel chromatography with EtOAc:hexanes (20-100%) to afford the title compound.

Step C—4-Amino-5-(4-fluorophenyl)-5-methyl-2-(8-(methylsulfonyl)imidazo[1,2-a]pyrazin-6-yl)-5H-pyrrolo[2,3-d]pyrimidin-6(7H)-one To a mixture of finely ground Oxone® (1.82 g, 2.97 mmol) in ACN (5.5 mL) was added conc. sulfuric acid (1.27 mL, 23.7 mmol) at 0° C. After 5 min, the intermediate from Step B (500 mg, 1.19 mmol) was added in a single portion. The reaction was slowly warmed to RT. After 1.5 h, saturated aqueous NaHCO$_3$ (30 mL) was added and the mixture was extracted with EtOAc (3×). The organic layers were combined and dried over Na$_2$SO$_4$. The solid was filtered and the filtrate was concentrated in vacuo to dryness to afford the title compound, which was not further purified. m/z=454.1 (M+H).

Step D—4-Amino-5-(4-fluorophenyl)-5-methyl-2-(8-propoxyimidazo[1,2-a]pyrazin-6-yl)-5,7-dihydro-6H-pyrrolo[2,3-d]pyrimidin-6-one NaH (30.4 mg, 0.761 mmol) was added to a solution of the intermediate from Step C (115 mg, 0.254 mmol) in 1-propanol (1.3 mL) at RT. After 5 min, the volatiles were removed and the residue was dissolved in EtOAc (150 mL) and washed with water (1×). The aqueous layer was extracted with EtOAc (3×). The combined organic layers were washed with saturated aqueous NH₄Cl (1×) and brine (1×), dried over anhyd. Na₂SO₄, filtered, and concentrated in vacuo to dryness. The residue was purified by silica chromatography using EtOAc:hexanes (0-100%) to afford the title compound. ¹H NMR (500 MHz, CD₃OD): δ 9.05 (1H, s), 7.99 (1H, s), 7.64 (1H, s), 7.32 (2H, dd, J=8.6, 5.2 Hz), 7.05 (2H, t, J=8.6 Hz), 4.64 (2H, t, J=6.7 Hz), 1.91-1.86 (2H, m), 1.83 (3H, s), 1.09 (3H, t, J=7.4 Hz); m/z=434.1 (M+H).

Example 40A

4-Amino-5-(4-chlorophenyl)-2-{8-[(2-methoxyethyl)amino]imidazo[1,2-a]pyrazin-6-yl}-5-methyl-5,7-dihydro-6H-pyrrolo[2,3-d]pyrimidin-6-one

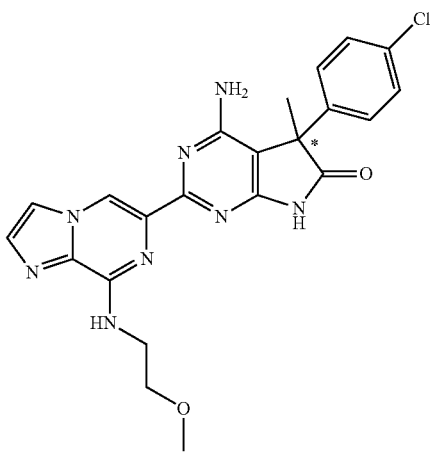 [SMILES: COCCNc1nc(-c2nc(N)c3c(n2)NC(=O)C3(C)c2ccc(Cl)cc2)cn2ccnc12]

Step A-C—4-Amino-5-(4-chlorophenyl)-5-methyl-2-(8-(methylsulfonyl)imidazo[1,2-a]pyrazin-6-yl)-5H-pyrrolo[2,3-d]pyrimidin-6(7H)-one The sulfone was prepared in its enantiopure form using essentially the same procedure as described in Example 39A with Ex-39A intermediate A and I-2A following the procedures described in steps B-C. m/z=470.0 (M+H).

Step D—4-Amino-5-(4-chlorophenyl)-2-{8-[(2-methoxyethyl)amino]imidazo[1,2-a]pyrazin-6-yl}-5-methyl-5,7-dihydro-6H-pyrrolo[2,3-d]pyrimidin-6-one Sodium hydride (18 mg, 0.45 mmol) was added to a mixture of the intermediate from Steps A-C (70 mg, 0.15 mmol) and 2-methoxyethylamine (1 mL, 0.15 mmol), at RT. After 5 min, the reaction was diluted with EtOAc (100 mL) and washed with water (1×). The aqueous layer was extracted with EtOAc (3×). The combined organic layers were washed with saturated aqueous NH₄Cl (1×) and brine (1×), dried over anhyd. Na₂SO₄, filtered, and concentrated in vacuo to dryness. The crude residue was purified by RP-HPLC with 10-60% ACN:water (0.05% TFA), followed by basifying with saturated aqueous NaHCO₃ and extraction with EtOAc to afford the title compound. ¹H NMR (500 MHz, DMSO-d₆): δ 8.54 (1H, s), 8.04 (1H, s), 7.55 (1H, s), 7.39 (2H, d, J=8.4 Hz), 7.26 (2H, d, J=8.4 Hz), 7.23 (1H, t, J=5.7 Hz), 6.30 (2H, br s), 3.75 (2H, dd, J=6.2, 6.1 Hz), 3.58 (2H, t, J=6.0 Hz), 3.29 (3H, s), 1.75 (3H, s); m/z=465.0 (M+H).

TABLE 3

Examples 41A-64A
Using essentially the same procedures described in examples 39A & 40A, the following compounds in Table 3 were prepared.

| Ex. No. | Structure | IUPAC Name | Chiral starting material | [M + H]⁺ |
|---|---|---|---|---|
| 41A | 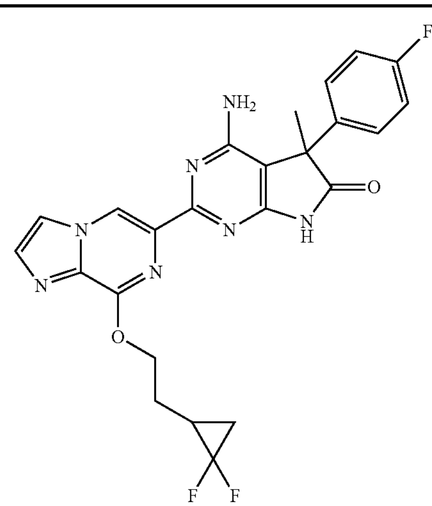 | 4-amino-2-{8-[2-(2,2-difluorocyclopropyl)ethoxy]imidazo[1,2-a]pyrazin-6-yl}-5-(4-fluorophenyl)-5-methyl-5,7-dihydro-6H-pyrrolo[2,3-d]pyrimidin-6-one | I-1A | 496.1 |

TABLE 3-continued

Examples 41A-64A
Using essentially the same procedures described in examples 39A & 40A, the following compounds in Table 3 were prepared.

| Ex. No. | Structure | IUPAC Name | Chiral starting material | [M + H]+ |
|---|---|---|---|---|
| 42A | 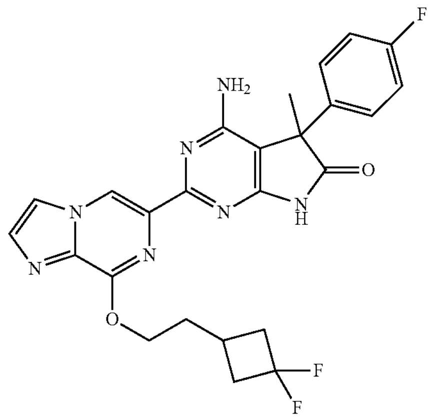 [SMILES: CC1(c2ccc(F)cc2)C(=O)Nc2nc(-c3cn4ccnc4c(OCCC4CC(F)(F)C4)n3)nc(N)c21] | 4-amino-2-{8-[2-(3,3-difluoro-cyclobutyl)ethoxy]imidazo[1,2-a]pyrazin-6-yl}-5-(4-fluorophenyl)-5-methyl-5,7-dihydro-6H-pyrrolo[2,3-d]pyrimidin-6-one | I-1A | 510.1 |
| 43A | 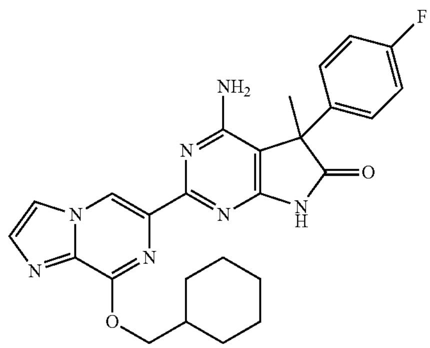 [SMILES: CC1(c2ccc(F)cc2)C(=O)Nc2nc(-c3cn4ccnc4c(OCC4CCCCC4)n3)nc(N)c21] | 4-amino-2-[8-(cyclohexyl-methoxy)imidazo[1,2-a]pyrazin-6-yl]-5-(4-fluorophenyl)-5-methyl-5,7-dihydro-6H-pyrrolo[2,3-d]pyrimidin-6-one | I-1A | 488.2 |
| 44A | 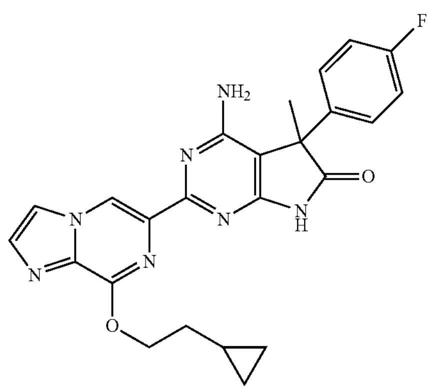 [SMILES: CC1(c2ccc(F)cc2)C(=O)Nc2nc(-c3cn4ccnc4c(OCCC4CC4)n3)nc(N)c21] | 4-amino-2-[8-(2-cyclopropyl-ethoxy)imidazo[1,2-a]pyrazin-6-yl]-5-(4-fluorophenyl)-5-methyl-5,7-dihydro-6H-pyrrolo[2,3-d]pyrimidin-6-one | I-1A | 460.1 |
| 45A | 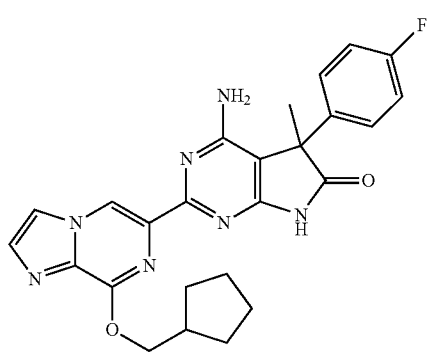 [SMILES: CC1(c2ccc(F)cc2)C(=O)Nc2nc(-c3cn4ccnc4c(OCC4CCCC4)n3)nc(N)c21] | 4-amino-2-[8-(cyclopentyl-methoxy)imidazo[1,2-a]pyrazin-6-yl]-5-(4-fluoro-phenyl)-5-methyl-5,7-dihydro-6H-pyrrolo[2,3-d]pyrimidin-6-one | I-1A | 474.2 |

TABLE 3-continued

Examples 41A-64A
Using essentially the same procedures described in examples 39A & 40A, the following compounds in Table 3 were prepared.

| Ex. No. | Structure | IUPAC Name | Chiral starting material | [M + H]+ |
|---|---|---|---|---|
| 46A | 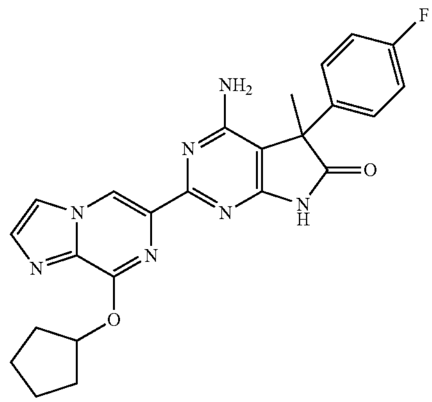 [SMILES: CC1(c2ccc(F)cc2)C(=O)Nc2nc(-c3cn4ccnc4c(OC4CCCC4)n3)nc(N)c21] | 4-amino-2-[8-(cyclopentyloxy)imidazo[1,2-a]pyrazin-6-yl]-5-(4-fluorophenyl)-5-methyl-5,7-dihydro-6H-pyrrolo[2,3-d]pyrimidin-6-one | I-1A | 460.1 |
| 47A | 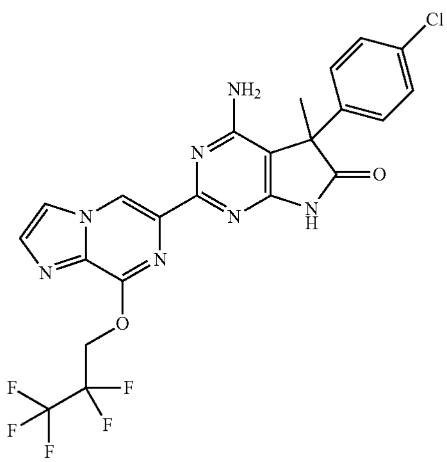 [SMILES: CC1(c2ccc(Cl)cc2)C(=O)Nc2nc(-c3cn4ccnc4c(OCC(F)(F)C(F)(F)F)n3)nc(N)c21] | 4-amino-5-(4-chlorophenyl)-5-methyl-2-[8-(2,2,3,3,3-pentafluoropropoxy)imidazo[1,2-a]pyrazin-6-yl]-5,7-dihydro-6H-pyrrolo[2,3-d]pyrimidin-6-one | I-2A | 540.0 |
| 48A | 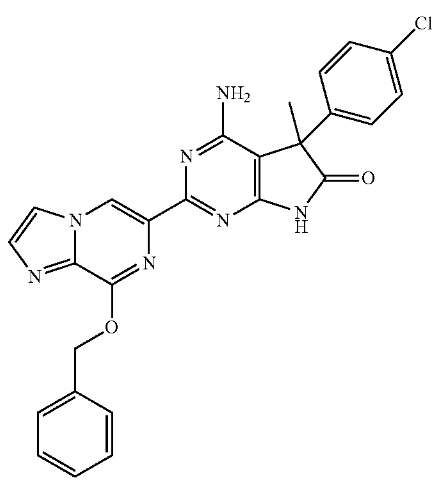 [SMILES: CC1(c2ccc(Cl)cc2)C(=O)Nc2nc(-c3cn4ccnc4c(OCc4ccccc4)n3)nc(N)c21] | 4-amino-2-[8-(benzyloxy)imidazo[1,2-a]pyrazin-6-yl]-5-(4-chlorophenyl)-5-methyl-5,7-dihydro-6H-pyrrolo[2,3-d]pyrimidin-6-one | I-2A | 498.0 |

TABLE 3-continued

Examples 41A-64A
Using essentially the same procedures described in examples 39A & 40A, the following compounds in Table 3 were prepared.

| Ex. No. | Structure | IUPAC Name | Chiral starting material | [M + H]+ |
|---|---|---|---|---|
| 49A | 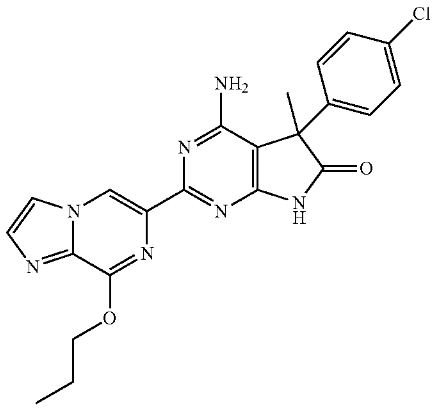 [SMILES: CCCOc1nc(-c2nc(N)c3c(n2)NC(=O)C3(C)c2ccc(Cl)cc2)cn2ccnc12] | 4-amino-5-(4-chlorophenyl)-5-methyl-2-(8-propoxyimidazo[1,2-a]pyrazin-6-yl)-5,7-dihydro-6H-pyrrolo[2,3-d]pyrimidin-6-one | I-2A | 450.1 |
| 50A | 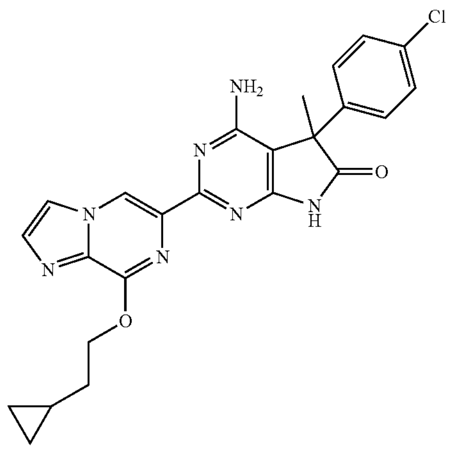 [SMILES: CC1(c2ccc(Cl)cc2)C(=O)Nc2nc(-c3cn4ccnc4c(OCCC4CC4)n3)nc(N)c21] | 4-amino-5-(4-chlorophenyl)-2-[8-(2-cyclopropylethoxy)imidazo[1,2-a]pyrazin-6-yl]-5-methyl-5,7-dihydro-6H-pyrrolo[2,3-d]pyrimidin-6-one | I-2A | 476.1 |
| 51A | 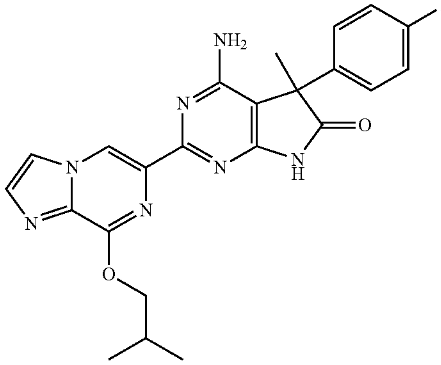 | 4-amino-5-(4-fluorophenyl)-5-methyl-2-[8-(2-methylpropoxy)imidazo[1,2-a]pyrazin-6-yl]-5,7-dihydro-6H-pyrrolo[2,3-d]pyrimidin-6-one | I-1A | 448.1 |

TABLE 3-continued

Examples 41A-64A
Using essentially the same procedures described in examples 39A & 40A, the following compounds in Table 3 were prepared.

| Ex. No. | Structure | IUPAC Name | Chiral starting material | [M + H]⁺ |
|---|---|---|---|---|
| 52A | 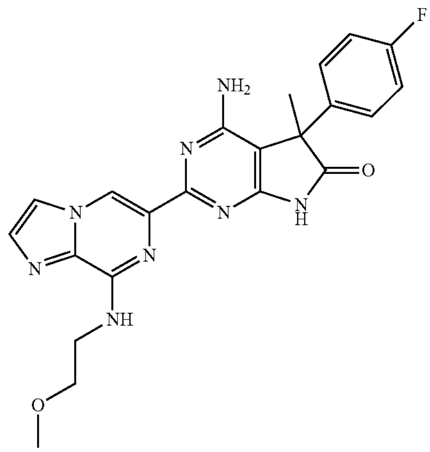 [SMILES: COCCNc1nc(-c2nc(N)c3c(n2)NC(=O)C3(C)c2ccc(F)cc2)cn2ccnc12] | 4-amino-5-(4-fluorophenyl)-2-{8-[(2-methoxyethyl)amino]imidazo[1,2-a]pyrazin-6-yl}-5-methyl-5,7-dihydro-6H-pyrrolo[2,3-d]pyrimidin-6-one | I-1A | 449.1 |
| 53A | 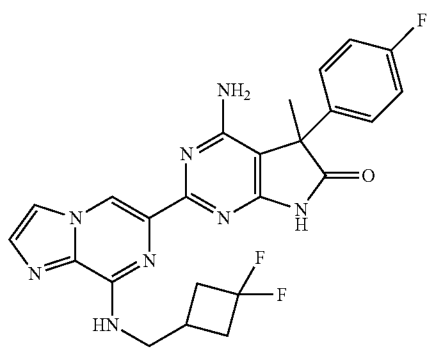 [SMILES: CC1(c2ccc(F)cc2)C(=O)Nc2nc(-c3cn4ccnc4c(NCC4CC(F)(F)C4)n3)nc(N)c21] | 4-amino-2-(8-{[(3,3-difluorocyclobutyl)methyl]amino}imidazo[1,2-a]pyrazin-6-yl)-5-(4-fluorophenyl)-5-methyl-5,7-dihydro-6H-pyrrolo[2,3-d]pyrimidin-6-one | I-1A | 495.1 |
| 54A | 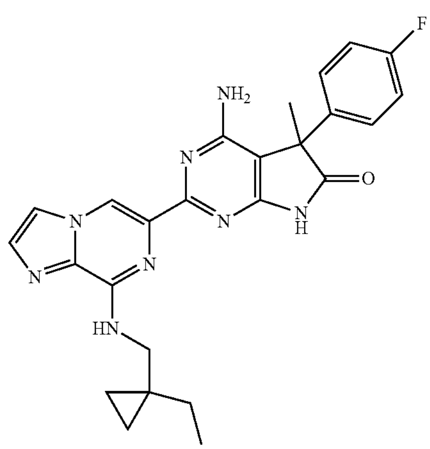 [SMILES: CCC1(CNc2nc(-c3nc(N)c4c(n3)NC(=O)C4(C)c3ccc(F)cc3)cn3ccnc23)CC1] | 4-amino-2-(8-{[(1-ethylcyclopropyl)methyl]amino}imidazo[1,2-a]pyrazin-6-yl)-5-(4-fluorophenyl)-5-methyl-5,7-dihydro-6H-pyrrolo[2,3-d]pyrimidin-6-one | I-1A | 473.0 |

TABLE 3-continued

Examples 41A-64A
Using essentially the same procedures described in examples 39A & 40A, the following compounds in Table 3 were prepared.

| Ex. No. | Structure | IUPAC Name | Chiral starting material | [M + H]+ |
|---|---|---|---|---|
| 55A | 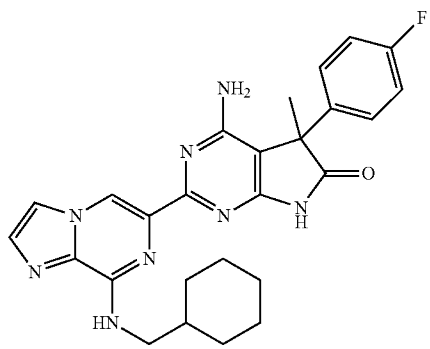 [SMILES: CC1(c2ccc(F)cc2)C(=O)Nc2nc(-c3cn4ccnc4c(NCC4CCCCC4)n3)nc(N)c21] | 4-amino-2-{8-[(cyclohexylmethyl)amino]imidazo[1,2-a]pyrazin-6-yl}-5-(4-fluorophenyl)-5-methyl-5,7-dihydro-6H-pyrrolo[2,3-d]pyrimidin-6-one | I-1A | 487.1 |
| 56A | 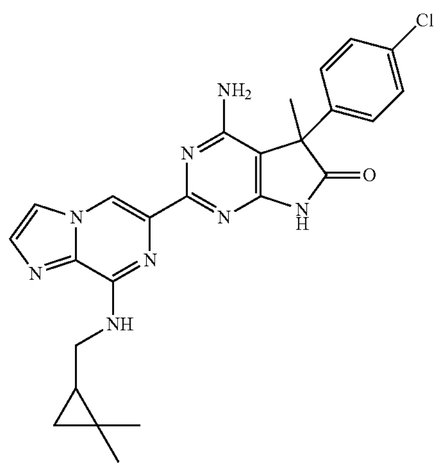 [SMILES: CC1(c2ccc(Cl)cc2)C(=O)Nc2nc(-c3cn4ccnc4c(NCC4CC4(C)C)n3)nc(N)c21] | 4-amino-5-(4-chlorophenyl)-2-(8-{[(2,2-dimethylcyclopropyl)methyl]amino}imidazo[1,2-a]pyrazin-6-yl)-5-methyl-5,7-dihydro-6H-pyrrolo[2,3-d]pyrimidin-6-one | I-2A | 489.1 |
| 57A | 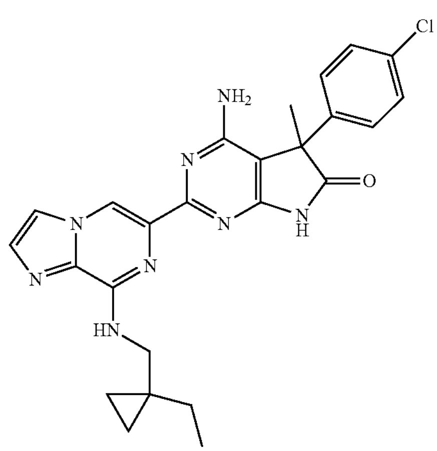 [SMILES: CCC1(CNc2nc(-c3nc(N)c4c(n3)NC(=O)C4(C)c3ccc(Cl)cc3)cn3ccnc23)CC1] | 4-amino-5-(4-chlorophenyl)-2-(8-{[(1-ethylcyclopropyl)methyl]amino}imidazo[1,2-a]pyrazin-6-yl)-5-methyl-5,7-dihydro-6H-pyrrolo[2,3-d]pyrimidin-6-one | I-2A | 489.1 |

TABLE 3-continued

Examples 41A-64A
Using essentially the same procedures described in examples 39A & 40A, the following compounds in Table 3 were prepared.

| Ex. No. | Structure | IUPAC Name | Chiral starting material | [M + H]+ |
|---------|-----------|------------|--------------------------|----------|
| 58A | 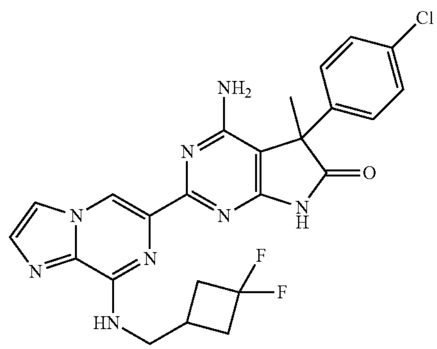 [SMILES: CC1(c2ccc(Cl)cc2)C(=O)Nc2nc(-c3cn4ccnc4c(NCC4CC(F)(F)C4)n3)nc(N)c21] | 4-amino-5-(4-chlorophenyl)-2-(8-{[(3,3-difluorocyclobutyl)methyl]amino}imidazo[1,2-a]pyrazin-6-yl)-5-methyl-5,7-dihydro-6H-pyrrolo[2,3-d]pyrimidin-6-one | I-2A | 511.1 |
| 59A | 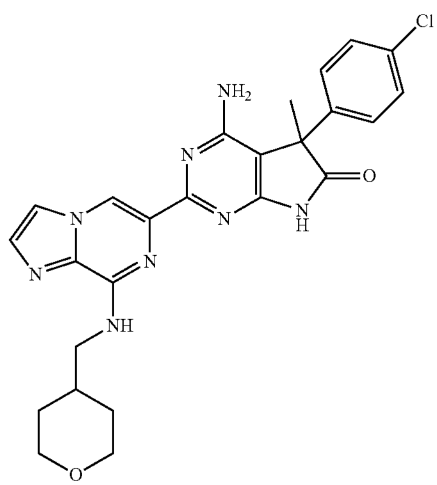 [SMILES: CC1(c2ccc(Cl)cc2)C(=O)Nc2nc(-c3cn4ccnc4c(NCC4CCOCC4)n3)nc(N)c21] | 4-amino-5-(4-chlorophenyl)-5-methyl-2-{8-[(tetrahydro-2H-pyran-4-ylmethyl)amino]imidazo[1,2-a]pyrazin-6-yl}-5,7-dihydro-6H-pyrrolo[2,3-d]pyrimidin-6-one | I-2A | 505.1 |
| 60A | 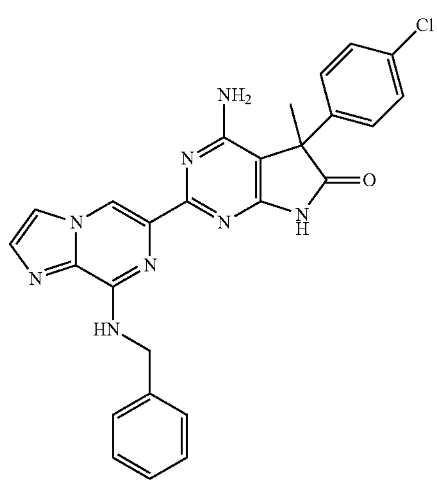 [SMILES: CC1(c2ccc(Cl)cc2)C(=O)Nc2nc(-c3cn4ccnc4c(NCc4ccccc4)n3)nc(N)c21] | 4-amino-2-[8-(benzylamino)imidazo[1,2-a]pyrazin-6-yl]-5-(4-chlorophenyl)-5-methyl-5,7-dihydro-6H-pyrrolo[2,3-d]pyrimidin-6-one | I-2A | 497.1 |

TABLE 3-continued

Examples 41A-64A
Using essentially the same procedures described in examples 39A & 40A, the following compounds in Table 3 were prepared.

| Ex. No. | Structure | IUPAC Name | Chiral starting material | [M + H]+ |
|---|---|---|---|---|
| 61A | 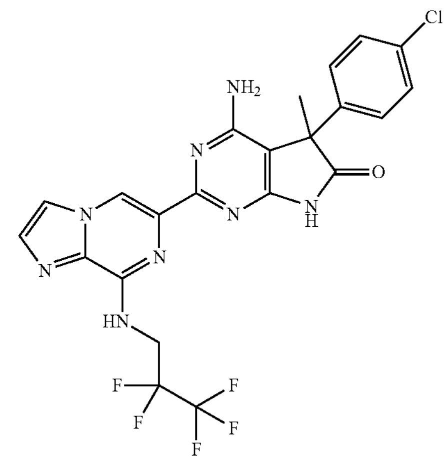 [SMILES: CC1(c2ccc(Cl)cc2)C(=O)Nc2nc(-c3cn4ccnc4c(NCC(F)(F)C(F)(F)F)n3)nc(N)c21] | 4-amino-5-(4-chlorophenyl)-5-methyl-2-{8-[(2,2,3,3,3-pentafluoropropyl)amino]imidazo[1,2-a]pyrazin-6-yl}-5,7-dihydro-6H-pyrrolo[2,3-d]pyrimidin-6-one | I-2A | 539.1 |
| 62A | 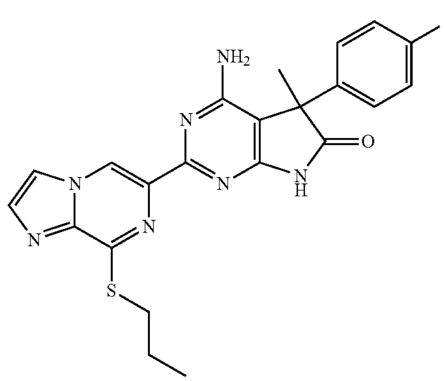 | 4-amino-5-(4-fluorophenyl)-5-methyl-2-[8-(propylsulfanyl)imidazo[1,2-a]pyrazin-6-yl]-5,7-dihydro-6H-pyrrolo[2,3-d]pyrimidin-6-one | I-1A | 450.0 |
| 63A | 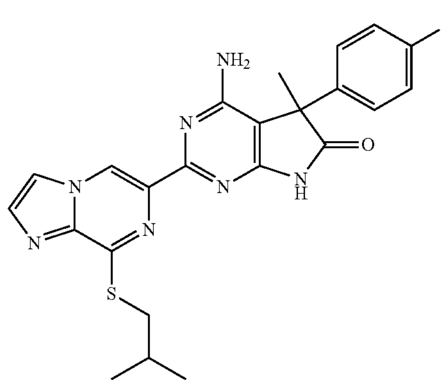 | 4-amino-5-(4-fluorophenyl)-5-methyl-2-{8-[(2-methylpropyl)sulfanyl]imidazo[1,2-a]pyrazin-6-yl}-5,7-dihydro-6H-pyrrolo[2,3-d]pyrimidin-6-one | I-1A | 464.2 |

TABLE 3-continued

Examples 41A-64A
Using essentially the same procedures described in examples 39A & 40A, the following compounds in Table 3 were prepared.

| Ex. No. | Structure | IUPAC Name | Chiral starting material | [M + H]+ |
|---|---|---|---|---|
| 64A | 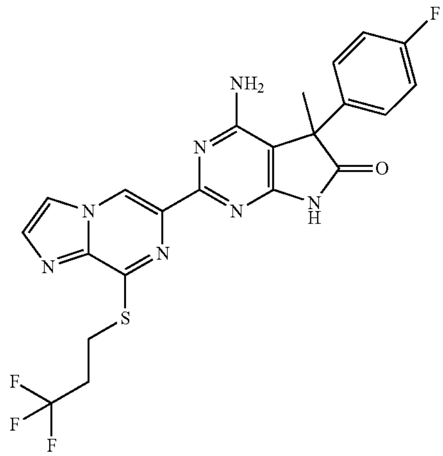 [SMILES: CC1(c2ccc(F)cc2)C(=O)Nc2nc(-c3cn4ccnc4c(SCCC(F)(F)F)n3)nc(N)c21] | 4-amino-5-(4-fluorophenyl)-5-methyl-2-{8-[(3,3,3-trifluoropropyl)sulfanyl]imidazo[1,2-a]pyrazin-6-yl}-5,7-dihydro-6H-pyrrolo[2,3-d]pyrimidin-6-one | I-1A | 504.1 |

TABLE 4

Examples 65A-74
Using essentially the same procedures described in examples 39A-40A, the following compounds in Table 4 were prepared. These compounds began with chiral intermediate and contain a second stereocenter. For some examples the diasteoromers were separated or the chiral source was purchased.

| Ex. No. | Structure | IUPAC Name | Chiral source or chiral resolution column | [M + H]+ |
|---|---|---|---|---|
| 65A | 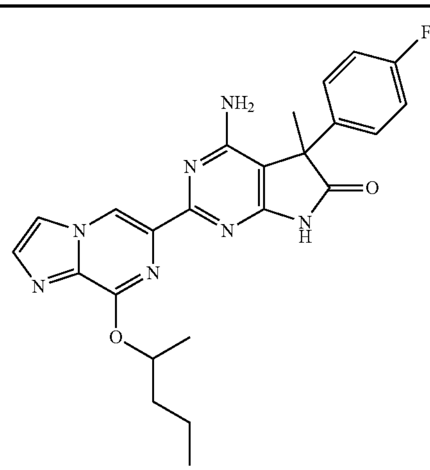 | 4-amino-5-(4-fluorophenyl)-5-methyl-2-[8-(1-methylbutoxy)imidazo[1,2-a]pyrazin-6-yl]-5,7-dihydro-6H-pyrrolo[2,3-d]pyrimidin-6-one | (rac)-2-pentanol | 462.1 |

TABLE 4-continued

Examples 65A-74
Using essentially the same procedures described in examples 39A-40A, the following compounds in Table 4 were prepared. These compounds began with chiral intermediate and contain a second stereocenter. For some examples the diasteoromers were separated or the chiral source was purchased.

| Ex. No. | Structure | IUPAC Name | Chiral source or chiral resolution column | [M + H]+ |
|---|---|---|---|---|
| 66A | 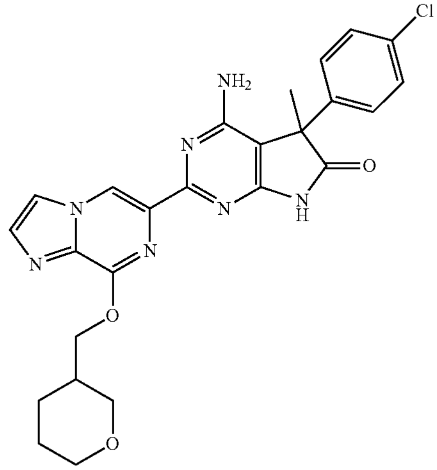 [SMILES: CC1(c2ccc(Cl)cc2)C(=O)Nc2nc(-c3cn4ccnc4c(OCC4CCCOC4)n3)nc(N)c21] | 4-amino-5-(4-chlorophenyl)-5-methyl-2-[8-(tetrahydro-2H-pyran-3-ylmethoxy)imidazo[1,2-a]pyrazin-6-yl]-5,7-dihydro-6H-pyrrolo[2,3-d]pyrimidin-6-one (fast eluting) | CHIRALPAK IC | 506.1 |
| 67B | 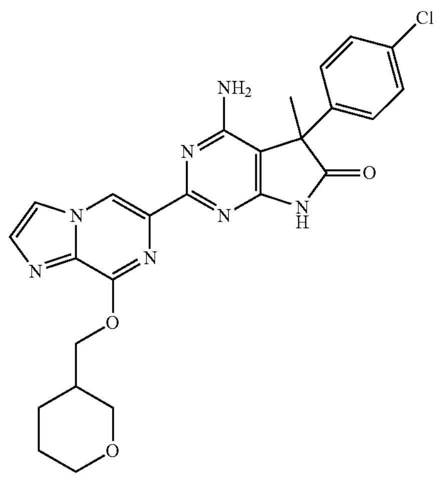 [SMILES: CC1(c2ccc(Cl)cc2)C(=O)Nc2nc(-c3cn4ccnc4c(OCC4CCCOC4)n3)nc(N)c21] | 4-amino-5-(4-chlorophenyl)-5-methyl-2-[8-(tetrahydro-2H-pyran-3-ylmethoxy)imidazo[1,2-a]pyrazin-6-yl]-5,7-dihydro-6H-pyrrolo[2,3-d]pyrimidin-6-one (slow eluting) | CHIRALPAK IC | 506.1 |
| 68A | 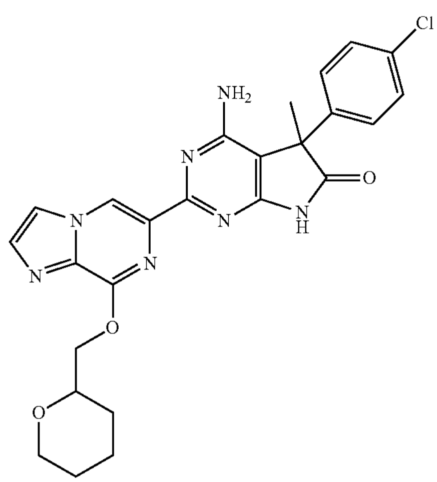 [SMILES: CC1(c2ccc(Cl)cc2)C(=O)Nc2nc(-c3cn4ccnc4c(OCC4CCCCO4)n3)nc(N)c21] | 4-amino-5-(4-chlorophenyl)-5-methyl-2-[8-(tetrahydro-2H-pyran-2-ylmethoxy)imidazo[1,2-a]pyrazin-6-yl]-5,7-dihydro-6H-pyrrolo[2,3-d]pyrimidin-6-one (fast eluting) | CHIRALPAK AS | 506.1 |

US 10,245,264 B2

TABLE 4-continued

Examples 65A-74
Using essentially the same procedures described in examples 39A-40A, the following compounds in Table 4 were prepared. These compounds began with chiral intermediate and contain a second stereocenter. For some examples the diasteoromers were separated or the chiral source was purchased.

| Ex. No. | Structure | IUPAC Name | Chiral source or chiral resolution column | [M + H]⁺ |
|---|---|---|---|---|
| 68B | 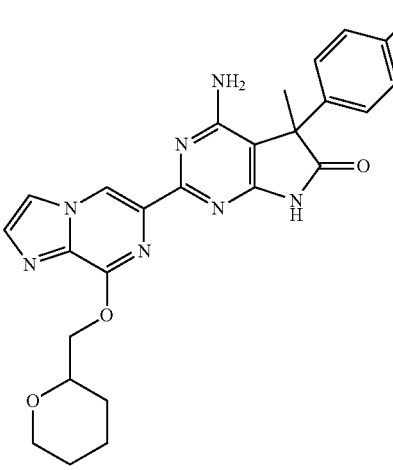 | 4-amino-5-(4-chlorophenyl)-5-methyl-2-[8-(tetrahydro-2H-pyran-2-ylmethoxy)imidazo[1,2-a]pyrazin-6-yl]-5,7-dihydro-6H-pyrrolo[2,3-d]pyrimidin-6-one (slow eluting) | CHIRALPAK AS | 506.1 |
| 69A | 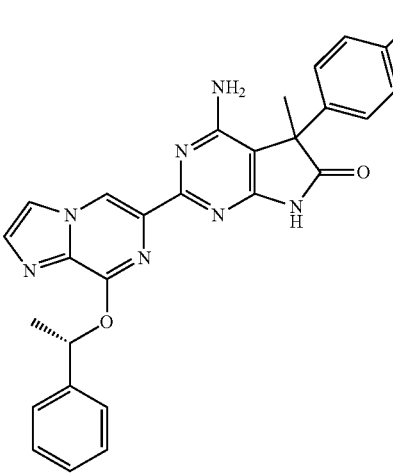 | 4-amino-5-(4-chlorophenyl)-5-methyl-2-{8-[(1S)-1-phenylethoxy]imidazo[1,2-a]pyrazin-6-yl}-5,7-dihydro-6H-pyrrolo[2,3-d]pyrimidin-6-one (fast eluting) | (S)-1-phenyl-ethanol | 512.1 |

TABLE 4-continued

Examples 65A-74
Using essentially the same procedures described in examples 39A-40A, the following compounds in Table 4 were prepared. These compounds began with chiral intermediate and contain a second stereocenter. For some examples the diasteoromers were separated or the chiral source was purchased.

| Ex. No. | Structure | IUPAC Name | Chiral source or chiral resolution column | [M + H]+ |
|---|---|---|---|---|
| 70 | 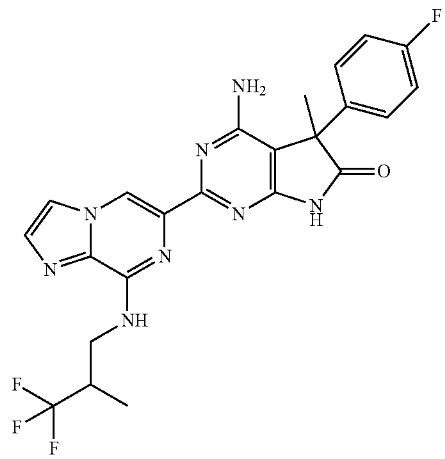 [SMILES: CC(CNc1nc(-c2nc(N)c3c(n2)NC(=O)C3(C)c2ccc(F)cc2)cn2ccnc12)C(F)(F)F] | 4-amino-5-(4-fluorophenyl)-5-methyl-2-{8-[(3,3,3-trifluoro-2-methylpropyl)amino]imidazo[1,2-a]pyrazin-6-yl}-5,7-dihydro-6H-pyrrolo[2,3-d]pyrimidin-6-one | (rac) 3,3,3-trifluoro-2-methylpropan-1-amine | 501.2 |
| 71A | 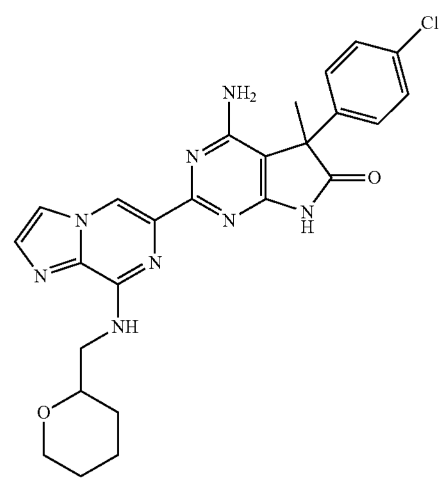 [SMILES: CC1(c2ccc(Cl)cc2)C(=O)Nc2nc(-c3cn4ccnc4c(NCC4CCCCO4)n3)nc(N)c21] | 4-amino-5-(4-chlorophenyl)-5-methyl-2-{8-[(tetrahydro-2H-pyran-2-ylmethyl)amino]imidazo[1,2-a]pyrazin-6-yl}-5,7-dihydro-6H-pyrrolo[2,3-d]pyrimidin-6-one (fast eluting) | CHIRALPAK AS | 505.1 |
| 71B | 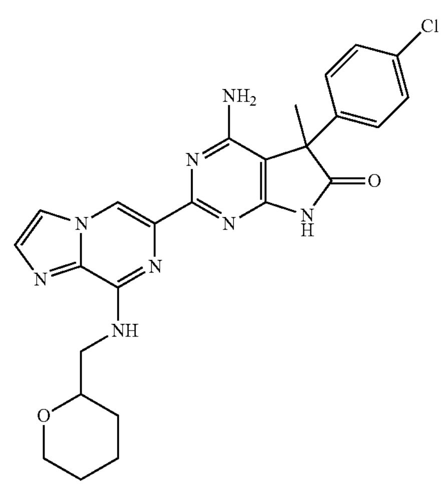 [SMILES: CC1(c2ccc(Cl)cc2)C(=O)Nc2nc(-c3cn4ccnc4c(NCC4CCCCO4)n3)nc(N)c21] | 4-amino-5-(4-chlorophenyl)-5-methyl-2-{8-[(tetrahydro-2H-pyran-2-ylmethyl)amino]imidazo[1,2-a]pyrazin-6-yl}-5,7-dihydro-6H-pyrrolo[2,3-d]pyrimidin-6-one (slow eluting) | CHIRALPAK AS | 505.1 |

TABLE 4-continued

Examples 65A-74

Using essentially the same procedures described in examples 39A-40A, the following compounds in Table 4 were prepared. These compounds began with chiral intermediate and contain a second stereocenter. For some examples the diasteoromers were separated or the chiral source was purchased.

| Ex. No. | Structure | IUPAC Name | Chiral source or chiral resolution column | [M + H]⁺ |
|---|---|---|---|---|
| 72A | 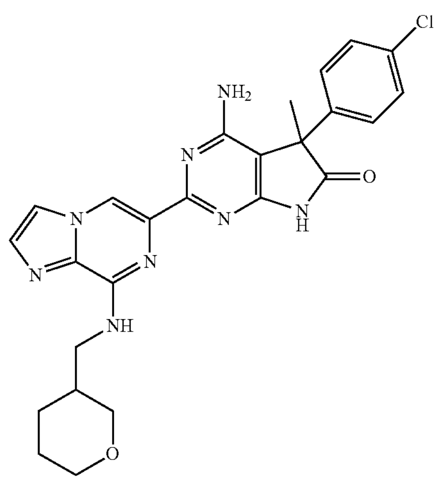 [SMILES: CC1(c2ccc(Cl)cc2)C(=O)Nc2nc(-c3cn4ccnc4c(NCC4CCCOC4)n3)nc(N)c21] | 4-amino-5-(4-chlorophenyl)-5-methyl-2-{8-[(tetrahydro-2H-pyran-3-ylmethyl)amino]imidazo[1,2-a]pyrazin-6-yl}-5,7-dihydro-6H-pyrrolo[2,3-d]pyrimidin-6-one (fast eluting) | CHIRALPAK IC | 505.1 |
| 72B | 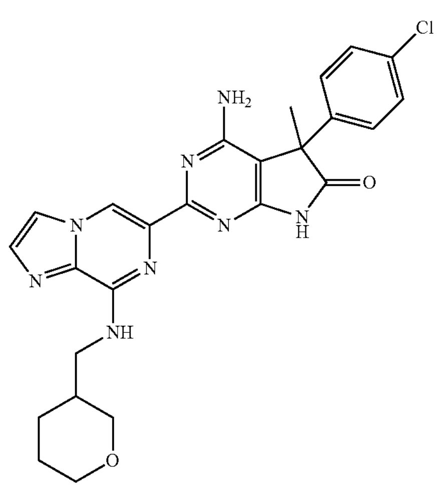 [SMILES: CC1(c2ccc(Cl)cc2)C(=O)Nc2nc(-c3cn4ccnc4c(NCC4CCCOC4)n3)nc(N)c21] | 4-amino-5-(4-chlorophenyl)-5-methyl-2-{8-[(tetrahydro-2H-pyran-3-ylmethyl)amino]imidazo[1,2-a]pyrazin-6-yl}-5,7-dihydro-6H-pyrrolo[2,3-d]pyrimidin-6-one (slow eluting) | CHIRALPAK IC | 505.1 |

TABLE 4-continued

Examples 65A-74
Using essentially the same procedures described in examples 39A-40A, the following compounds in Table 4 were prepared. These compounds began with chiral intermediate and contain a second stereocenter. For some examples the diasteoromers were separated or the chiral source was purchased.

| Ex. No. | Structure | IUPAC Name | Chiral source or chiral resolution column | [M + H]+ |
|---|---|---|---|---|
| 73 | 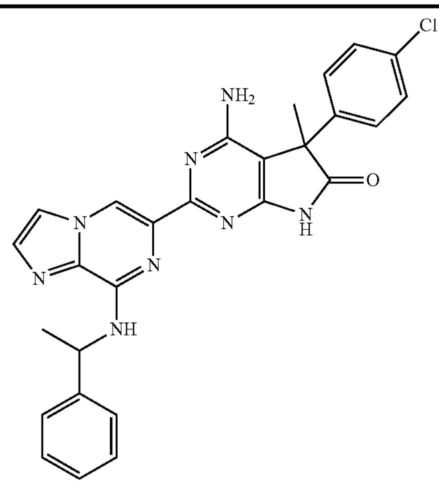 | 4-amino-5-(4-chlorophenyl)-5-methyl-2-{8-[(1-phenylethyl)amino]imidazo[1,2-a]pyrazin-6-yl}-5,7-dihydro-6H-pyrrolo[2,3-d]pyrimidin-6-one | (R)-(+)-1-phenylethylamine | 511.2 |
| 74 | 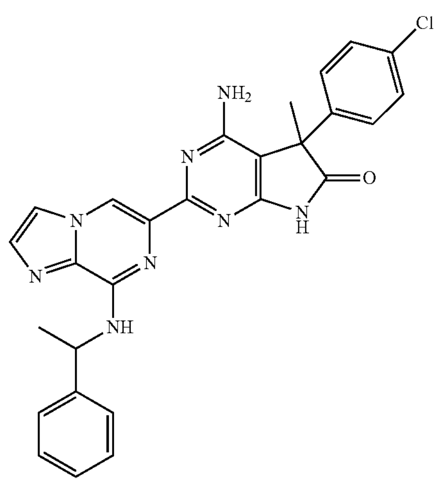 [SMILES: CC(Nc1nc(-c2nc(N)c3c(n2)NC(=O)C3(C)c2ccc(Cl)cc2)cn2ccnc12)c1ccccc1] | 4-amino-5-(4-chlorophenyl)-5-methyl-2-{8-[(1-phenylethyl)amino]imidazo[1,2-a]pyrazin-6-yl}-5,7-dihydro-6H-pyrrolo[2,3-d]pyrimidin-6-one | (S)-(−)-1-phenylethylamine | 511.2 |

Biological Assay 1: Cell-Based sGC Functional Assay (CASA Assay) Rationale sGC is a heme-containing enzyme that converts GTP to secondary messenger cGMP. Increases in cGMP levels affect several physiological processes including vasorelaxation through multiple downstream pathways. The rate by which sGC catalyzes cGMP formation is greatly increased by NO and by recently discovered NO-independent activators and stimulators. Heme-dependent activators (HDAs) preferentially activate sGC containing a ferrous heme group. To determine the effect of sGC activators on enzyme activity, the CASA assay was developed to monitor the generation of cGMP in a cell line that stably expresses the heterodimeric sGC protein.

Methods

A CHO-K1 cell line stably expressing the sGC α1/β1 heterodimer was generated using a standard transfection protocol. CHO-K1 cells were transfected with plasmids pIREShyghsGCα1 and pIRESneo-hsGCβ1 simultaneously using FUGENE reagent. Clones that stably express both subunits were selected with hygromycin and neomycin for ~2 weeks. Clone #7 was chosen for the assay and was designated CHO-K1/sGC. CHO-K1/sGC cells were maintained in F-K12 medium containing 10% heat-inactivated Fetal Bovine Serum (FBS), 100 μg/mL penicillin/streptomycin, 0.5 mg/mL hygromycin and 0.25 mg/mL G418. The cells were then cryopreserved in LN2. On the day of the assay, cells were thawed and resuspended in EBSS Assay Buffer (Sigma, E3024) supplemented with 5 mM $MgCl_2$, 10 mM HEPES (4-(2-hydroxyethyl)piperazine-1-ethanesulfonic acid) and 0.05% BSA (bovine serum albumin) (EAB) and cell density was then adjusted to 4×105/mL with EAB. IBMX (3-isobutyl-1-methylxanthin, 0.5 mM) was added to inhibit degradation of cGMP. Compounds were diluted from DMSO stock solutions and added to the assay at a final DMSO concentration of 2.5%. Cells were incubated with compounds in the presence and absence of 1 µM of Diethylenetriamine/nitric oxide adduct (DETA-NO; Sigma, 17018) for 1 hr at 37° C. At the end of the incubation period, the reaction was terminated and the cells were lysed with the detection reagents from Cisbio Kits. The level of intracellular cGMP was determined using an HTRF-based assay kit (CisBio, 62GM2PEC), which detects the displacement of a fluorescence labeled cGMP from its specific antibody. The cGMP produced by test compounds was directly compared to the maximum cGMP production (this value was set to equal 100% activation.) of the published sGC-HDA Compound A:

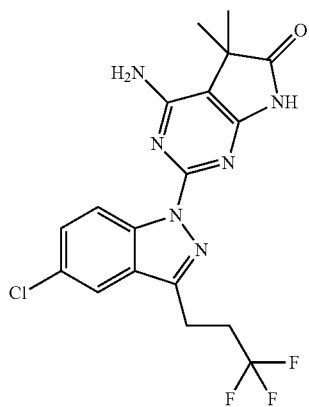

Compound A (Example 1 in WO 2010/065275, published Jun. 10, 2010). The test compounds' activities were then expressed as a percentage of Compound A, the standard in every experiment. This percent activation was calculated either in the presence or absence of DETA-NO which was then plotted. IP and maximum fold induction was derived using ADA analysis software for 4P fit.

The compounds in the Examples of the instant invention had inflection points (IP) less than or equal to 10 µM and many had IPs less than or equal to about 1 µM. Most preferred compounds had an IP of less than or equal to about 500 nM. Data for the compounds of the Examples is provided in Table 5.

TABLE 5

| Ex. No. | IP (nM) | % Act. |
|---|---|---|
| 1A | 17 | 110 |
| 2A | 317 | 127 |
| 3B | 416 | 97 |
| 4A | 62 | 100 |
| 5B | 80 | 107 |
| 6A | 499 | 89 |
| 7B | 1025 | 112 |
| 8B | 22 | 110 |
| 9A | 28 | 124 |
| 10B | 45 | 127 |
| 11B | 138 | 104 |
| 12B | 47 | 99 |
| 13B | 14 | 109 |
| 14B | 534 | 96 |
| 15A | 23 | 104 |
| 16A | 37 | 89 |
| 17A | 17 | 100 |
| 18A | 10 | 98 |
| 19A | 74 | 109 |

TABLE 5-continued

| Ex. No. | IP (nM) | % Act. |
|---|---|---|
| 20A | 42 | 109 |
| 21A | 1065 | 137 |
| 22A | 171 | 107 |
| 23A | 16 | 100 |
| 24 | 238 | 89 |
| 25A | 32 | 97 |
| 26 | 718 | 105 |
| 27A | 47 | 128 |
| 28A | 1164 | 139 |
| 29A | 422 | 158 |
| 30A | 171 | 168 |
| 31A | 145 | 98 |
| 32A | 157 | 129 |
| 33B | 1035 | 112 |
| 34A | 164 | 117 |
| 35A | 468 | 94 |
| 36A | 1473 | 129 |
| 37A | 719 | 83 |
| 38A | 748 | 92 |
| 39A | 148 | 109 |
| 40A | 85 | 117 |
| 41A | 644 | 94 |
| 42A | 1346 | 119 |
| 43A | 17 | 116 |
| 44A | 60 | 100 |
| 45A | 13 | 110 |
| 46A | 912 | 108 |
| 47A | 157 | 91 |
| 48A | 26 | 106 |
| 49A | 30 | 117 |
| 50A | 12 | 106 |
| 51A | 27 | 127 |
| 52A | 244 | 101 |
| 53A | 948 | 110 |
| 54A | 266 | 98 |
| 55A | 35 | 92 |
| 56A | 51 | 110 |
| 57A | 47 | 123 |
| 58A | 163 | 109 |
| 59A | 701 | 167 |
| 60A | 7 | 72 |
| 61A | 165 | 116 |
| 62A | 142 | 99 |
| 63A | 10 | 93 |
| 64A | 73 | 67 |
| 65A | 461 | 101 |
| 66A | 1706 | 115 |
| 67B | 501 | 94 |
| 68A | 324 | 86 |
| 68B | 633 | 85 |
| 69A | 833 | 103 |
| 70 | 291 | 89 |
| 71A | 175 | 96 |
| 71B | 143 | 95 |
| 72A | 1076 | 96 |
| 72B | 412 | 94 |
| 73 | 336 | 81 |
| 74 | 231 | 87 |

Acute Efficacy in Spontaneously Hypertensive Rats (SHR)

Spontaneously hypertensive rats (SHR, male, Charles River) were implanted with DSI TA11 PA-C40 telemetry device (Data Sciences, Inc., St. Paul, Minn.) under isoflurane or ketamine/metomidine anesthesia. The telemetry unit catheter was inserted into the descending aorta via the femoral artery and the telemetry device was implanted subcutaneously in the left flank area. Animals were allowed to recover from surgery for 14 days before the start of any studies. Blood pressure, heart rate, and activity signals from conscious, freely moving rats were recorded continuously for 30 seconds every 10 minutes. On the day prior to administration of compound, a single oral dose of vehicle (10% transcutol/20% Cremophor/70% water) was administered to all animals to establish baseline control data. The blood pressure lowering efficacy of compound (PO) or vehicle was evaluated following a single oral gavage. Data were collected as hourly averages, and changes in blood pressure were calculated by subtracting control baseline data on an hourly basis. Animals were maintained on normal diet with a 12 hour light-dark cycle.

Maximum peak decreases of systolic blood pressure (SBP) in SHR at a particular P.O. dose (mpk milligrams per kilogram) for the following representative compounds are provided below in Table 6.

Category A=SBP in SHRs <20 mmHg; Category B=SBP in SHRs 20-40 mmHg;
Category C=SBP in SHRs >40 mmHg

TABLE 6

| Ex. No. | Dose, P.O. mpk | Category |
|---|---|---|
| 1A | 0.3 | B |
| 2A | 3.0 | B |
| 4A | 1.0 | C |
| 10B | 0.3 | B |
| 30A | 1.0 | B |
| 32A | 1.0 | B |
| 34A | 3.0 | A |
| 39A | 1.0 | C |
| 40A | 1.0 | B |
| 47A | 1.0 | B |
| 49A | 0.3 | B |
| 50A | 0.3 | B |
| 51A | 0.3 | B |
| 61A | 3.0 | B |
| 62A | 1.0 | B |

What is claimed is:

1. A compound having structural Formula I:

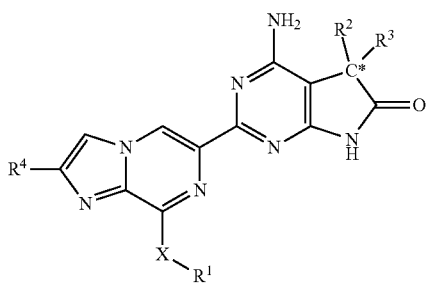

or a pharmaceutically acceptable salt thereof, wherein:
C* indicates a potential chiral carbon atom;
X is
 (1) O, or
 (2) NH;
$R^1$ is
 (1) phenyl unsubstituted or substituted by 1, 2, or 3 halo,
 (2) $(C_{1-6})$alkyl unsubstituted or substituted by $(C_{1-3})$alkyl,
 (3) halo$(C_{1-6})$alkyl,
 (4) $(C_{3-7})$cycloalkyl unsubstituted or substituted by 1 or 2 halo,
 (5) 5- or 6-membered heteroaryl containing 1, 2, or 3 heteroatoms independently selected from N, O and S, wherein the heteroaryl is unsubstituted or substituted by 1 or 2 halo, $(C_{1-3})$alkyl, or halo$(C_{1-3})$alkyl,
 (6) —$(C_{1-3})$alkyl-$(C_{3-7})$cycloalkyl, wherein the cycloalkyl is unsubstituted or substituted by 1 or 2 $(C_{1-3})$alkyl, or halo,
 (7) —$(C_{1-3})$alkyl-phenyl, wherein phenyl is unsubstituted or substituted by 1, 2, or 3 halo, or
 (8) —$(C_{1-3})$alkyl-heterocyclyl containing 1 or 2 heteroatoms independently selected from N and O, wherein the heterocyclyl is a 4-7 membered ring;
$R^2$ is
 (1) $(C_{1-3})$alkyl, or
 (2) $(C_{3-7})$cycloalkyl;
$R^3$ is
 (1) phenyl unsubstituted or substituted by 1 or 2 halo,
 (2) 5- or 6-membered heteroaryl containing 1, 2, or 3 heteroatoms independently selected from N, O and S, wherein heteroaryl is unsubstituted or substituted by 1 or 2 halo, or
 (3) $(C_{1-6})$alkyl; and
$R^4$ is
 (1) hydrogen,
 (2) $(C_{1-3})$alkyl,
 (3) halo$(C_{1-3})$alkyl, or
 (4) $(C_{3-6})$cycloalkyl.

2. The compound of claim 1, or a pharmaceutically acceptable salt thereof, wherein: $R^1$ is $(C_{1-6})$alkyl; halo$(C_{1-6})$alkyl; $(C_{3-7})$cycloalkyl unsubstituted or substituted by 1 to 2 halo; —$(C_{1-3})$alkyl-$(C_{3-7})$cycloalkyl, wherein the cycloalkyl is unsubstituted or substituted by 1 or 2 $(C_{1-3})$alkyl, or halo; or —$(C_{1-3})$alkyl-heterocyclyl containing 1 or 2 heteroatoms independently selected from N and O, wherein the heterocyclyl is a 4-7 membered ring.

3. The compound of claim 2, or a pharmaceutically acceptable salt thereof, wherein: $R^3$ is phenyl unsubstituted or substituted by 1 or 2 halo.

4. The compound of claim 2, or a pharmaceutically acceptable salt thereof, wherein: $R^3$ is 6-membered heteroaryl containing 1 or 2 N heteroatoms, wherein heteroaryl is unsubstituted or substituted by 1 or 2 halo.

5. The compound of claim 2, or a pharmaceutically acceptable salt thereof, wherein: $R^3$ is $(C_{1-6})$alkyl.

6. The compound of claim 1, or a pharmaceutically acceptable salt thereof, wherein $R^1$ is phenyl unsubstituted or substituted by 1, 2, or 3 halo; 6-membered heteroaryl containing 1 or 2 N heteroatoms, wherein the heteroaryl is unsubstituted or substituted by 1 or 2 halo, $(C_{1-3})$alkyl, or halo$(C_{1-3})$alkyl; or —$(C_{1-3})$alkyl-phenyl, wherein phenyl is unsubstituted or substituted by 1, 2, or 3 halo.

7. The compound of claim 6, or a pharmaceutically acceptable salt thereof, wherein: $R^3$ is phenyl unsubstituted or substituted by 1 or 2 halo.

8. The compound of claim 6, or a pharmaceutically acceptable salt thereof, wherein: $R^3$ is 6-membered heteroaryl containing 1 or 2 N, wherein heteroaryl is unsubstituted or substituted by 1 or 2 halo.

9. The compound of claim 6, or a pharmaceutically acceptable salt thereof, wherein: $R^3$ is $(C_{1-6})$alkyl.

10. The compound of claim 1, or a pharmaceutically acceptable salt thereof, wherein: X is O.

11. The compound of claim 1, or a pharmaceutically acceptable salt thereof, wherein: X is NH.

12. A pharmaceutical composition comprising the compound of claim 1, or a pharmaceutically acceptable salt thereof, and a pharmaceutically acceptable carrier.

13. The pharmaceutical composition of claim 12, wherein the pharmaceutical composition further comprises one or more additional active agents.

14. The pharmaceutical composition of claim 13, wherein the one or more additional active agents is selected from the group consisting of an angiotensin converting enzyme inhibitor, an angiotensin II receptor antagonist, a neutral endopeptidase inhibitor, an aldosterone antagonist, a renin inhibitor, an endothelin receptor antagonist, an aldosterone synthase inhibitor, a phosphodiesterase-5 inhibitor, a vasodilator, a calcium channel blocker, a potassium channel activator, a diuretic, a sympatholytic, a beta-adrenergic blocking drug, an alpha adrenergic blocking drug, a central alpha adrenergic agonist, a peripheral vasodilator, a lipid lowering agent and a metabolic altering agent.

15. A method for activating soluble guanylate cyclase in a patient in need thereof, comprising administering to the patient a therapeutically effective amount of the compound of claim 1, or a pharmaceutically acceptable salt thereof.

16. A method for treating hypertension in a patient in need thereof, comprising administering to the patient a therapeutically effective amount of the compound of claim 1, or a pharmaceutically acceptable salt thereof.

17. A method for treating heart failure in a patient in need thereof, comprising administering to the patient a therapeutically effective amount of the compound of claim 1, or a pharmaceutically acceptable salt thereof.

18. A compound selected from the group consisting of:
4-Amino-2-[8-(3-fluorophenoxy)imidazo[1,2-a]pyrazin-6-yl]-5-(4-fluorophenyl)-5-methyl-5,7-dihydro-6H-pyrrolo[2,3-d]pyrimidin-6-one,
4-amino-5-(4-fluorophenyl)-5-methyl-2-[8-(2,2,3,3,3-pentafluoropropoxy)imidazo[1,2-a]pyrazin-6-yl]-5,7-dihydro-6H-pyrrolo[2,3-d]pyrimidin-6-one,
4-amino-5-methyl-2-[8-(2,2,3,3,3-pentafluoropropoxy)imidazo[1,2-a]pyrazin-6-yl]-5-phenyl-5,7-dihydro-6H-pyrrolo[2,3-d]pyrimidin-6-one,
4-amino-2-[8-(2-fluorophenoxy)imidazo[1,2-a]pyrazin-6-yl]-5-(4-fluorophenyl)-5-methyl-5,7-dihydro-6H-pyrrolo[2,3-d]pyrimidin-6-one,
4-amino-2-[8-(2-fluorophenoxy)imidazo[1,2-a]pyrazin-6-yl]-5-methyl-5-phenyl-5,7-dihydro-6H-pyrrolo[2,3-d]pyrimidin-6-one,
4-amino-5-(4-fluorophenyl)-5-methyl-2-[8-(2,3,6-trifluorophenoxy)imidazo[1,2-a]pyrazin-6-yl]-5,7-dihydro-6H-pyrrolo[2,3-d]pyrimidin-6-one,
4-amino-5-methyl-5-phenyl-2-[8-(2,3,6-trifluorophenoxy)imidazo[1,2-a]pyrazin-6-yl]-5,7-dihydro-6H-pyrrolo[2,3-d]pyrimidin-6-one,
4-amino-2-[8-(3-fluorophenoxy)imidazo[1,2-a]pyrazin-6-yl]-5-methyl-5-phenyl-5,7-dihydro-6H-pyrrolo[2,3-d]pyrimidin-6-one,
4-amino-5-(4-fluorophenyl)-5-methyl-2-(8-phenoxyimidazo[1,2-a]pyrazin-6-yl)-5,7-dihydro-6H-pyrrolo[2,3-d]pyrimidin-6-one,
4-amino-5-methyl-2-(8-phenoxyimidazo[1,2-a]pyrazin-6-yl)-5-phenyl-5,7-dihydro-6H-pyrrolo[2,3-d]pyrimidin-6-one,
4-amino-5-methyl-5-phenyl-2-[8-(2,3,4-trifluorophenoxy)imidazo[1,2-a]pyrazin-6-yl]-5,7-dihydro-6H-pyrrolo[2,3-d]pyrimidin-6-one,
4-amino-5-methyl-5-phenyl-2-[8-(2,3,5-trifluorophenoxy)imidazo[1,2-a]pyrazin-6-yl]-5,7-dihydro-6H-pyrrolo[2,3-d]pyrimidin-6-one,
4-amino-2-[8-(2,3-difluorophenoxy)imidazo[1,2-a]pyrazin-6-yl]-5-methyl-5-phenyl-5,7-dihydro-6H-pyrrolo[2,3-d]pyrimidin-6-one,
4-amino-5-cyclopropyl-5-(4-fluorophenyl)-2-[8-(2,2,3,3,3-pentafluoropropoxy)imidazo[1,2-a]pyrazin-6-yl]-5,7-dihydro-6H-pyrrolo[2,3-d]pyrimidin-6-one,
4-amino-2-[8-(2,3-difluorophenoxy)imidazo[1,2-a]pyrazin-6-yl]-5-(4-fluorophenyl)-5-methyl-5,7-dihydro-6H-pyrrolo[2,3-d]pyrimidin-6-one,
4-amino-5-(4-fluorophenyl)-5-methyl-2-[8-(2,3,4-trifluorophenoxy)imidazo[1,2-a]pyrazin-6-yl]-5,7-dihydro-6H-pyrrolo[2,3-d]pyrimidin-6-one,
4-amino-5-(4-fluorophenyl)-5-methyl-2-[8-(2,3,5-trifluorophenoxy)imidazo[1,2-a]pyrazin-6-yl]-5,7-dihydro-6H-pyrrolo[2,3-d]pyrimidin-6-one,
4-amino-2-[8-(3,4-difluorophenoxy)imidazo[1,2-a]pyrazin-6-yl]-5-(4-fluorophenyl)-5-methyl-5,7-dihydro-6H-pyrrolo[2,3-d]pyrimidin-6-one,
4-amino-2-[8-(2,4-difluorophenoxy)imidazo[1,2-a]pyrazin-6-yl]-5-(4-fluorophenyl)-5-methyl-5,7-dihydro-6H-pyrrolo[2,3-d]pyrimidin-6-one,
4-amino-2-[8-(4-fluorophenoxy)imidazo[1,2-a]pyrazin-6-yl]-5-(4-fluorophenyl)-5-methyl-5,7-dihydro-6H-pyrrolo[2,3-d]pyrimidin-6-one,
4-amino-5-(4-fluorophenyl)-5-methyl-2-(8-{[5-(trifluoromethyl)pyridin-3-yl]oxy}imidazo[1,2-a]pyrazin-6-yl)-5,7-dihydro-6H-pyrrolo[2,3-d]pyrimidin-6-one,
4-amino-2-[8-(cyclohexyloxy)imidazo[1,2-a]pyrazin-6-yl]-5-(4-fluorophenyl)-5-methyl-5,7-dihydro-6H-pyrrolo[2,3-d]pyrimidin-6-one,
4-amino-2-[8-(3,5-difluorophenoxy)imidazo[1,2-a]pyrazin-6-yl]-5-(4-fluorophenyl)-5-methyl-5,7-dihydro-6H-pyrrolo[2,3-d]pyrimidin-6-one,
4-amino-2-[8-(3,5-difluorophenoxy)imidazo[1,2-a]pyrazin-6-yl]-5,5-dimethyl-5,7-dihydro-6H-pyrrolo[2,3-d]pyrimidin-6-one,
4-amino-2-[8-(2,5-difluorophenoxy)imidazo[1,2-a]pyrazin-6-yl]-5-(4-fluorophenyl)-5-methyl-5,7-dihydro-6H-pyrrolo[2,3-d]pyrimidin-6-one,
4-amino-2-[8-(2,5-difluorophenoxy)imidazo[1,2-a]pyrazin-6-yl]-5,5-dimethyl-5,7-dihydro-6H-pyrrolo[2,3-d]pyrimidin-6-one,
4-amino-5-(4-chlorophenyl)-2-[8-(2,5-difluorophenoxy)imidazo[1,2-a]pyrazin-6-yl]-5-methyl-5,7-dihydro-6H-pyrrolo[2,3-d]pyrimidin-6-one,
4-amino-5-(4-chlorophenyl)-2-{8-[(4,4-difluorocyclohexyl)oxy]imidazo[1,2-a]pyrazin-6-yl}-5-methyl-5,7-dihydro-6H-pyrrolo[2,3-d]pyrimidin-6-one,
4-amino-5-(4-fluorophenyl)-5-methyl-2-[8-(pyridin-3-yloxy)imidazo[1,2-a]pyrazin-6-yl]-5,7-dihydro-6H-pyrrolo[2,3-d]pyrimidin-6-one,
4-amino-5-(4-chlorophenyl)-5-methyl-2-[8-(pyridin-3-yloxy)imidazo[1,2-a]pyrazin-6-yl]-5,7-dihydro-6H-pyrrolo[2,3-d]pyrimidin-6-one,
4-amino-2-{8-[(3,3-difluorocyclobutyl)methoxy]imidazo[1,2-a]pyrazin-6-yl}-5-(4-fluorophenyl)-5-methyl-5,7-dihydro-6H-pyrrolo[2,3-d]pyrimidin-6-one,
4-amino-5-(4-chlorophenyl)-2-{8-[(3,3-difluorocyclobutyl)methoxy]imidazo[1,2-a]pyrazin-6-yl}-5-methyl-5,7-dihydro-6H-pyrrolo[2,3-d]pyrimidin-6-one,
4-amino-2-{8-[(3,3-difluorocyclobutyl)methoxy]imidazo[1,2-a]pyrazin-6-yl}-5-(5-fluoropyridin-2-yl)-5-methyl-5,7-dihydro-6H-pyrrolo[2,3-d]pyrimidin-6-one,
4-amino-5-(4-fluorophenyl)-5-methyl-2-{8-[(2,2,3,3,3-pentafluoropropyl)amino]imidazo[1,2-a]pyrazin-6-yl}-5,7-dihydro-6H-pyrrolo[2,3-d]pyrimidin-6-one,
4-Amino-2-(8-(3-fluorophenoxy)-2-(trifluoromethyl)imidazo[1,2-a]pyrazin-6-yl)-5-(4-fluorophenyl)-5-methyl-5H-pyrrolo[2,3-d]pyrimidin-6(7H)-one,
4-amino-5-(4-fluorophenyl)-5-methyl-2-(8-phenoxy-2-(trifluoromethyl)imidazo[1,2-a]pyrazin-6-yl)-5H-pyrrolo[2,3-d]pyrimidin-6(7H)-one, 4-amino-2-(8-(2,3-difluorophenoxy)-2-(trifluoromethyl)imidazo[1,2-a]pyrazin-6-yl)-5-(4-fluorophenyl)-5-methyl-5H-pyrrolo[2,3-d]pyrimidin-6(7H)-one, 4-amino-2-[2-cyclopropyl-8-(3-fluorophenoxy)imidazo[1,2-a]pyrazin-6-yl]-5-(4-fluorophenyl)-5-methyl-5,7-dihydro-6H-pyrrolo[2,3-d]pyrimidin-6-one, 4-Amino-5-(4-fluorophenyl)-5-methyl-2-(8-propoxyimidazo[1,2-a]pyrazin-6-yl)-5,7-dihydro-6H-pyrrolo[2,3-d]pyrimidin-6-one, 4-Amino-5-(4-chlorophenyl)-2-{8-[(2-methoxyethyl)amino]imidazo[1,2-a]pyrazin-6-yl}-5-methyl-5,7-dihydro-6H-pyrrolo[2,3-d]pyrimidin-6-one, 4-amino-2-{8-[2-(2,2-difluorocyclopropyl)ethoxy]imidazo[1,2-a]pyrazin-6-yl}-5-(4-fluorophenyl)-5-methyl-5,7-dihydro-6H-pyrrolo[2,3-d]pyrimidin-6-one, 4-amino-2-{8-[2-(3,3-difluorocyclobutyl)ethoxy]imidazo[1,2-a]pyrazin-6-yl}-5-(4-fluorophenyl)-5-methyl-5,7-dihydro-6H-pyrrolo[2,3-d]pyrimidin-6-one, 4-amino-2-[8-(cyclohexylmethoxy)imidazo[1,2-a]pyrazin-6-yl]-5-(4-fluorophenyl)-5-methyl-5,7-dihydro-6H-pyrrolo[2,3-d]pyrimidin-6-one, 4-amino-2-[8-(2-cyclopropylethoxy)imidazo[1,2-a]pyrazin-6-yl]-5-(4-fluorophenyl)-5-methyl-5,7-dihydro-6H-pyrrolo[2,3-d]pyrimidin-6-one, 4-amino-2-[8-(cyclopentylmethoxy)imidazo[1,2-a]pyrazin-6-yl]-5-(4-fluorophenyl)-5-methyl-5,7-dihydro-6H-pyrrolo[2,3-d]pyrimidin-6-one, 4-amino-2-[8-(cyclopentyloxy)imidazo[1,2-a]pyrazin-6-yl]-5-(4-fluorophenyl)-5-methyl-5,7-dihydro-6H-pyrrolo[2,3-d]pyrimidin-6-one, 4-amino-5-(4-chlorophenyl)-5-methyl-2-[8-(2,2,3,3,3-pentafluoropropoxy)imidazo[1,2-a]pyrazin-6-yl]-5,7-dihydro-6H-pyrrolo[2,3-d]pyrimidin-6-one, 4-amino-2-[8-(benzyloxy)imidazo[1,2-a]pyrazin-6-yl]-5-(4-chlorophenyl)-5-methyl-5,7-dihydro-6H-pyrrolo[2,3-d]pyrimidin-6-one, 4-amino-5-(4-chlorophenyl)-2-(8-propoxyimidazo[1,2-a]pyrazin-6-yl)-5,7-dihydro-6H-pyrrolo[2,3-d]pyrimidin-6-one, 4-amino-5-(4-chlorophenyl)-2-[8-(2-cyclopropylethoxy)imidazo[1,2-a]pyrazin-6-yl]-5-methyl-5,7-dihydro-6H-pyrrolo[2,3-d]pyrimidin-6-one, 4-amino-5-(4-fluorophenyl)-5-methyl-2-[8-(2-methylpropoxy)imidazo[1,2-a]pyrazin-6-yl]-5,7-dihydro-6H-pyrrolo[2,3-d]pyrimidin-6-one, 4-amino-5-(4-fluorophenyl)-2-{8-[(2-methoxyethyl)amino]imidazo[1,2-a]pyrazin-6-yl}-5-methyl-5,7-dihydro-6H-pyrrolo[2,3-d]pyrimidin-6-one, 4-amino-2-(8-{[(3,3-difluorocyclobutyl)methyl]amino}imidazo[1,2-a]pyrazin-6-yl)-5-(4-fluorophenyl)-5-methyl-5,7-dihydro-6H-pyrrolo[2,3-d]pyrimidin-6-one, 4-amino-2-(8-{[(1-ethylcyclopropyl)methyl]amino}imidazo[1,2-a]pyrazin-6-yl)-5-(4-fluorophenyl)-5-methyl-5,7-dihydro-6H-pyrrolo[2,3-d]pyrimidin-6-one, 4-amino-2-{8-[(cyclohexylmethyl)amino]imidazo[1,2-a]pyrazin-6-yl}-5-(4-fluorophenyl)-5-methyl-5,7-dihydro-6H-pyrrolo[2,3-d]pyrimidin-6-one, 4-amino-5-(4-chlorophenyl)-2-(8-{[(2,2-dimethylcyclopropyl)methyl]amino}imidazo[1,2-a]pyrazin-6-yl)-5-methyl-5,7-dihydro-6H-pyrrolo[2,3-d]pyrimidin-6-one, 4-amino-5-(4-chlorophenyl)-2-(8-{[(1-ethylcyclopropyl)methyl]amino}imidazo[1,2-a]pyrazin-6-yl)-5-methyl-5,7-dihydro-6H-pyrrolo[2,3-d]pyrimidin-6-one, 4-amino-5-(4-chlorophenyl)-2-(8-{[(3,3-difluorocyclobutyl)methyl]amino}imidazo[1,2-a]pyrazin-6-yl)-5-methyl-5,7-dihydro-6H-pyrrolo[2,3-d]pyrimidin-6-one, 4-amino-5-(4-chlorophenyl)-5-methyl-2-{8-[(tetrahydro-2H-pyran-4-ylmethyl)amino]imidazo[1,2-a]pyrazin-6-yl}-5,7-dihydro-6H-pyrrolo[2,3-d]pyrimidin-6-one, 4-amino-2-[8-(benzylamino)imidazo[1,2-a]pyrazin-6-yl]-5-(4-chlorophenyl)-5-methyl-5,7-dihydro-6H-pyrrolo[2,3-d]pyrimidin-6-one, 4-amino-5-(4-chlorophenyl)-5-methyl-2-{8-[(2,2,3,3,3-pentafluoropropyl)amino]imidazo[1,2-a]pyrazin-6-yl}-5,7-dihydro-6H-pyrrolo[2,3-d]pyrimidin-6-one, 4-amino-5-(4-fluorophenyl)-5-methyl-2-[8-(propylsulfanyl)imidazo[1,2-a]pyrazin-6-yl]-5,7-dihydro-6H-pyrrolo[2,3-d]pyrimidin-6-one, 4-amino-5-(4-fluorophenyl)-5-methyl-2-{8-[(2-methylpropyl)sulfanyl]imidazo[1,2-a]pyrazin-6-yl}-5,7-dihydro-6H-pyrrolo[2,3-d]pyrimidin-6-one, 4-amino-5-(4-fluorophenyl)-5-methyl-2-{8-[(3,3,3-trifluoropropyl)sulfanyl]imidazo[1,2-a]pyrazin-6-yl}-5,7-dihydro-6H-pyrrolo[2,3-d]pyrimidin-6-one, 4-amino-5-(4-fluorophenyl)-5-methyl-2-[8-(1-methylbutoxy)imidazo[1,2-a]pyrazin-6-yl]-5,7-dihydro-6H-pyrrolo[2,3-d]pyrimidin-6-one, 4-amino-5-(4-chlorophenyl)-5-methyl-2-[8-(tetrahydro-2H-pyran-3-ylmethoxy)imidazo[1,2-a]pyrazin-6-yl]-5,7-dihydro-6H-pyrrolo[2,3-d]pyrimidin-6-one, 4-amino-5-(4-chlorophenyl)-5-methyl-2-[8-(tetrahydro-2H-pyran-3-ylmethoxy)imidazo[1,2-a]pyrazin-6-yl]-5,7-dihydro-6H-pyrrolo[2,3-d]pyrimidin-6-one, 4-amino-5-(4-chlorophenyl)-5-methyl-2-[8-(tetrahydro-2H-pyran-2-ylmethoxy)imidazo[1,2-a]pyrazin-6-yl]-5,7-dihydro-6H-pyrrolo[2,3-d]pyrimidin-6-one, 4-amino-5-(4-chlorophenyl)-5-methyl-2-{8-[(1S)-1-phenylethoxy]imidazo[1,2-a]pyrazin-6-yl}-5,7-dihydro-6H-pyrrolo[2,3-d]pyrimidin-6-one, 4-amino-5-(4-chlorophenyl)-5-methyl-2-{8-[(tetrahydro-2H-pyran-2-ylmethyl)amino]imidazo[1,2-a]pyrazin-6-yl}-5,7-dihydro-6H-pyrrolo[2,3-d]pyrimidin-6-one, 4-amino-5-(4-chlorophenyl)-5-methyl-2-{8-[(tetrahydro-2H-pyran-3-ylmethyl)amino]imidazo[1,2-a]pyrazin-6-yl}-5,7-dihydro-6H-pyrrolo[2,3-d]pyrimidin-6-one, 4-amino-5-(4-chlorophenyl)-5-methyl-2-{8-[(1-phenylethyl)amino]imidazo[1,2-a]pyrazin-6-yl}-5,7-dihydro-6H-pyrrolo[2,3-d]pyrimidin-6-one, and 4-amino-5-(4-chlorophenyl)-5-methyl-2-{8-[(1-phenylethyl)amino]imidazo[1,2-a]pyrazin-6-yl}-5,7-dihydro-6H-pyrrolo[2,3-d]pyrimidin-6-one, or a pharmaceutically acceptable salt thereof.

* * * * *